US012336984B2

(12) United States Patent
Brauer et al.

(10) Patent No.: US 12,336,984 B2
(45) Date of Patent: *Jun. 24, 2025

(54) AMLODIPINE FORMULATIONS

(71) Applicant: Azurity Pharmaceuticals, Inc., Woburn, MA (US)

(72) Inventors: Scott Brauer, Harrisonville, MO (US); Gerold L. Mosher, Kansas City, MO (US)

(73) Assignee: AZURITY PHARMACEUTICALS, INC., Woburn, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/794,128

(22) Filed: Aug. 5, 2024

(65) Prior Publication Data

US 2024/0390347 A1    Nov. 28, 2024

Related U.S. Application Data

(63) Continuation of application No. 17/716,505, filed on Apr. 8, 2022, now Pat. No. 12,053,461, which is a continuation of application No. 17/194,016, filed on Mar. 5, 2021, now Pat. No. 11,364,230, which is a continuation of application No. 16/927,678, filed on Jul. 13, 2020, now Pat. No. 10,952,998, which is a continuation of application No. 16/853,380, filed on Apr. 20, 2020, now Pat. No. 10,894,039, which is a continuation of application No. 15/726,901, filed on Oct. 6, 2017, now Pat. No. 10,695,329.

(60) Provisional application No. 62/405,455, filed on Oct. 7, 2016.

(51) Int. Cl.

| | |
|---|---|
| *A01N 37/00* | (2006.01) |
| *A01N 25/00* | (2006.01) |
| *A01N 37/12* | (2006.01) |
| *A01N 37/44* | (2006.01) |
| *A61K 9/08* | (2006.01) |
| *A61K 31/215* | (2006.01) |
| *A61K 31/24* | (2006.01) |
| *A61K 31/4422* | (2006.01) |
| *A61K 47/02* | (2006.01) |
| *A61K 47/12* | (2006.01) |
| *A61K 47/26* | (2006.01) |
| *A61K 47/34* | (2017.01) |
| *A61K 47/38* | (2006.01) |

(52) U.S. Cl.
CPC ............ *A61K 31/4422* (2013.01); *A61K 9/08* (2013.01); *A61K 47/02* (2013.01); *A61K 47/12* (2013.01); *A61K 47/26* (2013.01); *A61K 47/34* (2013.01); *A61K 47/38* (2013.01)

(58) Field of Classification Search
None
See application file for complete search history.

(56) References Cited

U.S. PATENT DOCUMENTS

| | | |
|---|---|---|
| 4,879,303 A | 11/1989 | Davison et al. |
| 6,057,344 A | 5/2000 | Young |
| 6,291,490 B1 | 9/2001 | Young |
| 6,333,342 B1 | 12/2001 | Foster |
| 6,448,275 B2 | 9/2002 | Young |
| 6,451,826 B2 | 9/2002 | Young |
| 6,479,525 B2 | 11/2002 | Lemmens et al. |
| 6,518,288 B2 | 2/2003 | Lemmens et al. |
| 6,538,012 B2 | 3/2003 | Ettema et al. |
| 6,600,047 B2 | 7/2003 | Benneker et al. |
| 6,646,131 B2 | 11/2003 | Zhang et al. |
| 6,653,481 B2 | 11/2003 | Peters et al. |
| 6,680,334 B2 | 1/2004 | Bentham et al. |
| 6,822,099 B2 | 11/2004 | Senanayake et al. |
| 6,846,931 B2 | 1/2005 | Youn et al. |
| 6,890,944 B2 | 5/2005 | Cho et al. |
| 6,903,124 B2 | 6/2005 | Cho et al. |
| 7,015,238 B2 | 3/2006 | Lim et al. |
| 7,115,638 B2 | 10/2006 | Lemmens et al. |
| 7,199,247 B2 | 4/2007 | Lemmens et al. |
| 7,772,400 B2 | 8/2010 | Kim et al. |
| 8,158,146 B2 | 4/2012 | Kadosh et al. |
| 8,377,994 B2 | 2/2013 | Gray et al. |
| 10,695,329 B2 | 6/2020 | Brauer et al. |
| 10,799,453 B2 | 10/2020 | Brauer et al. |
| 10,894,039 B2 | 1/2021 | Brauer et al. |
| 10,952,998 B2 | 3/2021 | Brauer et al. |
| 10,959,991 B2 | 3/2021 | Brauer et al. |
| 11,364,230 B2 | 6/2022 | Brauer et al. |
| 11,471,409 B2 | 10/2022 | Brauer et al. |
| 11,484,498 B2 | 11/2022 | Brauer et al. |

(Continued)

FOREIGN PATENT DOCUMENTS

| | | |
|---|---|---|
| CN | 101416966 A | 4/2009 |
| CN | 101843615 A | 9/2010 |

(Continued)

OTHER PUBLICATIONS

Advisory Action with Examiner Initiated Interview Summary and AFCP 2.0 Decision dated Mar. 17, 2020 for U.S. Appl. No. 16/381,575.

Allen, Jr., Allen V.: Amlodipine 1 mg/mL Oral Liquid. Cardiovascular. US Pharm. 39(2):55-56 2014.

Ananchenko, G. et al.: Chapter 2—Amlodipine Besylate. Britain, Profiles of Drug Substances, Excipients, and Related Methodology 37 (2012).

(Continued)

*Primary Examiner* — Layla Soroush
(74) *Attorney, Agent, or Firm* — Wilson Sonsini Goodrich & Rosati

(57) ABSTRACT

Provided herein are stable amlodipine oral liquid formulations. Also provided herein are methods of using amlodipine oral liquid formulations for the treatment of certain diseases including hypertension and Coronary Artery Disease (CAD).

30 Claims, 2 Drawing Sheets

(56) References Cited

U.S. PATENT DOCUMENTS

| | | | |
|---|---|---|---|
| 11,701,326 | B2 | 7/2023 | Brauer et al. |
| 11,918,685 | B2 | 3/2024 | Brauer et al. |
| 12,053,461 | B2 | 8/2024 | Brauer et al. |
| 2002/0176889 | A1 | 11/2002 | Lemmens et al. |
| 2003/0199559 | A1 | 10/2003 | Benneker et al. |
| 2005/0019395 | A1 | 1/2005 | Pragai et al. |
| 2006/0030602 | A1 | 2/2006 | Laughlin et al. |
| 2006/0035940 | A1 | 2/2006 | Laughlin et al. |
| 2009/0098200 | A1 | 4/2009 | Temtsin et al. |
| 2011/0212169 | A1 | 9/2011 | Bae et al. |
| 2011/0294860 | A1 | 12/2011 | Tatsumi et al. |
| 2012/0177733 | A1 | 7/2012 | Joshi et al. |
| 2014/0024723 | A1 | 1/2014 | Brackhagen et al. |

FOREIGN PATENT DOCUMENTS

| | | |
|---|---|---|
| CN | 102018708 A | 4/2011 |
| CN | 102114017 A | 7/2011 |
| CN | 102370965 A | 3/2012 |
| CN | 102746215 A | 10/2012 |
| EP | 2676660 A1 | 12/2013 |
| EP | 2952207 A1 | 12/2015 |
| EP | 3773574 A1 | 2/2021 |
| EP | 3522872 B1 | 8/2021 |
| EP | 3960158 A1 | 3/2022 |
| WO | WO-02053134 A1 | 7/2002 |
| WO | WO-2005079772 A2 | 9/2005 |
| WO | WO-2005099699 A1 | 10/2005 |
| WO | WO-2006059217 A1 | 6/2006 |
| WO | WO-2008001341 A1 | 1/2008 |
| WO | WO-2010070705 A1 | 6/2010 |
| WO | WO-2012142815 A1 | 10/2012 |
| WO | WO-2018067959 A1 | 4/2018 |
| WO | WO-2019200143 A1 | 10/2019 |

OTHER PUBLICATIONS

Bellay, R. et al.: Stability of 5 mg/mL Nitrendipine Oral Suspension in Syrspend® SF PH4. Pharmaceutical Technology in Hospital Pharmacy 3(1):31-37 (2018).

Bernard et al.: Spectrophotometric method of estimation of Amlodipine besylate using hydrotropic solubilization; Journal of Applied Pharmaceutical Science 01 (09); 177-180 (2011).

Blowey: Update on the pharmacologic treatment of hypertension in pediatrics. Journal of Clinical Hypertension 14(6), 383-387 (2012).

Dhapte et al.: Advances in hydrotropic solutions: An updated review. St. Petersburg Polytechnical University Journal; Physics and Mathematics, vol. 1, Issue 4, pp. 424-436 (2015).

EP21190149.1 European Examination Report dated Apr. 23, 2024.

Extended European Search Report dated Apr. 21, 2020 for EP Application No. 17859269.7.

Extended European Search Report issued in European Patent Application No. 19784696.7 on Jan. 28, 2022.

Ferreira, A.O. et al.: Feasibility of amlodipine besylate, chloroquine phosphate, dapsone, phenytoin, pyridoxine hydrochloride, sulfadiazine, sulfasalazine, tetracycline hydrochloride, trimethoprim and zonisamide in SyrSpend SF PH4 oral suspensions, Journal of Pharmaceutical and Biomedical Analysis 118:105-112 (2016).

Final Office Action dated Dec. 31, 2019, for U.S. Appl. No. 16/381,575.

Final Office Action dated Nov. 15, 2019, for U.S. Appl. No. 15/726,901.

Flynn, J.T. et al.: Calcium channel blockers: pharmacology and place in therapy of pediatric hypertension, Pediatr Nephrol 15:302-316 (2000).

Friciu, M. et al.: Stability of Diazoxide in Extemporaneously Compounded Oral Suspensions. PLoS One 11(10):1-12 (2016).

Friciu, M. et al.: Stability of Extemporaneously Compounded Amlodipine Besylate Oral Suspensions, CJHP 69(4):327-329 (2016).

Gad, S.C. et al.: Tolerable Levels of Nonclinical Vehicles and Formulations Used in Studies by Multiple Routes in Multiple Species With Notes on Methods to Improve Utility. Int J Toxicol. 35(2):95-178 (2016).

International Search Report and Written Opinion dated Dec. 28, 2017, for PCT/US17/055576.

International Search Report and Written Opinion dated Jun. 27, 2019, for PCT/US19/27044.

Jain et al.: Spectrophotometric Method Development and Validation for Quantitative Estimation of Amlodipine Besylate in Bulk Drug and Their Dosage Forms by Using Hydrotropic Agent; Eurasian J. Anal. Chem. 5(3); 212-217 (2010).

Meyers et al.: Pharmacotherapy Review of Chronic Pediatric Hypertension. Clinical Therapeutics 33(10):1331-1356 (2011). Database: CAPLUS, DOI:10.1016/j.clinthera.2011.09.003.

Nahata et al.: Stability of Amlodipine Besylate; Research; Journal of the American Pharmaceutical Association; 375-377: 39(3) (1999).

Niazi, Sarfaraz K.: Handbook of Pharmaceutical Manufacturing Formulations: Liquid Products, vol. 3, Second edition. New York: Informa Healthcare USA, Inc., 2009, 400 pages.

Non-Final Office Action dated Aug. 7, 2020, for U.S. Appl. No. 16/927,678.

Non-Final Office Action dated May 14, 2020 for U.S. Appl. No. 16/381,575.

Notice of Allowance dated Mar. 27, 2020 for U.S. Appl. No. 15/726,901.

Notice of Allowance of U.S. Appl. No. 18/203,266 issued Dec. 7, 2023.

Nunn et al.: Formulation of medicines for children. British Journal of Clinical Pharmacology, 59:6, pp. 674-676 (2005).

Office Action dated Aug. 15, 2023 issued in U.S. Appl. No. 18/203,266.

PCT/US2017/055576 International Search Report and Written Opinion dated Dec. 28, 2017.

Pfizer, "NORVASC—amlodipine besylate" Pfizer Labs, 2011. Reference ID: 2943634.

Rivero, N.L. et al.: Amlodipine in pediatric patient with uncontrolled multifactorial hypertension; formulation of amlodipine oral suspension. European Review for Medical and Pharmacological Sciences 16:1117-1119 (2012).

Rosemont Pharmaceuticals Limited, Yorkdale Industrial Park, Braithwaite Street Leeds, LS11 9XE, United Kingdom, "Pharmaceutical product sheet for Amlodipine 1mg/ml Oral Solution," https://www.medicines.org.uk/emc/medicine/30460 (9 pgs.) (retrieved Sep. 12, 2016).

Salma, et al.: The relevancy of controlled nanocrystallization on rifampicin characteristics and cytotoxicity. International Journal of Nanomedicine 2209-2222 (2016).

Seikaly: Hypertension in children: an update on treatment strategies. Current Opinion in Pediatrics, 19:170-177, 2007.

Standing et al.: Paediatric formulations-Getting to the heart of the problem. International Journal of Pharmaceutics 300(1-2):56-66 (2005). Database: CAPLUS.

Tallian, K.B. et al.: Efficacy of amlodipine in pediatric patients with hypertension Pediatr. Nephrol. 13:304-310 (1999).

U.S. Appl. No. 15/726,901 Final Office Action dated Dec. 21, 2018.

U.S. Appl. No. 15/726,901 Office Action dated May 16, 2019.

U.S. Appl. No. 15/726,901 Office Action dated May 3, 2018.

U.S. Appl. No. 16/381,575 Office Action dated Jun. 25, 2019.

U.S. Appl. No. 17/716,505 Notice of Allowance dated May 30, 2024.

U.S. Appl. No. 18/420,901 Office Action dated Aug. 14, 2024.

Van Der Vossen et al.: Design and stability study of an oral solution of amlodipine besylate for pediatric patients. European Journal of Pharmaceutical Sciences 92:220-223 (2016).

AMLODIPINE FORMULATIONS

CROSS-REFERENCE

This application is a continuation of U.S. patent application Ser. No. 17/716,505, filed Apr. 8, 2022, which is a continuation of U.S. patent application Ser. No. 17/194,016 filed Mar. 5, 2021, (now U.S. Pat. No. 11,364,230), issued on Jun. 21, 2022, which is a continuation of U.S. patent application Ser. No. 16/927,678 filed Jul. 13, 2020, (now U.S. Pat. No. 10,952,998), issued on Mar. 23, 2021, which is a continuation of U.S. patent application Ser. No. 16/853,380 filed Apr. 20, 2020, (now U.S. Pat. No. 10,894,039) issued on Jan. 19, 2021, which is a continuation of U.S. patent application Ser. No. 15/726,901 filed Oct. 6, 2017, (now U.S. Pat. No. 10,695,329), issued on Jun. 30, 2020, which claims the benefit of U.S. Provisional Application 62/405,455 filed Oct. 7, 2016, all of which are hereby incorporated by reference in their entirety.

BACKGROUND OF THE INVENTION

Hypertension, or high blood pressure, is a serious health issue in many countries. According to the National Heart Blood and Lung Institute, it is thought that about 1 in 3 adults in the United States alone have hypertension. Left unchecked, hypertension is considered a substantial risk factor for cardiovascular and other diseases including coronary heart disease, myocardial infarction, congestive heart failure, stroke and kidney failure. Hypertension is classified as primary (essential) hypertension or secondary hypertension. Primary hypertension has no known cause and may be related to a number of environmental, lifestyle and genetic factors such as stress, obesity, smoking, inactivity and sodium intake. Secondary hypertension can be caused by drug or surgical interventions or by abnormalities in the renal, cardiovascular or endocrine system.

A number of antihypertensive drugs are available for treating hypertension. Various therapeutic classes of antihypertensive drugs include alpha-adrenergic blockers, beta-adrenergic blockers, calcium-channel blockers, hypotensives, mineral corticoid antagonists, central alpha-agonists, diuretics and rennin-angiotensin-aldosterone inhibitors which include angiotensin II receptor antagonists (ARB) and angiotensin-converting enzyme (ACE) inhibitors. Angiotensin-converting enzyme (ACE) inhibitors inhibit angiotensin-converting enzyme (ACE), a peptidyl dipeptidase that catalyzes angiotension I to angiotension II, a potent vasoconstrictor involved in regulating blood pressure.

Amlodipine is a calcium channel blocker. It affects the movement of calcium into the cells of the heart and blood vessels. As a result, amlodipine relaxes blood vessels and increases the supply of blood and oxygen to the heart while reducing its workload. The structural formula of amlodipine is as follows:

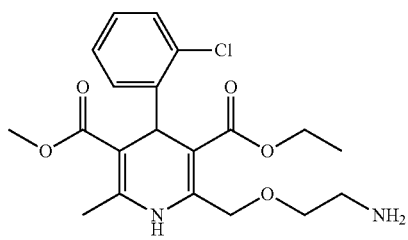 [SMILES: CCOC(=O)C1=C(COCCN)NC(C)=C(C(=O)OC)C1c1ccccc1Cl]

Amlodipine is currently administered in the form of oral tablets, (e.g., Norvasc®) or in the form of a refrigerated liquid formulation. In addition to the treatment of hypertension, amlodipine tablets have been used for coronary artery disease (CAD) such as chronic stable angina, vasospastic angina, or angiographically documented coronary artery disease in patients without heart failure or an ejection fraction<40%.

SUMMARY OF THE INVENTION

Disclosed herein is an oral liquid formulation, comprising: (i) amlodipine benzoate in an amount corresponding to 1.0 mg/ml amlodipine freebase; (ii) about 3 mM of a citrate buffer; (iii) about 0.2 mg/ml to about 10 mg/ml of sodium benzoate; (iv) about 0.5 mg/ml of silicon dioxide; (v) about 7.5 mg/ml of hydroxypropyl methylcellulose; (vi) about 0.15 mg/ml simethicone; (vii) about 1.0 mg/ml of polysorbate 80; and (viii) water; wherein the formulation is stable between about 5±5° C. and about 25±5° C. for at least 12 months. In some embodiments of an oral liquid formulation, the amlodipine benzoate is formed in situ. In some embodiments of an oral liquid formulation, the amlodipine benzoate is formed by the reaction of a pharmaceutically acceptable salt of amlodipine that is more soluble in aqueous media than amlodipine benzoate with a molar excess of sodium benzoate. In some embodiments of an oral liquid formulation, the salt of amlodipine that is more soluble in aqueous media than amlodipine benzoate is selected from amlodipine besylate, amlodipine tosylate, amlodipine mesylate, amlodipine succinate, amlodipine salicylate, amlodipine maleate, amlodipine acetate, and amlodipine hydrochloride. In some embodiments of an oral liquid formulation, the amlodipine benzoate is formed by the reaction of amlodipine besylate with a molar excess of sodium benzoate. In some embodiments of an oral liquid formulation, the formulation further comprises a flavoring agent. In some embodiments of an oral liquid formulation, the formulation further comprises a sweetener. In some embodiments of an oral liquid formulation, the sweetener is sucralose. In some embodiments of an oral liquid formulation, the formulation is in the form of a suspension. In some embodiments of an oral liquid formulation, the pH of the formulation is between about 3 and about 8. In some embodiments of an oral liquid formulation, the pH is between about 4 and about 5. In some embodiments of an oral liquid formulation, the pH is between about 5 and about 6. In some embodiments of an oral liquid formulation, the formulation is stable at about 25±5° C. for at least 12 months. In some embodiments of an oral liquid formulation, the formulation is stable at about 5±5° C. for at least 12 months. In some embodiments of an oral liquid formulation, the formulation is stable at about 25±5° C. for at least 24 months. In some embodiments of an oral liquid formulation, the formulation is stable at about 5±5° C. for at least 24 months.

Also disclosed herein is a method of treating hypertension in a subject comprising administering to that subject an oral liquid formulation, comprising: (i) amlodipine benzoate in an amount corresponding to 1.0 mg/ml amlodipine freebase; (ii) about 3 mM of a citrate buffer; (iii) about 0.2 mg/ml to about 10 mg/ml of sodium benzoate; (iv) about 0.5 mg/ml of silicon dioxide; (v) about 7.5 mg/ml of hydroxypropyl methylcellulose; (vi) about 0.15 mg/ml simethicone; (vii) about 1.0 mg/ml of polysorbate 80; and (viii) water; wherein the formulation is stable between about 5±5° C. and about 25±5° C. for at least 12 months. In some embodiments of a method of treating hypertension, the amlodipine benzoate is formed in situ. In some embodiments of a method of treating hypertension, the amlodipine benzoate is formed by the reaction of a pharmaceutically acceptable salt of amlodipine that is more soluble in aqueous media than amlodipine benzoate with a molar excess of sodium benzoate. In some embodiments of a method of treating hypertension, the salt of amlodipine that is more soluble in aqueous media than amlodipine benzoate is selected from amlodipine besylate, amlodipine tosylate, amlodipine mesylate, amlodipine succinate, amlodipine salicylate, amlodipine maleate, amlodipine acetate, and amlodipine hydrochloride. In some embodiments of a method of treating hypertension, the amlodipine benzoate is formed by the reaction of amlodipine besylate with a molar excess of sodium benzoate. In some embodiments of a method of treating hypertension, the formulation further comprises a flavoring agent. In some embodiments of a method of treating hypertension, the formulation further comprises a sweetener. In some embodiments of an oral liquid formulation, the sweetener is sucralose. In some embodiments of a method of treating hypertension, the formulation is in the form of a suspension. In some embodiments of a method of treating hypertension, the pH of the formulation is between about 3 and about 8. In some embodiments of a method of treating hypertension, the pH is between about 4 and about 5. In some embodiments of a method of treating hypertension, the pH is between about 5 and about 6. In some embodiments of a method of treating hypertension, the formulation is stable at about 25±5° C. for at least 12 months. In some embodiments of a method of treating hypertension, the formulation is stable at about 5±5° C. for at least 12 months. In some embodiments of a method of treating hypertension, the formulation is stable at about 25±5° C. for at least 24 months. In some embodiments of a method of treating hypertension, the formulation is stable at about 5±5° C. for at least 24 months. In some embodiments of a method of treating hypertension, the hypertension is primary (essential) hypertension. In some embodiments of a method of treating hypertension, the hypertension is secondary hypertension. In some embodiments of a method of treating hypertension, the subject has blood pressure values greater than or equal to 140/90 mmm Hg. In some embodiments of a method of treating hypertension, the subject is an adult. In some embodiments of a method of treating hypertension, the subject is elderly. In some embodiments of a method of treating hypertension, the subject is a child. In some embodiments of a method of treating hypertension, the formulation is administered to the subject in a fasted state. In some embodiments of a method of treating hypertension, the formulation is administered to the subject in a fed state. In some embodiments of a method of treating hypertension, the formulation is further administered in combination with an agent selected from the group consisting of diuretics, beta blockers, alpha blockers, mixed alpha and beta blockers, calcium channel blockers, angiotensin II receptor antagonists, ACE inhibitors, aldosterone antagonists, and alpha-2 agonists.

Also disclosed herein is a method of treating Coronary Artery Disease (CAD) in a subject comprising administering to that subject an oral liquid formulation, comprising: (i) amlodipine benzoate in an amount corresponding to 1.0 mg/ml amlodipine freebase; (ii) about 3 mM of a citrate buffer; (iii) about 0.2 mg/ml to about 10 mg/ml of sodium benzoate; (iv) about 0.5 mg/ml of silicon dioxide; (v) about 7.5 mg/ml of hydroxypropyl methylcellulose; (vi) about 0.15 mg/ml simethicone; (vii) about 1.0 mg/ml of polysorbate 80; and (viii) water; wherein the formulation is stable between about 5±5° C. and about 25±5° C. for at least 12 months. In some embodiments of a method of treating Coronary Artery Disease (CAD), the amlodipine benzoate is formed in situ. In some embodiments of a method of treating Coronary Artery Disease (CAD), the amlodipine benzoate is formed by the reaction of a pharmaceutically acceptable salt of amlodipine that is more soluble in aqueous media than amlodipine benzoate with a molar excess of sodium benzoate. In some embodiments of a method of treating Coronary Artery Disease (CAD), the salt of amlodipine that is more soluble in aqueous media than amlodipine benzoate is selected from amlodipine besylate, amlodipine tosylate, amlodipine mesylate, amlodipine succinate, amlodipine salicylate, amlodipine maleate, amlodipine acetate, and amlodipine hydrochloride. In some embodiments of a method of treating Coronary Artery Disease (CAD), the amlodipine benzoate is formed by the reaction of amlodipine besylate with a molar excess of sodium benzoate. In some embodiments of a method of treating Coronary Artery Disease (CAD), the formulation further comprises a flavoring agent. In some embodiments of a method of treating Coronary Artery Disease (CAD), the formulation further comprises a sweetener. In some embodiments of an oral liquid formulation, the sweetener is sucralose. In some embodiments of a method of treating Coronary Artery Disease (CAD), the formulation is in the form of a suspension. In some embodiments of a method of treating Coronary Artery Disease (CAD), the pH of the formulation is between about 3 and about 8. In some embodiments of a method of treating Coronary Artery Disease (CAD), the pH is between about 4 and about 5. In some embodiments of a method of treating Coronary Artery Disease (CAD), the pH is between about 5 and about 6. In some embodiments of a method of treating Coronary Artery Disease (CAD), the formulation is stable at about 25±5° C. for at least 12 months. In some embodiments of a method of treating Coronary Artery Disease (CAD), the formulation is stable at about 5±5° C. for at least 12 months. In some embodiments of a method of treating Coronary Artery Disease (CAD), the formulation is stable at about 25±5° C. for at least 24 months. In some embodiments of a method of treating Coronary Artery Disease (CAD), the formulation is stable at about 5±5° C. for at least 24 months. In some embodiments of a method of treating Coronary Artery Disease (CAD), the Coronary Artery Disease (CAD) is chronic stable angina, vasospastic angina, or angiographically documented coronary artery disease. In some embodiments of a method of treating Coronary Artery Disease (CAD), the angiographically documented coronary artery disease is in patients without heart failure or an ejection fraction<40%. In some embodiments of a method of treating Coronary Artery Disease (CAD), the formulation is further administered in combination with an additional anti-anginal agent.

Disclosed herein is an oral liquid formulation, comprising: (i) a pharmaceutically acceptable salt of amlodipine; (ii) a buffer; (iii) water; and (iv) optionally one or more agents selected from the group consisting of preservatives, flavoring agents, sweetening agents, surfactants, suspensions aids, and antifoaming agents; wherein the formulation is stable between about 5±5° C. and about 25±5° C. for at least 12 months. In some embodiments of an oral liquid formulation, the pharmaceutically acceptable salt of amlodipine is amlodipine benzoate or amlodipine naphthalene sulfonate. In some embodiments of an oral liquid formulation, the amlodipine benzoate or amlodipine naphthalene sulfonate are formed in situ. In some embodiments of an oral liquid formulation, the amlodipine benzoate or amlodipine naphthalene sulfonate are formed by the reaction of a pharmaceutically acceptable salt of amlodipine that is more soluble in aqueous media than amlodipine benzoate or amlodipine naphthalene sulfonate with a molar excess of a salt forming agent. In some embodiments of an oral liquid formulation, the pharmaceutically acceptable salt of amlodipine that is more soluble in aqueous media than amlodipine benzoate or amlodipine naphthalene sulfonate is amlodipine besylate. In some embodiments of an oral liquid formulation, the salt forming agent is sodium benzoate. In some embodiments of an oral liquid formulation, the amount of sodium benzoate as the salt forming agent is about 1.0 mg/ml to about 10.0 mg/ml. In some embodiments of an oral liquid formulation, the salt forming agent is sodium naphthalene-2-sulfonate. In some embodiments of an oral liquid formulation, the amount of sodium naphthalene-2-sulfonate as the salt forming agent is about 0.5 mg/ml to about 2.5 mg/ml. In some embodiments of an oral liquid formulation, the oral liquid formulation comprises a surfactant. In some embodiments of an oral liquid formulation, the surfactant is polysorbate 80. In some embodiments of an oral liquid formulation, the amount of the surfactant is about 0.1 mg/ml to about 2.5 mg/ml. In some embodiments of an oral liquid formulation, the oral liquid formulation comprises a preservative. In some embodiments of an oral liquid formulation, the preservative is selected from the group consisting of sodium benzoate, a paraben or paraben salt, and combinations thereof. In some embodiments of an oral liquid formulation, the amount of preservative is about 0.1 mg/ml to about 2.0 mg/ml. In some embodiments of an oral liquid formulation, the buffer comprises a citrate buffer. In some embodiments of an oral liquid formulation, the citrate buffer concentration is about 3 mM. In some embodiments of an oral liquid formulation, the buffer comprises a phosphate buffer. In some embodiments of an oral liquid formulation, the phosphate buffer concentration is about 3 mM. In some embodiments of an oral liquid formulation, the oral liquid formulation comprises a suspension aid. In some embodiments of an oral liquid formulation, the suspension aid comprises silicon dioxide, hydroxypropyl methylcellulose, methylcellulose, microcrystalline cellulose, carboxymethylcellulose sodium, polyvinylpyrrolidone, or combinations thereof. In some embodiments of an oral liquid formulation, the suspension aid is silicon dioxide. In some embodiments of an oral liquid formulation, the amount of silicon dioxide is about 0.1 mg/ml to about 1.0 mg/ml. In some embodiments of an oral liquid formulation, the suspension aid is hydroxypropyl methylcellulose. In some embodiments of an oral liquid formulation, the amount of hydroxypropyl methylcellulose is about 3 mg/ml to about 10 mg/ml. In some embodiments of an oral liquid formulation, the suspension aid is a combination of silicon dioxide and hydroxypropyl methylcellulose. In some embodiments of an oral liquid formulation, the amount of silicon dioxide is about 0.1 mg/ml to about 1.0 mg/ml and the amount of hydroxypropyl methylcellulose is about 3 mg/ml to about 10 mg/ml. In some embodiments of an oral liquid formulation, the oral liquid formulation comprises an antifoaming agent. In some embodiments of an oral liquid formulation, the antifoaming agent is simethicone. In some embodiments of an oral liquid formulation, the amount of the antifoaming agent is about 0.05 mg/ml to about 1.0 mg/ml. In some embodiments of an oral liquid formulation, the formulation comprises a flavoring agent. In some embodiments of an oral liquid formulation, the oral liquid formulation comprises a sweetener. In some embodiments of an oral liquid formulation, the sweetener is sucralose. In some embodiments of an oral liquid formulation, the oral liquid formulation further comprises unreacted salt forming agent. In some embodiments of an oral liquid formulation, the oral liquid formulation is in the form of a suspension. In some embodiments of an oral liquid formulation, the pH of the oral liquid formulation is between about 3 and about 8. In some embodiments of an oral liquid formulation, the pH is between about 4 and about 5. In some embodiments of an oral liquid formulation, the pH is between about 5 and about 6. In some embodiments of an oral liquid formulation, the amount of the pharmaceutically acceptable salt of amlodipine corresponds to about 0.8 mg/ml to about 1.2 mg/ml of amlodipine free base. In some embodiments of an oral liquid formulation, the formulation is stable at about 25±5° C. for at least 12 months. In some embodiments of an oral liquid formulation, the formulation is stable at about 5±5° C. for at least 12 months. In some embodiments of an oral liquid formulation, the formulation is stable at about 25±5° C. for at least 24 months. In some embodiments of an oral liquid formulation, the formulation is stable at about 5±5° C. for at least 24 months.

Also disclosed herein is an oral liquid formulation, comprising: (i) a pharmaceutically acceptable salt of amlodipine in an amount corresponding to 1.0 mg/ml amlodipine freebase; (ii) about 3 mM of a citrate buffer; (iii) about 0.2 mg/ml to about 10 mg/ml of sodium benzoate; (iv) about 0.5 mg/ml of silicon dioxide; (v) about 7.5 mg/ml of hydroxypropyl methylcellulose; (vi) about 0.15 mg/ml simethicone; (vii) optionally about 1.0 mg/ml of polysorbate 80; and (viii) water; wherein the formulation is stable between about 5±5° C. and about 25±5° C. for at least 12 months. In some embodiments of an oral liquid formulation, the pharmaceutically acceptable salt of amlodipine is amlodipine benzoate or amlodipine naphthalene sulfonate. In some embodiments of an oral liquid formulation, the amlodipine benzoate or amlodipine naphthalene sulfonate are formed in situ. In some embodiments of an oral liquid formulation, the amlodipine benzoate or amlodipine naphthalene sulfonate are formed by the reaction of amlodipine besylate with a molar excess of a salt forming agent. In some embodiments of an oral liquid formulation, the salt forming agent is sodium benzoate. In some embodiments of an oral liquid formulation, the amount of sodium benzoate as the salt forming agent is about 1.0 mg/ml to about 10.0 mg/ml. In some embodiments of an oral liquid formulation, the salt forming agent is sodium naphthalene-2-sulfonate. In some embodiments of an oral liquid formulation, the amount of sodium naphthalene-2-sulfonate as the salt forming agent is about 0.5 mg/ml to about 2.5 mg/ml. In some embodiments of an oral liquid formulation, the formulation further comprises a flavoring agent. In some embodiments of an oral liquid formulation, the formulation further comprises a sweetener. In some embodiments of an oral liquid formulation, the sweetener is sucralose. In some embodiments of an oral liquid formulation, the oral liquid formulation further comprises unreacted salt forming agent. In some embodiments of an oral liquid formulation, the formulation is in the form of a suspension. In some embodiments of an oral liquid formulation, the pH of the formulation is between about 3 and about 8. In some embodiments of an oral liquid formulation, the pH is between about 4 and about 5. In some embodiments of an oral liquid formulation, the pH is between about 5 and about 6. In some embodiments of an oral liquid formulation, the formulation is stable at about 25±5° C. for at least 12 months. In some embodiments of an oral liquid formulation, the formulation is stable at about 5±5° C. for at least 12 months. In some embodiments of an oral liquid formulation, the formulation is stable at about 25±5° C. for at least 24 months. In some embodiments of an oral liquid formulation, the formulation is stable at about 5±5° C. for at least 24 months.

Also disclosed herein is a process for preparing a stable amlodipine oral liquid formulation, the process comprising mixing a first mixture with a second mixture; the first mixture comprising: (i) amlodipine benzoate; (ii) sodium benzoate; (iii) optionally polysorbate 80; and (iv) water; and the second mixture comprising: (i) citric acid; (ii) sodium citrate; (iii) sucralose; (iv) optionally a flavoring agent; (v) hydroxypropyl methylcellulose; (vi) simethicone; (vii) silicon dioxide; and (viii) water. In some embodiments of a process for preparing a stable amlodipine oral liquid formulation, the first mixture is obtained by a process comprising: (i) adding water to a first container which is not stainless steel; (ii) adding amlodipine besylate to the first container; (iii) adding sodium benzoate to the first container; (iv) optionally adding polysorbate 80 to the first container; and (v) stirring until amlodipine benzoate substantially precipitates. In some embodiments of a process for preparing a stable amlodipine oral liquid formulation, the second mixture is obtained by a process comprising: (i) adding water to a second container; (ii) adding citric acid to the second container; (iii) adding sodium citrate to the second container; (iv) adding sucralose to the second container; (v) optionally adding the flavoring agent to the second container; (vi) adding hydroxypropyl methylcellulose to the second container; (vii) adding simethicone to the second container; (viii) adding silicon dioxide to the second container; and (ix) stirring.

Also disclosed herein is a process for preparing a stable amlodipine oral liquid formulation, the process comprising mixing a first mixture with a second mixture; the first mixture comprising: (i) amlodipine naphthalene sulfonate; (ii) optionally sodium benzoate; (iii) optionally polysorbate 80; and (iv) water; and the second mixture comprising: (i) citric acid; (ii) sodium citrate; (iii) sucralose; (iv) optionally a flavoring agent; (v) hydroxypropyl methylcellulose; (vi) simethicone; (vii) silicon dioxide; and (viii) water. In some embodiments of a process for preparing a stable amlodipine oral liquid formulation, the first mixture is obtained by a process comprising: (i) adding water to a first container which is not stainless steel; (ii) adding amlodipine besylate to the first container; (iii) adding sodium naphthalene-2-sulfonate to the first container; (iv) adding sodium benzoate to the first container; (v) optionally adding polysorbate 80 to the first container; and (vi) stirring until amlodipine naphthalene sulfonate substantially precipitates. In some embodiments of a process for preparing a stable amlodipine oral liquid formulation, the second mixture is obtained by a process comprising: (i) adding water to a second container; (ii) adding citric acid to the second container; (iii) adding sodium citrate to the second container; (iv) adding sucralose to the second container; (v) optionally adding the flavoring agent to the second container; (vi) adding hydroxypropyl methylcellulose to the second container; (vii) adding simethicone to the second container; (viii) adding silicon dioxide to the second container; and (ix) stirring. In some embodiments of a process for preparing a stable amlodipine oral liquid formulation, the first mixture does not comprise sodium benzoate and the second mixture further comprises a paraben.

Also disclosed herein is a method of treating hypertension in a subject comprising administering to that subject a therapeutically effective amount of an amlodipine oral liquid formulation comprising: (i) a pharmaceutically acceptable salt of amlodipine in an amount corresponding to 1.0 mg/ml amlodipine freebase; (ii) about 3 mM of a citrate buffer; (iii) about 0.2 mg/ml to about 10 mg/ml of sodium benzoate; (iv) about 0.5 mg/ml of silicon dioxide; (v) about 7.5 mg/ml of hydroxypropyl methylcellulose; (vi) about 0.15 mg/ml simethicone; (vii) optionally about 1.0 mg/ml of polysorbate 80; and (viii) water; wherein the formulation is stable between about 5±5° C. and about 25±5° C. for at least 12 months. In some embodiments of a method of treating hypertension, the pharmaceutically acceptable salt of amlodipine is amlodipine benzoate or amlodipine naphthalene sulfonate. In some embodiments of a method of treating hypertension, the amlodipine benzoate or amlodipine naphthalene sulfonate are formed in situ. In some embodiments of a method of treating hypertension, the oral liquid formulation further comprises unreacted salt forming agent. In some embodiments of a method of treating hypertension, the salt forming agent is sodium benzoate. In some embodiments of a method of treating hypertension, the salt forming agent is sodium naphthalene-2-sulfonate. In some embodiments of a method of treating hypertension, the hypertension is primary (essential) hypertension. In some embodiments of a method of treating hypertension, the hypertension is secondary hypertension. In some embodiments of a method of treating hypertension, the subject has blood pressure values greater than or equal to 140/90 mmm Hg. In some embodiments of a method of treating hypertension, the subject is an adult. In some embodiments of a method of treating hypertension, the subject is elderly. In some embodiments of a method of treating hypertension, the subject is a child. In some embodiments of a method of treating hypertension, the formulation is administered to the subject in a fasted state. In some embodiments of a method of treating hypertension, the formulation is administered to the subject in a fed state. In some embodiments of a method of treating hypertension, the formulation is further administered in combination with an agent selected from the group consisting of diuretics, beta blockers, alpha blockers, mixed alpha and beta blockers, calcium channel blockers, angiotensin II receptor antagonists, ACE inhibitors, aldosterone antagonists, and alpha-2 agonists.

Also disclosed herein is a method of treating Coronary Artery Disease (CAD) in a subject comprising administering to that subject a therapeutically effective amount of an amlodipine oral liquid formulation comprising: (i) a pharmaceutically acceptable salt of amlodipine in an amount corresponding to 1.0 mg/ml amlodipine freebase; (ii) about 3 mM of a citrate buffer; (iii) about 0.2 mg/ml to about 10 mg/ml of sodium benzoate; (iv) about 0.5 mg/ml of silicon dioxide; (v) about 7.5 mg/ml of hydroxypropyl methylcellulose; (vi) about 0.15 mg/ml simethicone; (vii) optionally about 1.0 mg/ml of polysorbate 80; and (viii) water; wherein the formulation is stable between about 5±5° C. and about 25±5° C. for at least 12 months. In some embodiments of a method of treating Coronary Artery Disease (CAD), the pharmaceutically acceptable salt of amlodipine is amlodipine benzoate or amlodipine naphthalene sulfonate. In some embodiments of a method of treating Coronary Artery Disease (CAD), the amlodipine benzoate or amlodipine naphthalene sulfonate are formed in situ. In some embodiments of a method of treating Coronary Artery Disease (CAD), the oral liquid formulation further comprises unreacted salt forming agent. In some embodiments of a method of treating Coronary Artery Disease (CAD), the salt forming agent is sodium benzoate. In some embodiments of a method of treating Coronary Artery Disease (CAD), the salt forming agent is sodium naphthalene-2-sulfonate. In some embodiments of a method of treating Coronary Artery Disease (CAD), the Coronary Artery Disease (CAD) is chronic stable angina, vasospastic angina, or angiographically documented coronary artery disease. In some embodiments of a method of treating Coronary Artery Disease (CAD), the angiographically documented coronary artery disease is in patients without heart failure or an ejection fraction<40%. In some embodiments of a method of treating Coronary Artery Disease (CAD), the formulation is further administered in combination with an additional anti-anginal agent.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
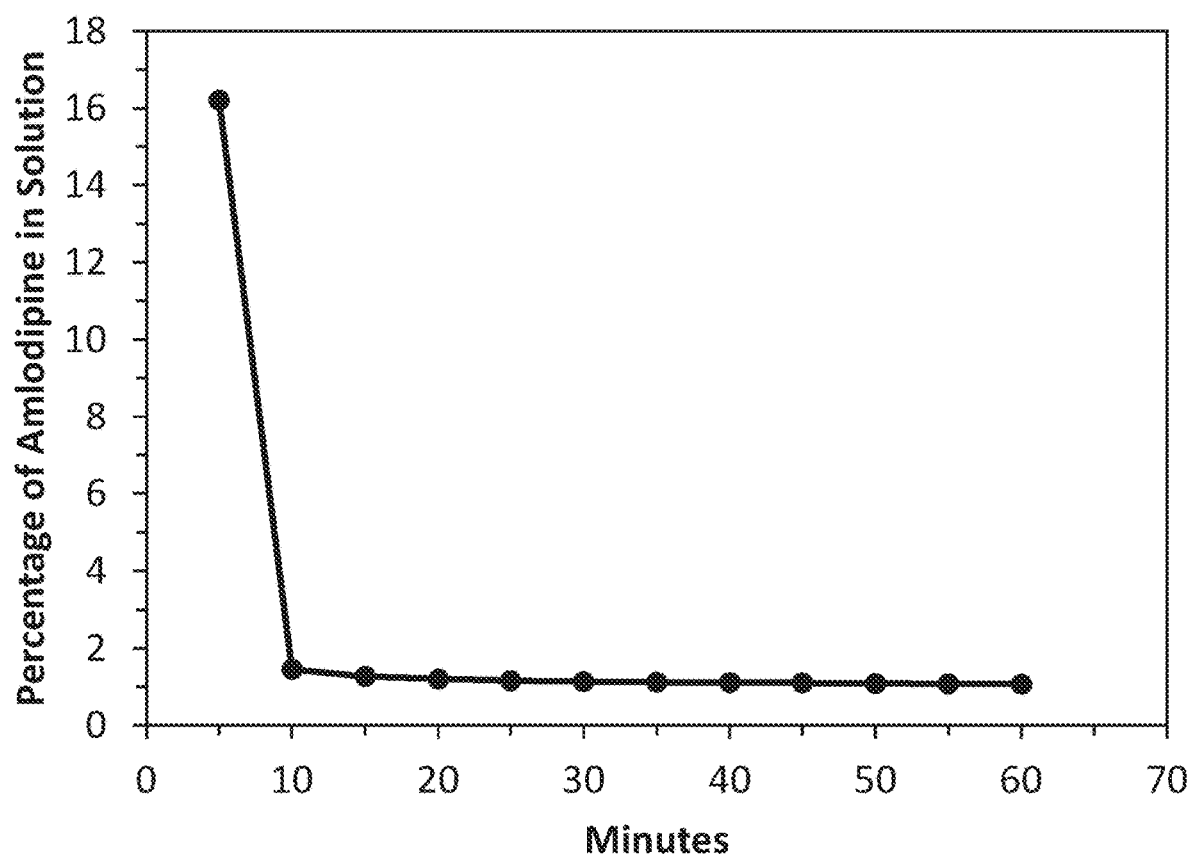
FIG. 1 shows the amount of amlodipine remaining in solution over time.

Provided herein are stable amlodipine oral liquid formulations. These amlodipine formulations described herein are useful for the treatment of hypertension and coronary artery disease. The formulations are advantageous over conventional solid dosage administration of amlodipine ranging from ease of administration, accuracy of dosing, accessibility to additional patient populations such as to children and the elderly, and an increased patient compliance to medication.

It is generally known that certain segments of the population have difficulty ingesting and swallowing solid oral dosage forms such as tablets and capsules. As many as a quarter of the total population has this difficulty. Often, this leads to non-compliance with the recommended medical therapy with the solid dosage forms, thereby resulting in rending the therapy ineffective. Further, solid dosage forms are not recommended for children or elderly due to increased risk in choking.

Furthermore, the dose of amlodipine to be given to children is calculated according to the child's weight. When the calculated dose is something other than the amount present in one or more intact solid dosage forms, the solid dosage form must be divided to provide the correct dose. This leads to inaccurate dosing when solid dosages forms, such as tablets, are compounded to prepare other formulations for children.

For amlodipine, one solution to overcoming the use of the tablet form is for a compounding pharmacist to pulverize and crush the amlodipine tablet(s) into a powder via mortar and pestle and reconstitute the powder in some liquid form. However, forming a amlodipine oral liquid in this fashion has significant drawbacks including large variability in the actual dosage, incomplete solubilizing of the amlodipine tablet in the liquid, rapid instability, inconsistent formulation methods per compounding pharmacy, and a number of other potential issues. The crushed tablet liquid formulation may also be potentially unsafe due to contamination with residual drugs and other substances from the mortar and pestle or other crushing agent.

The present embodiments described herein provide a safe and effective oral administration of amlodipine for the treatment of hypertension and other disorders. In particular, the embodiments provide stable amlodipine oral liquid formulations.

As used herein, "amlodipine" refers to amlodipine base, its salt, or solvate or derivative or isomer or polymorph thereof. Suitable compounds include the free base, the organic and inorganic salts, isomers, isomer salts, solvates, polymorphs, complexes etc. U.S. Pat. Nos. 4,572,909, 4,879,303, 6,846,931 and WO2002/053134 disclose amlodipine and exemplary amlodipine salt forms. In some embodiments, the amlodipine used in the formulations described herein is a pharmaceutically acceptable amlodipine salt. In some instances, the amlodipine salt is amlodipine benzoate. In other instances, the amlodipine salt is in the form of amlodipine naphthalene sulfonate.

Amlodipine Oral Liquid Formulations

Oral liquids include, but are not limited to, solutions (both aqueous and nonaqueous), suspensions, emulsions, syrups, slurries, juices, elixirs, dispersions, and the like. It is envisioned that solution/suspensions are also included where certain components described herein are in a solution while other components are in a suspension. In some embodiments, the oral liquid formulation is a suspension.

In one aspect, the amlodipine liquid formulations described herein comprise a pharmaceutically acceptable salt of amlodipine, a buffer, water, and optionally one or more agents selected from the group consisting of preservatives, flavoring agents, sweetening agents, surfactants, suspension aids, and antifoaming agents. In one embodiment, the buffer is a citrate buffer. In one embodiment, the buffer comprises citric acid. In some embodiments, the buffer further comprises sodium citrate. In one embodiment, the buffer is a phosphate buffer. In one embodiment, the optional sweetening agent is sucralose. In one embodiment, the optional sweetening agent is a combination of sucralose and maltodextrin. In one embodiment, the optional sweetening agent is not maltitol. In another embodiment, the optional sweetening agent is not sucrose. In another embodiment, the optional preservative is sodium benzoate. In some embodiments, the optional preservative is a paraben. In some embodiments, the optional preservative is a mixture of parabens. In one embodiment, the optional surfactant is a polysorbate. In some embodiments, the optional surfactant is polysorbate 80. In one embodiment, the optional suspension aid is silicon dioxide. In some embodiments, the silicon dioxide is colloidal silicon dioxide. In some embodiments, the optional suspension aid is hydroxypropyl methylcellulose. In some embodiments, the optional suspension aid is a combination of hydroxypropyl methylcellulose and silicon dioxide. In some embodiments, the optional suspension aid is polyvinylpyrrolidone. In some embodiments, the optional suspension aid is methyl cellulose. In one embodiment, the optional antifoaming agent is simethicone.

Pharmaceutically Acceptable Salt of Amlodipine in the Oral Liquid Formulations

Disclosed herein is a stable amlodipine oral liquid formulation. In some embodiments, the stable amlodipine oral liquid formulation is in the form of a suspension. In some embodiments, the stable amlodipine oral liquid formulation comprises a pharmaceutically acceptable salt of amlodipine which is not soluble in an aqueous media.

In some embodiments, the pharmaceutically acceptable salt of amlodipine is amlodipine benzoate or amlodipine naphthalene sulfonate. In some embodiments, amlodipine benzoate or amlodipine naphthalene sulfonate are formed in situ. In some embodiments, amlodipine benzoate or amlodipine naphthalene sulfonate are formed by the reaction of a pharmaceutically acceptable salt of amlodipine that is more soluble in aqueous media than amlodipine benzoate or amlodipine naphthalene sulfonate with a molar excess of a salt forming agent. In some embodiments, the pharmaceutically acceptable salt of amlodipine that is more soluble in aqueous media than amlodipine benzoate or amlodipine naphthalene sulfonate is selected from the group consisting of amlodipine besylate, amlodipine tosylate, amlodipine mesylate, amlodipine succinate, amlodipine salicylate, amlodipine maleate, amlodipine acetate, and amlodipine hydrochloride. In some embodiments, the pharmaceutically acceptable salt of amlodipine that is more soluble in aqueous media than amlodipine benzoate or amlodipine naphthalene sulfonate is amlodipine besylate.

In some embodiments, the pharmaceutically acceptable salt of amlodipine is amlodipine benzoate and is formed in situ by the reaction of a pharmaceutically acceptable salt of amlodipine that is more soluble in aqueous media than amlodipine benzoate with a benzoate salt forming agent. In some embodiments, the benzoate salt forming agent is benzoic acid, sodium benzoate, calcium benzoate, or potassium benzoate. In some embodiments, an excess of the benzoate salt forming agent is used to form the benzoate salt in situ. In some embodiments, the benzoate salt forming agent is sodium benzoate. In some embodiments, an excess of sodium benzoate is used to form the benzoate salt in situ. In some embodiments, the amount of sodium benzoate used as the salt forming agent is about 1.0 mg/ml to about 10.0 mg/ml. In some embodiments, the amount of sodium benzoate used as the salt forming agent is about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, about 2.5 mg/ml, about 2.6 mg/ml, about 2.7 mg/ml, about 2.8 mg/ml, about 2.9 mg/ml, about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6.0 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7.0 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8.0 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9.0 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, or about 10.0 mg/ml.

In some embodiments, the pharmaceutically acceptable salt of amlodipine is amlodipine naphthalene sulfonate and is formed in situ by the reaction of a pharmaceutically acceptable salt of amlodipine that is more soluble in aqueous media than amlodipine naphthalene sulfonate with a naphthalene sulfonate salt forming agent. In some embodiments, the naphthalene sulfonate salt forming agent is 1-naphthalene sulfonic acid, 2-naphthalene sulfonic acid, sodium naphthalene-1-sulfonate, sodium naphthalene-2-sulfonate, or potassium naphthalene-2-sulfonate. In some embodiments, an excess of the naphthalene sulfonate salt forming agent is used to form the naphthalene sulfonate salt in situ. In some embodiments, the naphthalene sulfonate salt forming agent is sodium naphthalene-2-sulfonate. In some embodiments, an excess of sodium naphthalene-2-sulfonate is used to form the naphthalene sulfonate salt in situ. In some embodiments, the amount of sodium naphthalene-2-sulfonate used as the salt forming agent is about 0.5 mg/ml to about 2.5 mg/ml. In some embodiments, the amount of sodium naphthalene-2-sulfonate used as the salt forming agent is about 0.5 mg/ml, about 0.6 mg/ml, about 0.7 mg/ml, about 0.8 mg/ml, about 0.9 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, about 2.0 mg/ml, about 2.1 mg/ml, about 2.2 mg/ml, about 2.3 mg/ml, about 2.4 mg/ml, or about 2.5 mg/ml.

In some embodiments, the amount of the pharmaceutically acceptable salt of amlodipine in the oral liquid formulation corresponds to about 0.8 mg/ml to about 1.2 mg/ml of amlodipine free base. In other embodiments, the amount of the pharmaceutically acceptable salt of amlodipine in the oral liquid formulation correspond to about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, about 1.0 mg/ml, about 1.01 mg/ml, about 1.02, mg/ml, about 1.03 mg/ml, about 1.04 mg/ml, about 1.05 mg/ml, about 1.06 mg/ml, about 1.07 mg/ml, about 1.08 mg/ml, about 1.09 mg/ml, about 1.1 mg/ml, about 1.11 mg/ml, about 1.12, mg/ml, about 1.13 mg/ml, about 1.14 mg/ml, about 1.15 mg/ml, about 1.16 mg/ml, about 1.17 mg/ml, about 1.18 mg/ml, about 1.19 mg/ml, or about 1.2 mg/ml of amlodipine free base. In some embodiments, the amount of the pharmaceutically acceptable salt of amlodipine in the oral liquid formulation corresponds to about 0.9 mg/ml to about 1.1 mg/ml of amlodipine free base. In some embodiments, the amount of the pharmaceutically acceptable salt of amlodipine in the oral liquid formulation corresponds to about 1.0 mg/ml of amlodipine free base. In some embodiments, the pharmaceutically acceptable salt of amlodipine is amlodipine benzoate. In some embodiments, the amount of amlodipine benzoate in the oral liquid formulation corresponds to about 1.0 mg/ml of amlodipine free base. In some embodiments, the pharmaceutically acceptable salt of amlodipine is amlodipine naphthalene sulfonate. In some embodiments, the amount of amlodipine naphthalene sulfonate in the oral liquid formulation corresponds to about 1.0 mg/ml of amlodipine free base.

In some embodiments, the amount of the pharmaceutically acceptable salt of amlodipine corresponds to about 1% w/w to about 16% w/w of the solids in the oral liquid formulation. In other embodiments, the amount of the pharmaceutically acceptable salt of amlodipine correspond to about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, about 10% w/w, about 10.1% w/w, about 10.2% w/w, about 10.3% w/w, about 10.4% w/w, about 10.5% w/w, about 10.6% w/w, about 10.7% w/w, about 10.8% w/w, about 10.9% w/w, about 11% w/w, about 11.1% w/w, about 11.2% w/w, about 11.3% w/w, about 11.4% w/w, about 11.5% w/w, about 11.6% w/w, about 11.7% w/w, about 11.8% w/w, about 11.9% w/w, about 12% w/w, about 12.1% w/w, about 12.2% w/w, about 12.3% w/w, about 12.4% w/w, about 12.5% w/w, about 12.6% w/w, about 12.7% w/w, about 12.8% w/w, about 12.9% w/w, about 13% w/w, about 13.1% w/w, about 13.2% w/w, about 13.3% w/w, about 13.4% w/w, about 13.5% w/w, about 13.6% w/w, about 13.7% w/w, about 13.8% w/w, about 13.9% w/w, about 14% w/w, about 14.1% w/w, about 14.2% w/w, about 14.3% w/w, about 14.4% w/w, about 14.5% w/w, about 14.6% w/w, about 14.7% w/w, about 14.8% w/w, about 14.9% w/w, about 15% w/w, about 15.1% w/w, about 15.2% w/w, about 15.3% w/w, about 15.4% w/w, about 15.5% w/w, about 15.6% w/w, about 15.7% w/w, about 15.8% w/w, about 15.9% w/w, or about 16% w/w of the solids in the oral liquid formulation.

Sweetener in the Amlodipine Oral Liquid Formulations

Sweeteners or sweetening agents include any compounds that provide a sweet taste. This includes natural and synthetic sugars, natural and artificial sweeteners, natural extracts and any material that initiates a sweet sensation in a subject. In some embodiments, a solid/powder sweetener is used in the oral liquid formulation described herein. In other embodiments, a liquid sweetening agent is used in the oral liquid formulation described herein.

Sweetening agents illustratively include glucose, fructose, sucrose, xylitol, tagatose, sucralose, maltitol, isomaltulose, Isomalt™ (hydrogenated isomaltulose), lactitol, sorbitol, erythritol, trehalose, maltodextrin, polydextrose, and the like. Other sweetening agents illustratively include glycerin, inulin, maltol, acesulfame and salts thereof, e.g., acesulfame potassium, alitame, aspartame, neotame, sodium cyclamate, saccharin and salts thereof, e.g., saccharin sodium or saccharin calcium, neohesperidin dihydrochalcone, stevioside, thaumatin, and the like. Sweetening agents can be used in the form of crude or refined products such as hydrogenated starch hydrolysates, maltitol syrup, high fructose corn syrup, etc., and as branded products, e.g., Sweet Am™ liquid (propylene glycol, ethyl alcohol, and proprietary artificial flavor combination, Flavors of North America), Sweet Am™ powder (Product Code 918.005—maltodextrin, sorbitol, and fructose combination and Product Code 918.010—water, propylene glycol, sorbitol, fructose, and proprietary natural and artificial flavor combination, Flavors of North America), ProSweet™ (1-10% proprietary plant/vegetable extract and 90-99% dextrose combination, Virginia Dare), Maltisweet™ (maltitol solution, Ingredion), Sorbo™ (sorbitol and sorbitol/xylitol solution, SPI Polyols), Invertose™ (high fructose corn syrup, Ingredion), Rebalance M60 and X60 (sucralose and maltodextrin, Tate and Lyle), and Ora-Sweet® and Ora-Sweet-SF®, sugar containing and sugar-free, respectively flavored syrups (Paddock Laboratories, Inc.). Sweetening agents can be used singly or in combinations of two or more. Suitable concentrations of different sweetening agents can be selected based on published information, manufacturers' data sheets and by routine testing.

In some embodiments, the amlodipine oral liquid formulation described herein comprises a sweetening agent. In some embodiments, the sweetening agent is sucralose. In some embodiments, the sweetening agent is a combination of sucralose and maltodextrin. In some embodiments, the sweetener is not maltitol. In some embodiments, the sweetener is not sucrose.

In some embodiments, the sweetening agent is present in about 0.5 mg/ml to about 0.9 mg/ml in the oral liquid formulation. In other embodiments, the sweetening agent is present in about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.60 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.70 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.80 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, or about 0.90 mg/ml in the oral liquid formulation. In some embodiments, the sweetening agent is present in about 0.6 mg/ml to about 0.8 mg/ml in the oral liquid formulation. In some embodiments, the sweetening agent is sucralose and is present in about 0.7 mg/ml in the oral liquid formulation.

In some embodiments, the sweetening agent is present in about 1% w/w to about 10% w/w of the solids in the oral liquid formulation. In some embodiments, the sweetening agent is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10% w/w of the solids in the oral liquid formulation.

Preservative in the Amlodipine Oral Liquid Formulations

Preservatives include anti-microbials, anti-oxidants, and agents that enhance sterility. Exemplary preservatives include ascorbic acid, ascorbyl palmitate, BHA, BHT, citric acid, EDTA and its salts, erythorbic acid, fumaric acid, malic acid, propyl gallate, sodium ascorbate, sodium bisulfate, sodium metabisulfite, sodium sulfite, parabens (such as methylparaben, ethylparaben, propylparaben, butylparaben and their salts), benzoic acid, sodium benzoate, potassium sorbate, vanillin, and the like.

In some embodiments, the amlodipine oral liquid formulation described herein comprises a preservative.

In some embodiments, the preservative is a paraben, or a mixture of parabens and the sweetener is a sugar (such as, but not limited to glucose, fructose, sucrose, lactose, maltose) or a sugar alcohol (such as, but not limited to xylitol, mannitol, lactitol, maltitol, sorbitol). In some embodiments, the preservative is a paraben, or a mixture of parabens and the sweetener is not a sugar or a sugar alcohol.

In some embodiments, the preservative is present in an amount sufficient to provide antimicrobial effectiveness to the amlodipine oral liquid formulation described herein. In some embodiments, the amount of preservative sufficient to provide antimicrobial effectiveness is between about 0.1 mg/ml and about 2.0 mg/ml. In other embodiments, the amount of preservative sufficient to provide antimicrobial effectiveness is about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, about 1.0 mg/ml, about 1.1 mg/ml, about 1.2 mg/ml, about 1.3 mg/ml, about 1.4 mg/ml, about 1.5 mg/ml, about 1.6 mg/ml, about 1.7 mg/ml, about 1.8 mg/ml, about 1.9 mg/ml, or about 2.0 mg/ml. In some embodiments, the preservative is sodium benzoate and the amount of sodium benzoate sufficient to provide antimicrobial effectiveness is between about 0.2 mg/ml and about 1.0 mg/ml. In some embodiments, the preservative is methyl paraben and the amount of methyl paraben sufficient to provide antimicrobial effectiveness is between about 1.0 mg/ml and about 2.0 mg/ml. In some embodiments, the preservative is propyl paraben and the amount of propyl paraben sufficient to provide antimicrobial effectiveness is between about 0.1 mg/ml and about 0.2 mg/ml.

In some embodiments, the preservative is present in about 0.5% w/w to about 15% w/w of the solids in the oral liquid formulation. In other embodiments, the preservative is present in about 0.5% w/w, about 1% w/w, about 1.5% w/w, about 2% w/w, about 2.5% w/w, about 3% w/w, about 3.5% w/w, about 4% w/w, about 4.5% w/w, about 5% w/w, about 5.5% w/w, about 6% w/w, about 6.5% w/w, about 7% w/w, about 7.5% w/w, about 8% w/w, about 8.5% w/w, about 9% w/w, about 9.5% w/w, about 10% w/w, about 11% w/w, about 11.5% w/w, about 12% w/w, about 12.5% w/w, about 13% w/w, about 13.5% w/w, about 14% w/w, about 14.5% w/w, or about 15% w/w of the solids in the oral liquid formulation.

Sweetener and Preservative Incompatibility

Paraben preservatives (especially methylparaben) can react with selected sugars (glucose, fructose, sucrose, lactose, maltose) and sugar alcohols (xylitol, mannitol, lactitol, maltitol, sorbitol) to form transesterification reaction products. This can be undesirable from a formulation and stability standpoint as the transesterification creates additional degradants.

In some embodiments, the amlodipine oral liquid formulation described herein does not comprise a paraben preservative. In further embodiments, the amlodipine oral liquid formulation described herein does not comprise a paraben preservative when the formulation also comprises a sugar or sugar alcohol.

Buffers in the Amlodipine Oral Liquid Formulations

Buffering agents maintain the pH of the liquid amlodipine formulation. Non-limiting examples of buffering agents include, but are not limited to sodium bicarbonate, potassium bicarbonate, magnesium hydroxide, magnesium lactate, magnesium gluconate, aluminum hydroxide, aluminum hydroxide/sodium bicarbonate co-precipitate, mixture of an amino acid and a buffer, a mixture of aluminum glycinate and a buffer, a mixture of an acid salt of an amino acid and a buffer, and a mixture of an alkali salt of an amino acid and a buffer. Additional buffering agents include citric acid, sodium citrate, sodium tartrate, sodium acetate, sodium carbonate, phosphoric acid, sodium polyphosphate, potassium polyphosphate, sodium pyrophosphate, potassium pyrophosphate, disodium hydrogenphosphate, dipotassium hydrogenphosphate, trisodium phosphate, tripotassium phosphate, sodium acetate, potassium metaphosphate, magnesium oxide, magnesium hydroxide, magnesium carbonate, magnesium silicate, calcium acetate, calcium glycerophosphate, calcium chloride, calcium hydroxide, calcium lactate, calcium carbonate, calcium bicarbonate, and other calcium salts.

In some embodiments, the oral liquid formulation comprises a buffer. In some embodiments, the oral liquid formulation comprises a citrate buffer. In some embodiments, the buffer in the amlodipine oral liquid formulation described herein comprises citric acid. In some embodiments, the buffer in the amlodipine oral liquid formulation described herein comprises citric acid and sodium citrate. In some embodiments, the sodium citrate is monosodium citrate. In some embodiments, the sodium citrate is disodium citrate. In some embodiments, the sodium citrate is trisodium citrate. In some embodiments, the oral liquid formulation comprises a phosphate buffer. In some embodiments, the buffer in the amlodipine oral liquid formulation described herein comprises phosphoric acid. In some embodiments, the buffer in the amlodipine oral liquid formulation described herein comprises phosphoric acid and sodium phosphate. In some embodiments, the buffer in the amlodipine oral liquid formulation described herein comprises sodium phosphate. In some embodiments, the sodium phosphate is sodium dihydrogen phosphate. In some embodiments, the sodium phosphate is sodium hydrogenphosphate. In some embodiments, the sodium phosphate is trisodium phosphate.

In some embodiments, the pH of the amlodipine oral liquid formulation described herein is between about 3 and about 8. In some embodiments, the pH of the amlodipine oral liquid formulation described herein is between about 4 and about 5. In some embodiments, the pH of the amlodipine oral liquid formulation described herein is between about 5 and about 6. In some embodiments, the pH of the amlodipine oral liquid formulation described herein is less than about 4, less than about 4.5, less than about 5, less than about 5.5, less than about 6, less than about 6.5, less than about 7, less than about 7.5, or less than about 8. In some embodiments, the pH of the amlodipine oral liquid formulation described herein is about 3, about 3.1, about 3.2, about 3.3, about 3.4, about 3.5, about 3.6, about 3.7, about 3.8, about 3.9, about 4, about 4.1, about 4.2, about 4.3, about 4.4, about 4.5, about 4.6, about 4.7, about 4.8, about 4.9, about 5, about 5.1, about 5.2, about 5.3, about 5.4, about 5.5, about 5.6, about 5.7, about 5.8, about 5.9, about 6, about 6.1, about 6.2, about 6.3, about 6.4, about 6.5, about 6.6, about 6.7, about 6.8, about 6.9, about 7, about 7.1, about 7.2, about 7.3, about 7.4, about 7.5, about 7.6, about 7.7, about 7.8, about 7.9, or about 8.

In some embodiments, the buffer concentration is between about 1 mM and about 60 mM. In some embodiments, the buffer concentration is about 1 mM, about 1.5 mM, about 2 mM, about 2.5 mM, about 3 mM, about 3.5 mM, about 4 mM, about 4.5 mM, about 5 mM, about 5.5 mM, about 6 mM, about 6.5 mM, about 7 mM, about 7.5 mM, about 8 mM, about 8.5 mM, about 9 mM, about 9.5 mM, about 10 mM, about 10.5 mM, about 11 mM, about 11.5 mM, about 12 mM, about 12.5 mM, about 13 mM, about 13.5 mM, about 14 mM, about 14.5 mM, about 15 mM, about 15.5 mM, about 16 mM, about 16.5 mM, about 17 mM, about 17.5 mM, about 18 mM, about 18.5 mM, about 19 mM, about 19.5 mM, about 20 mM, about 20.5 mM, about 21 mM, about 21.5 mM, about 22 mM, about 22.5 mM, about 23 mM, about 23.5 mM, about 24 mM, about 24.5 mM, about 25 mM, about 25.5 mM, about 26 mM, about 26.5 mM, about 27 mM, about 27.5 mM, about 28 mM, about 28.5 mM, about 29 mM, about 29.5 mM, about 30 mM, about 30.5 mM, about 31 mM, about 31.5 mM, about 32 mM, about 32.5 mM, about 33 mM, about 33.5 mM, about 34 mM, about 34.5 mM, about 35 mM, about 35.5 mM, about 36 mM, about 36.5 mM, about 37 mM, about 37.5 mM, about 38 mM, about 38.5 mM, about 39 mM, about 39.5 mM, about 40 mM, about 40.5 mM, about 41 mM, about 41.5 mM, about 42 mM, about 42.5 mM, about 43 mM, about 43.5 mM, about 44 mM, about 44.5 mM, about 45 mM, about 45.5 mM, about 46 mM, about 46.5 mM, about 47 mM, about 47.5 mM, about 48 mM, about 48.5 mM, about 49 mM, about 49.5 mM, about 50 mM, about 50.5 mM, about 51 mM, about 51.5 mM, about 52 mM, about 52.5 mM, about 53 mM, about 53.5 mM, about 54 mM, about 54.5 mM, about 55 mM, about 55.5 mM, about 56 mM, about 56.5 mM, about 57 mM, about 57.5 mM, about 58 mM, about 58.5 mM, about 59 mM, about 59.5 mM, or about 60 mM. In some embodiments, the buffer concentration is between about 1 mM and about 5 mM, or about 2 mM and about 4 mM. In some embodiments, the buffer concentration is about 3 mM.

In some embodiments, the buffer in the amlodipine oral liquid formulation described herein comprises citric acid. In some embodiments, citric acid is present in about 0.1 mg/ml to about 1.0 mg/ml in the oral liquid formulation. In other embodiments, citric acid is present in about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, or about 1.0 mg/ml in the oral liquid formulation. In one embodiment, citric acid is present in about 0.31 mg/ml in the oral liquid formulation. In some embodiments, citric acid is present in about 5.0 mg/ml to about 15 mg/ml in the oral liquid formulation. In other embodiments, citric acid is present in about 5.0 mg/ml, about 5.5 mg/ml, about 6.0 mg/ml, about 6.5 mg/ml, about 7.0 mg/ml, about 7.5 mg/ml, about 8.0 mg/ml, about 8.5 mg/ml, about 9.0 mg/ml, about 9.5 mg/ml, about 10.0 mg/ml, about 10.5 mg/ml, about 11.0 mg/ml, about 11.5 mg/ml, about 12.0 mg/ml, about 12.5 mg/ml, about 13.0 mg/ml, about 13.5 mg/ml, about 14.0 mg/ml, about 14.5 mg/ml, or about 15.0 mg/ml in the oral liquid formulation.

In some embodiments, citric acid is present in about 1% w/w to about 45% w/w of the solids in the oral liquid formulation. In other embodiments, citric acid is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, about 40% w/w, about 41% w/w, about 42% w/w, about 43% w/w, about 44% w/w, or about 45% w/w of the solids in the oral liquid formulation. In some embodiments, citric acid is present in about 1% w/w to about 20% w/w of the solids in the oral liquid formulation. In some embodiments, citric acid is present in about 1% w/w to about 1.5% w/w of the solids in the oral liquid formulation.

In some embodiments, the amlodipine oral liquid formulation further comprises sodium citrate. In some embodiments, sodium citrate is present in about 0.1 mg/ml to about 1.0 mg/ml in the oral liquid formulation. In other embodiments, sodium citrate is present in the oral liquid formulation is about 0.1 mg/ml, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, or about 1.0 mg/ml in the oral liquid formulation. In one embodiment, sodium citrate is present in about 0.36 mg/ml in the oral liquid formulation.

In some embodiments, sodium citrate is present in about 1% w/w to about 20% w/w of the solids in the oral liquid formulation. In other embodiments, sodium citrate is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 6% w/w, about 7% w/w, about 8% w/w, about 9% w/w, about 10% w/w, about 11% w/w, about 12% w/w, about 13% w/w, about 14% w/w, about 15% w/w, about 16% w/w, about 17% w/w, about 18% w/w, about 19% w/w, or about 20% w/w of the solids in the oral liquid formulation. In some embodiments, sodium citrate is present in about 1% w/w to about 2% w/w of the solids in the oral liquid formulation.

In other embodiments, sodium citrate is not added to the formulation.

In some embodiments, the buffer in the amlodipine oral liquid formulation described herein comprises phosphoric acid. In some embodiments, phosphoric acid is present in about 0.1 mg/ml to about 2.0 mg/ml in the oral liquid formulation. In other embodiments, phosphoric acid is present in about 0.1 mg/ml, about 0.15 mg/ml, about 0.2 mg/ml, about 0.25 mg/ml, about 0.3 mg/ml, about 0.35 mg/ml, 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, about 1.0 mg/ml, about 1.1 mg/ml, about 1.15 mg/ml, about 1.2 mg/ml, about 1.25 mg/ml, about 1.3 mg/ml, about 1.35 mg/ml, about 1.4 mg/ml, about 1.45 mg/ml, about 1.5 mg/ml, about 1.55 mg/ml, about 1.6 mg/mL, about 1.65 mg/mL, about 1.7 mg/ml, about 1.75 mg/ml, about 1.8 mg/ml, about 1.85 mg/ml, about 1.9 mg/ml, about 1.95 mg/ml, or about 2.0 mg/ml in the oral liquid formulation.

In some embodiments, phosphoric acid is present in about 1% w/w to about 10% w/w of the solids in the oral liquid formulation. In other embodiments, citric acid is present in about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, about 7% w/w, about 7.1% w/w, about 7.2% w/w, about 7.3% w/w, about 7.4% w/w, about 7.5% w/w, about 7.6% w/w, about 7.7% w/w, about 7.8% w/w, about 7.9% w/w, about 8% w/w, about 8.1% w/w, about 8.2% w/w, about 8.3% w/w, about 8.4% w/w, about 8.5% w/w, about 8.6% w/w, about 8.7% w/w, about 8.8% w/w, about 8.9% w/w, about 9% w/w, about 9.1% w/w, about 9.2% w/w, about 9.3% w/w, about 9.4% w/w, about 9.5% w/w, about 9.6% w/w, about 9.7% w/w, about 9.8% w/w, about 9.9% w/w, or about 10% w/w of the solids in the oral liquid formulation.

In some embodiments, the buffer in the amlodipine oral liquid formulation described herein comprises sodium hydrogenphosphate. In some embodiments, sodium hydrogenphosphate is present in about 0.1 mg/ml to about 1.0 mg/ml in the oral liquid formulation. In other embodiments, sodium hydrogenphosphate is present in the oral liquid formulation is about 0.1 mg/mL, about 0.11 mg/ml, about 0.12 mg/ml, about 0.13 mg/ml, about 0.14 mg/ml, about 0.15 mg/ml, about 0.16 mg/ml, about 0.17 mg/ml, about 0.18 mg/ml, about 0.19 mg/ml, about 0.2 mg/ml, about 0.21 mg/ml, about 0.22 mg/ml, about 0.23 mg/ml, about 0.24 mg/ml, about 0.25 mg/ml, about 0.26 mg/ml, about 0.27 mg/ml, about 0.28 mg/ml, about 0.29 mg/ml, about 0.3 mg/ml, about 0.31 mg/ml, about 0.32 mg/ml, about 0.33 mg/ml, about 0.34 mg/ml, about 0.35 mg/ml, about 0.36 mg/ml, about 0.37 mg/ml, about 0.38 mg/ml, about 0.39 mg/ml, about 0.4 mg/ml, about 0.41 mg/ml, about 0.42 mg/ml, about 0.43 mg/ml, about 0.44 mg/ml, about 0.45 mg/ml, about 0.46 mg/ml, about 0.47 mg/ml, about 0.48 mg/ml, about 0.49 mg/ml, about 0.5 mg/ml, about 0.51 mg/ml, about 0.52 mg/ml, about 0.53 mg/ml, about 0.54 mg/ml, about 0.55 mg/ml, about 0.56 mg/ml, about 0.57 mg/ml, about 0.58 mg/ml, about 0.59 mg/ml, about 0.6 mg/ml, about 0.61 mg/ml, about 0.62 mg/ml, about 0.63 mg/ml, about 0.64 mg/ml, about 0.65 mg/ml, about 0.66 mg/ml, about 0.67 mg/ml, about 0.68 mg/ml, about 0.69 mg/ml, about 0.7 mg/ml, about 0.71 mg/ml, about 0.72 mg/ml, about 0.73 mg/ml, about 0.74 mg/ml, about 0.75 mg/ml, about 0.76 mg/ml, about 0.77 mg/ml, about 0.78 mg/ml, about 0.79 mg/ml, about 0.8 mg/ml, about 0.81 mg/ml, about 0.82 mg/ml, about 0.83 mg/ml, about 0.84 mg/ml, about 0.85 mg/ml, about 0.86 mg/ml, about 0.87 mg/ml, about 0.88 mg/ml, about 0.89 mg/ml, about 0.9 mg/ml, about 0.91 mg/ml, about 0.92 mg/ml, about 0.93 mg/ml, about 0.94 mg/ml, about 0.95 mg/ml, about 0.96 mg/ml, about 0.97 mg/ml, about 0.98 mg/ml, about 0.99 mg/ml, or about 1.0 mg/ml in the oral liquid formulation.

In some embodiments, sodium hydrogenphosphate is present in about 0.5% w/w to about 5% w/w of the solids in the oral liquid formulation. In other embodiments, sodium hydrogenphosphate is present in about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, or about 5% w/w of the solids in the oral liquid formulation.

Suspension Aid in the Amlodipine Oral Liquid Formulations

A suspension aid or dispersion aid is used to prevent the settling of the pharmaceutically acceptable salt of amlodipine in the oral liquid formulation.

Suitable suspension aids include but not limited to polymers such as 3-butoxy-2-hydroxypropylhydroxyethylcellulose, acrylamide homo- and copolymers, acrylic acid homo- and copolymer, alginates, carboxymethylcellulose (sodium and other salts), carboxymethylhydroxyethylcellulose, carboxy-vinyl copolymers, cellulose, such as microcrystalline cellulose, combinations of microcrystalline cellulose with carboxymethylcellulose sodium (such as Avicel® RC-501, RC-581, RC-591, and CL-611), hydrophobically modified hydroxyethylcellulose, hydroxyethylcellulose, hydroxypropyl guar, hydroxypropyl methylcellulose (such as Benecel K750® or Benecel K1500®), hydroxypropylcellulose, methyl cellulose, natural gums and their derivatives, xanthan gum, guar gum, gum Arabic, partially and fully hydrolyzed polyvinyl alcohols, partially neutralized polyacrylic acid, polyalkylene glycol, polysaccharide gums, polyvinylpyrrolidone and derivatives thereof, starch and its derivatives, vinylpyrrolidone homo- and copolymers, water-soluble cellulose ethers, and the mixtures thereof. Other suitable suspension aids include silicon dioxide, silica powder prepared by precipitating water glass (sodium silicate) with sulfuric acid, which is then dried and sold as a fine powder, fumed alumina (made of primary particles which sinter together to form aggregates), clays such as bentonite, laponites, kaolinite, dickite, and nacrite, pyrophylite, talc, vermiculite, sauconite, saponte, nontronite, and montmorillonite, and organically modified montmorillonite clays. In some embodiments, the suspension aid comprises silicon dioxide. In some embodiment, the silicon dioxide is colloidal silicon dioxide.

In some embodiments, the amlodipine oral liquid formulation described herein comprises a suspension aid. In some embodiments, the suspension aid comprises silicon dioxide, hydroxypropyl methylcellulose, methylcellulose, microcrystalline cellulose, polyvinylpyrrolidone, or combinations thereof. In some embodiments, the suspension aid is silicon dioxide. In some embodiments, the suspension aid is hydroxypropyl methylcellulose. In some embodiments, the suspension aid is a combination of silicon dioxide and hydroxypropyl methylcellulose. In some embodiments, the suspension aid is polyvinylpyrrolidone.

In some embodiments, the suspension aid is present in about 0.1 mg/ml to about 1.0 mg/ml in the oral liquid formulation. In other embodiments, the suspension aid is present in about 0.1 mg/ml, about 0.15 mg/ml, about 0.2 mg/ml, about 0.25 mg/ml, about 0.3 mg/ml, about 0.35 mg/ml, about 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, or about 1.0 mg/ml in the oral liquid formulation. In some embodiments, the suspension aid is present in about 0.3 mg/ml to about 0.7 mg/ml in the oral liquid formulation.

In some embodiments, the suspension aid is present in about 0.4 mg/ml to about 0.6 mg/ml in the oral liquid formulation. In some embodiments, the suspension aid is silicon dioxide and is present in about 0.5 mg/ml in the oral liquid formulation.

In some embodiments, the suspension aid is present in about 3.0 mg/ml to about 10.0 mg/ml in the oral liquid formulation. In other embodiments, the suspension aid is present in about 3.0 mg/ml, about 3.1 mg/ml, about 3.2 mg/ml, about 3.3 mg/ml, about 3.4 mg/ml, about 3.5 mg/ml, about 3.6 mg/ml, about 3.7 mg/ml, about 3.8 mg/ml, about 3.9 mg/ml, about 4.0 mg/ml, about 4.1 mg/ml, about 4.2 mg/ml, about 4.3 mg/ml, about 4.4 mg/ml, about 4.5 mg/ml, about 4.6 mg/ml, about 4.7 mg/ml, about 4.8 mg/ml, about 4.9 mg/ml, about 5.0 mg/ml, about 5.1 mg/ml, about 5.2 mg/ml, about 5.3 mg/ml, about 5.4 mg/ml, about 5.5 mg/ml, about 5.6 mg/ml, about 5.7 mg/ml, about 5.8 mg/ml, about 5.9 mg/ml, about 6.0 mg/ml, about 6.1 mg/ml, about 6.2 mg/ml, about 6.3 mg/ml, about 6.4 mg/ml, about 6.5 mg/ml, about 6.6 mg/ml, about 6.7 mg/ml, about 6.8 mg/ml, about 6.9 mg/ml, about 7.0 mg/ml, about 7.1 mg/ml, about 7.2 mg/ml, about 7.3 mg/ml, about 7.4 mg/ml, about 7.5 mg/ml, about 7.6 mg/ml, about 7.7 mg/ml, about 7.8 mg/ml, about 7.9 mg/ml, about 8.0 mg/ml, about 8.1 mg/ml, about 8.2 mg/ml, about 8.3 mg/ml, about 8.4 mg/ml, about 8.5 mg/ml, about 8.6 mg/ml, about 8.7 mg/ml, about 8.8 mg/ml, about 8.9 mg/ml, about 9.0 mg/ml, about 9.1 mg/ml, about 9.2 mg/ml, about 9.3 mg/ml, about 9.4 mg/ml, about 9.5 mg/ml, about 9.6 mg/ml, about 9.7 mg/ml, about 9.8 mg/ml, about 9.9 mg/ml, or about 10.0 mg/ml in the oral liquid formulation. In some embodiments, the suspension aid is present in about 4.0 mg/ml to about 6.0 mg/ml in the oral liquid formulation. In some embodiments, the suspension aid is present in about 6.0 mg/ml to about 8.0 mg/ml in the oral liquid formulation. In some embodiments, the suspension aid is hydroxypropyl methyl cellulose and is present in about 5.0 mg/ml in the oral liquid formulation. In some embodiments, the suspension aid is hydroxypropyl methyl cellulose and is present in about 7.5 mg/ml in the oral liquid formulation. In some embodiments, the suspension aid is hydroxypropyl methyl cellulose and is present in about 10 mg/ml in the oral liquid formulation.

In some embodiments, the suspension aid is present in about 10 mg/ml to about 30 mg/ml in the oral liquid formulation. In other embodiments, the suspension aid is present in about 10 mg/ml, about 11 mg/ml, about 12 mg/ml, about 13 mg/ml, about 14 mg/ml, about 15 mg/ml, about 16 mg/ml, about 17 mg/ml, about 18 mg/ml, about 19 mg/ml, about 20 mg/ml, about 21 mg/ml, about 22 mg/ml, about 23 mg/ml, about 24 mg/ml, about 25 mg/ml, about 26 mg/ml, about 27 mg/ml, about 28 mg/ml, about 29 mg/ml, or about 30 mg/ml in the oral liquid formulation. In some embodiments, the suspension aid is polyvinylpyrrolidone and is present in about 10 mg/ml in the oral liquid formulation. In some embodiments, the suspension aid is polyvinylpyrrolidone and is present in about 20 mg/ml in the oral liquid formulation. In some embodiments, the suspension aid is polyvinylpyrrolidone and is present in about 30 mg/ml in the oral liquid formulation.

In some embodiments, the suspension aid is present in about 5 mg/ml to about 15 mg/ml in the oral liquid formulation. In other embodiments, the suspension aid is present in about 5.0 mg/ml, about 5.5 mg/ml, about 6.0 mg/ml, about 6.5 mg/ml, about 7.0 mg/ml, about 7.5 mg/ml, about 8 mg/ml, about 8.5 mg/ml, about 9 mg/ml, about 9.5 mg/ml, about 10 mg/ml, about 10.5 mg/ml, about 11 mg/ml, about 11.5 mg/ml, about 12 mg/ml, about 12.5 mg/ml, about 13 mg/ml, about 13.5 mg/ml, about 14 mg/ml, about 14.5 mg/ml, or about 15 mg/ml in the oral liquid formulation. In some embodiments, the suspension aid is Avicel® RC-591 and is present in about 5 mg/ml in the oral liquid formulation. In some embodiments, the suspension aid is Avicel® RC-591 and is present in about 7.5 mg/ml in the oral liquid formulation. In some embodiments, the suspension aid is Avicel® RC-591 and is present in about 10 mg/ml in the oral liquid formulation. In some embodiments, the suspension aid is Avicel⍴ RC-591 and is present in about 15 mg/ml in the oral liquid formulation.

In some embodiments, the suspension aid is present in about 0.4% w/w to about 6% w/w of the solids in the oral liquid formulation. In other embodiments, the suspension aid is present in about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, or about 6% w/w of the solids in the oral liquid formulation.

In some embodiments, the suspension aid is present in about 20% w/w to about 50% w/w of the solids in the oral liquid formulation. In other embodiments, the suspension aid is present in about 20% w/w, about 20.5% w/w, about 21% w/w, about 21.5% w/w, about 22% w/w, about 22.5% w/w, about 23% w/w, about 23.5% w/w, about 24% w/w, about 24.5% w/w, about 25% w/w, about 25.5% w/w, about 26% w/w, about 26.5% w/w, about 27% w/w, about 27.5% w/w, about 28% w/w, about 28.5% w/w, about 29% w/w, about 29.5% w/w, about 30% w/w, about 30.5% w/w, about 31% w/w, about 31.5% w/w, about 32% w/w, about 32.5% w/w, about 33% w/w, about 33.5% w/w, about 34% w/w, about 34.5% w/w, about 35% w/w, about 35.5% w/w, about 36% w/w, about 36.5% w/w, about 37% w/w, about 37.5% w/w, about 38% w/w, about 38.5% w/w, about 39% w/w, about 39.5% w/w, about 40% w/w, about 41% w/w, about 41.5% w/w, about 42% w/w, about 42.5% w/w, about 43% w/w, about 43.5% w/w, about 44% w/w, about 44.5% w/w, about 45% w/w, about 45.5% w/w, about 46% w/w, about 46.5% w/w, about 47% w/w, about 47.5% w/w, about 48% w/w, about 48.5% w/w, about 49% w/w, about 39.5% w/w, or about 50% w/w of the solids in the oral liquid formulation.

In some embodiments, the suspension aid is present in about 40% w/w to about 85% w/w of the solids in the oral liquid formulation. In other embodiments, the suspension aid is present in about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, about 55% w/w, about 56% w/w, about 57% w/w, about 58% w/w, about 59% w/w, about 60% w/w, about 61% w/w, about 62% w/w, about 63% w/w, about 64% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, or about 85% w/w of the solids in the oral liquid formulation.

In some embodiments, the suspension aid is present in about 35% w/w to about 55% w/w of the solids in the oral liquid formulation. In other embodiments, the suspension aid is present in about 35% w/w, about 36% w/w, about 37% w/w, about 38% w/w, about 39% w/w, about 40% w/w, about 41% w/w, about 42% w/w, about 43% w/w, about 44% w/w, about 45% w/w, about 46% w/w, about 47% w/w, about 48% w/w, about 49% w/w, about 50% w/w, about 51% w/w, about 52% w/w, about 53% w/w, about 54% w/w, or about 55% w/w of the solids in the oral liquid formulation.

Antifoaming Agent in the Amlodipine Oral Liquid Formulations

Antifoaming agents are chemical additives that reduce and hinder the formation of foam in the preparation of an oral liquid formulation. The terms antifoaming agent and defoamer are often used interchangeably. Commonly used agents are insoluble oils, polydimethylsiloxanes (e.g., simethicone) and other silicones, certain alcohols, stearates and glycols. Simethicone is available as a pure material (100%) and in combination with other excipients to facilitate dispersion and handling. Common simethicone containing products include NuSil MED-342 (30% w/w simethicone, solid), NuSil Med-340, Med-346, and Med-347 (100% silicone, liquid), Dow Corning® Q7-2587, 7-9245, and Medical Antifoam C (30% Simethicone Emulsion). The additive is used to prevent formation of foam or is added to break foam already formed. Antifoaming agents reduce foaming in the preparation of an oral liquid formulation which can result in coagulation of aqueous dispersions.

In some embodiments, the amlodipine oral liquid formulation described herein comprises an antifoaming agent. In some embodiments, the antifoaming agent is simethicone.

In some embodiments, the antifoaming agent is present in about 0.05 mg/ml to about 1.0 mg/ml in the oral liquid formulation. In other embodiments, the antifoaming agent is present in about 0.05 mg/ml, about 0.1 mg/ml, about 0.15 mg/ml, about 0.2 mg/ml, about 0.25 mg/ml, about 0.3 mg/ml, about 0.35 mg/ml, about 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, or about 1.0 mg/ml in the oral liquid formulation. In some embodiments, the antifoaming agent is present in about 0.05 mg/ml to about 0.3 mg/ml in the oral liquid formulation. In some embodiments, the antifoaming agent is present in about 0.1 mg/ml to about 0.2 mg/ml in the oral liquid formulation. In some embodiments, the antifoaming agent is simethicone and is present in about 0.15 mg/ml in the oral liquid formulation.

In some embodiments, the antifoaming agent is present in about 0.1% w/w to about 7% w/w of the solids in the oral liquid formulation. In other embodiments, the antifoaming agent is present in about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4% w/w, about 4.1% w/w, about 4.2% w/w, about 4.3% w/w, about 4.4% w/w, about 4.5% w/w, about 4.6% w/w, about 4.7% w/w, about 4.8% w/w, about 4.9% w/w, about 5% w/w, about 5.1% w/w, about 5.2% w/w, about 5.3% w/w, about 5.4% w/w, about 5.5% w/w, about 5.6% w/w, about 5.7% w/w, about 5.8% w/w, about 5.9% w/w, about 6% w/w, about 6.1% w/w, about 6.2% w/w, about 6.3% w/w, about 6.4% w/w, about 6.5% w/w, about 6.6% w/w, about 6.7% w/w, about 6.8% w/w, about 6.9% w/w, or about 7% w/w of the solids in the oral liquid formulation.

Surfactants in the Amlodipine Oral Liquid Formulations

Surfactants are compounds that lower the surface tension (or interfacial tension) between two liquids or between a liquid and a solid. Most commonly, surfactants are classified according to polar head group. A non-ionic surfactant has no charged groups in its head. The head of an ionic surfactant carries a net positive, or negative charge. If the charge is negative, the surfactant is more specifically called anionic; if the charge is positive, it is called cationic. If a surfactant contains a head with two oppositely charged groups, it is termed zwitterionic. Anionic surfactants contain anionic functional groups at their head, such as sulfate, sulfonate, phosphate, and carboxylates. Prominent alkyl sulfates include ammonium lauryl sulfate, sodium lauryl sulfate (sodium dodecyl sulfate, SLS, or SDS), and the related alkyl-ether sulfates sodium laureth sulfate (sodium lauryl ether sulfate or SLES), and sodium myreth sulfate. Others include: docusate (dioctyl sodium sulfosuccinate), perfluorooctanesulfonate (PFOS), perfluorobutanesulfonate, alkylaryl ether phosphates, alkyl ether phosphates. Cationic surfactant include pH-dependent primary, secondary, or tertiary amines such as octenidine dihydrochloride; and permanently charged quaternary ammonium salts such as cetrimonium bromide (CTAB), cetylpyridinium chloride (CPC), benzalkonium chloride (BAC), benzethonium chloride (BZT), dimethyldioctadecylammonium chloride, and dioctadecyldimethylammonium bromide (DODAB). Zwitterionic (amphoteric) surfactants have both cationic and anionic centers attached to the same molecule. The cationic part is based on primary, secondary, or tertiary amines or quaternary ammonium cations. The anionic part can be more variable and include sulfonates, as in the sultaines CHAPS (3-[(3-cholamidopropyl)dimethylammonio]-1-propane-sulfonate) and cocamidopropyl hydroxysultaine. Betaines such as cocamidopropyl betaine have a carboxylate with the ammonium. The most common biological zwitterionic surfactants have a phosphate anion with an amine or ammonium, such as the phospholipids phosphatidylserine, phosphatidylethanolamine, phosphatidylcholine, and sphingomyelins. Nonionic surfactants include fatty alcohols, cetyl alcohol, stearyl alcohol, and cetostearyl alcohol, and oleyl alcohol. Also used as nonionic surfactants are polyethylene glycol alkyl ethers (such as octaethylene glycol monododecyl ether, pentaethylene glycol monododecyl ether), polypropylene glycol alkyl ethers, glucoside alkyl ethers (such as decyl glucoside, lauryl glucoside, octyl glucoside), polyethylene glycol octylphenyl ethers (such as Triton X-100), polyethylene glycol alkylphenyl ethers (such as nonoxynol-9), glycerol alkyl esters (such as glyceryl laurate), polyoxyethylene glycol sorbitan alkyl esters (such as polysorbate), sorbitan alkyl esters (such as Spans), cocamide MEA, cocamide DEA, dodecyldimethylamine oxide, block copolymers of polyethylene glycol and polypropylene glycol (such as poloxamers), and polyethoxylated tallow amine (POEA). The most commonly used surfactants are fatty acid esters of sorbitan polyethoxylates, i.e. polysorbate 20 and polysorbate 80. The two differ only in the length of the aliphatic chain that imparts hydrophobic character to the molecules, C-12 and C-18, respectively. Polysorbate 80 is more surface-active and has a lower critical micellar concentration than polysorbate 20.

In some embodiments, the amlodipine oral liquid formulation described herein comprises a surfactant. In some embodiments, the surfactant is polysorbate 80. In some embodiments, the amlodipine oral liquid formulation described herein does not comprise a surfactant.

In some embodiments, the surfactant, when present, is present in about 0.1 mg/ml to about 3.0 mg/ml in the oral liquid formulation. In other embodiments, the surfactant, when present, is present in about 0.1 mg/ml, about 0.15 mg/ml, about 0.2 mg/ml, about 0.25 mg/ml, about 0.3 mg/ml, about 0.35 mg/ml, about 0.4 mg/ml, about 0.45 mg/ml, about 0.5 mg/ml, about 0.55 mg/ml, about 0.6 mg/ml, about 0.65 mg/ml, about 0.7 mg/ml, about 0.75 mg/ml, about 0.8 mg/ml, about 0.85 mg/ml, about 0.9 mg/ml, about 0.95 mg/ml, about 1.0 mg/ml, about 1.1 mg/ml, about 1.15 mg/ml, about 1.2 mg/ml, about 1.25 mg/ml, about 1.3 mg/ml, about 1.35 mg/ml, about 1.4 mg/ml, about 1.45 mg/ml, about 1.5 mg/ml, about 1.55 mg/ml, about 1.6 mg/ml, about 1.65 mg/ml, about 1.7 mg/ml, about 1.75 mg/ml, about 1.8 mg/ml, about 1.85 mg/ml, about 1.9 mg/ml, about 1.95 mg/ml, about 2.0 mg/ml, about 2.1 mg/ml, about 2.15 mg/ml, about 2.2 mg/ml, about 2.25 mg/ml, about 2.3 mg/ml, about 2.35 mg/ml, about 2.4 mg/ml, about 2.45 mg/ml, about 2.5 mg/ml, about 2.55 mg/ml, about 2.6 mg/ml, about 2.65 mg/ml, about 2.7 mg/ml, about 2.75 mg/ml, about 2.8 mg/ml, about 2.85 mg/ml, about 2.9 mg/ml, about 2.95 mg/ml, or about 3.0 mg/ml in the oral liquid formulation. In some embodiments, the surfactant, when present, is polysorbate 80 and is present in about 0.5 mg/ml in the oral liquid formulation. In some embodiments, the surfactant, when present, is polysorbate 80 and is present in about 1.0 mg/ml in the oral liquid formulation. In some embodiments, the surfactant, when present, is polysorbate 80 and is present in about 2.0 mg/ml in the oral liquid formulation.

In some embodiments, the surfactant, when present is present in about 1% w/w to about 15% w/w of the solids in the oral liquid formulation. In other embodiments, the surfactant, when present is present in about 1%, about 1.5%, about 2%, about 2.5%, about 3%, about 3.5%, about 4%, about 4.5%, about 5%, about 5.5%, about 6%, about 6.5%, about 7%, about 7.5%, about 8%, about 8.5%, about 9%, about 9.5%, about 10%, about 10.5%, about 11%, about 11.5%, about 12%, about 12.5%, about 13%, about 13.5%, about 14%, about 14.5%, or about 15% of the solids in the oral liquid formulation.

In some embodiments, the surfactant, when present is present in about 1% w/w to about 5% w/w of the solids in the oral liquid formulation. In other embodiments, the surfactant, when present is present in about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5% of the solids in the oral liquid formulation.

Additional Excipients

In further embodiments, the amlodipine oral liquid formulation described herein comprises additional excipients including, but not limited to flavoring agents, coloring agents and thickeners. Additional excipients such as bulking agents, tonicity agents and chelating agents are within the scope of the embodiments.

In another embodiment, the amlodipine oral liquid formulation comprises a flavoring agent or flavorant to enhance the taste or aroma of the formulation in liquid form. Suitable natural or synthetic flavoring agents can be selected from standard reference books, for example Fenaroli's Handbook of Flavor Ingredients, 3rd edition (1995). Non-limiting examples of suitable natural flavors, some of which can readily be simulated with synthetic agents or combinations thereof, include almond, anise, apple, apricot, bergamot, blackberry, blackcurrant, blueberry, cacao, caramel, cherry, cinnamon, clove, coffee, coriander, cranberry, cumin, dill, eucalyptus, fennel, fig, ginger, grape, grapefruit, guava, hop, lemon, licorice, lime, malt, mandarin, molasses, nutmeg, mixed berry, orange, peach, pear, peppermint, pineapple, raspberry, rose, spearmint, strawberry, tangerine, tea, vanilla, wintergreen, etc. Also useful, particularly where the formulation is intended primarily for pediatric use, is tutti-frutti or bubblegum flavor, a compounded flavoring agent based on fruit flavors. Presently preferred flavoring agents include anise, cinnamon, cacao, orange, peppermint, cherry (in particular wild cherry), grape, bubblegum, vanilla, and mixed berry. Flavoring agents can be used singly or in combinations of two or more. In certain embodiments, the amlodipine oral liquid formulation comprises a flavoring agent.

In further embodiments, the amlodipine oral liquid formulation comprises a coloring agent for identity and/or aesthetic purposes. Suitable coloring agents illustratively include FD&C Red No. 3, FD&C Red No. 20, FD&C Red No. 40, FD&C Yellow No. 6, FD&C Blue No. 2, FD&C Green No. 5, FD&C Orange No. 5, caramel, ferric oxide and mixtures thereof.

Thickeners impart viscosity or weight to the resultant liquid forms from the amlodipine formulation described herein. Exemplary thickeners include dextrin, cellulose derivatives (carboxymethylcellulose and its salts, ethylcellulose, hydroxyethyl cellulose, methylcellulose, hypromellose, and the like) starches, pectin, polyethylene glycol, polyethylene oxide, trehalose, certain silicates (magnesium aluminum silicate, aluminum silicate, etc. such as Veegum, Bentonite, and Kaolin) and certain gums (xanthan gum, locust bean gum, etc.). In certain embodiments, the amlodipine oral liquid formulation comprises a thickener.

In further embodiments, the amlodipine liquid formulation does not comprise glycerol which may cause headache, stomach upset, and diarrhea.

Additional excipients are contemplated in the amlodipine oral liquid formulation embodiments. These additional excipients are selected based on function and compatibility with the amlodipine liquid formulations described herein and may be found, for example in *Remington: The Science and Practice of Pharmacy*, Nineteenth Ed (Easton, PA:

Mack Publishing Company, 1995); Hoover, John E., *Remington's Pharmaceutical Sciences*, (Easton, PA: Mack Publishing Co 1975); Liberman, H. A. and Lachman, L., Eds., *Pharmaceutical Dosage Forms* (New York, NY: Marcel Decker 1980); and *Pharmaceutical Dosage Forms and Drug Delivery Systems*, Seventh Ed (Lippincott Williams & Wilkins 1999), herein incorporated by reference in their entirety.

Stability

The amlodipine oral liquid formulations described herein are stable in various storage conditions including refrigerated, ambient and accelerated conditions. Stable as used herein refers to amlodipine oral liquid formulations having about 95% or greater of the initial amlodipine amount and/or about 5% w/w or less total impurities or related substances at the end of a given storage period. In some embodiment, the impurity is amlodipine USP impurity A (A.K.A EP impurity D):

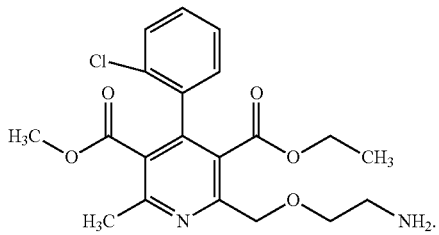 [SMILES: CCOC(=O)c1c(COCCN)nc(C)c(C(=O)OC)c1-c1ccccc1Cl]

The percentage of impurities is calculated from the amount of impurities relative to the amount of amlodipine. Stability is assessed by HPLC or any other known testing method. In some embodiments, the stable amlodipine oral liquid formulations have about 5% w/w, about 4% w/w, about 3% w/w, about 2.5% w/w, about 2% w/w, about 1.5% w/w, about 1% w/w, or about 0.5% w/w total impurities or related substances. In other embodiments, the stable amlodipine oral liquid formulations have about 5% w/w total impurities or related substances. In yet other embodiments, the stable amlodipine oral liquid formulations have about 4% w/w total impurities or related substances. In yet other embodiments, the stable amlodipine oral liquid formulations have about 3% w/w total impurities or related substances. In yet other embodiments, the stable amlodipine oral liquid formulations have about 2% w/w total impurities or related substances. In yet other embodiments, the stable amlodipine oral liquid formulations have about 1% w/w total impurities or related substances.

At refrigerated condition, the amlodipine oral liquid formulations described herein are stable for at least 1 month, at least 2 months, at least 3 months, at least 6 months, at least 9 months, at least 12 months, at least 15 months, at least 18 months, at least 24 months, at least 30 months and at least 36 months. In some embodiments, refrigerated condition is 5±5° C. In some embodiments, refrigerated condition is about 0° C., about 0.1° C., about 0.2° C., about 0.3° C., about 0.4° C., about 0.5° C., about 0.6° C., about 0.7° C., about 0.8° C., about 0.9° C., about 1° C., about 1.1° C., about 1.2° C., about 1.3° C., about 1.4° C., about 1.5° C., about 1.6° C., about 1.7° C., about 1.8° C., about 1.9° C., about 2° C., about 2.1° C., about 2.2° C., about 2.3° C., about 2.4° C., about 2.5° C., about 2.6° C., about 2.7° C., about 2.8° C., about 2.9° C., about 3° C., about 3.1° C., about 3.2° C., about 3.3° C., about 3.4° C., about 3.5° C., about 3.6° C., about 3.7° C., about 3.8° C., about 3.9° C., about 4° C., about 4.1° C., about 4.2° C., about 4.3° C., about 4.4° C., about 4.5° C., about 4.6° C., about 4.7° C., about 4.8° C., about 4.9° C., about 5° C., about 5.1° C., about 5.2° C., about 5.3° C., about 5.4° C., about 5.5° C., about 5.6° C., about 5.7° C., about 5.8° C., about 5.9° C., about 6° C., about 6.1° C., about 6.2° C., about 6.3° C., about 6.4° C., about 6.5° C., about 6.6° C., about 6.7° C., about 6.8° C., about 6.9° C., about 7° C., about 7.1° C., about 7.2° C., about 7.3° C., about 7.4° C., about 7.5° C., about 7.6° C., about 7.7° C., about 7.8° C., about 7.9° C., about 8° C., about 8.1° C., about 8.2° C., about 8.3° C., about 8.4° C., about 8.5° C., about 8.6° C., about 8.7° C., about 8.8° C., about 8.9° C., about 9° C., about 9.1° C., about 9.2° C., about 9.3° C., about 9.4° C., about 9.5° C., about 9.6° C., about 9.7° C., about 9.8° C., about 9.9° C., or about 10° C. At accelerated conditions, the amlodipine oral liquid formulations described herein are stable for at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, or at least 24 months. Accelerated conditions for the amlodipine oral liquid formulations described herein include temperatures that are at or above ambient levels (25±5° C.). In some instances, an accelerated condition is at about 25° C., about 30° C., about 35° C., about 40° C., about 45° C., about 50° C., about 55° C., or about 60° C. Accelerated conditions for the amlodipine oral liquid formulations described herein also include relative humidity (RH) that are at or above ambient levels (55±10% RH). In other instances, an accelerated condition is above 55% RH, about 65% RH, about 70% RH, about 75% RH, or about 80% RH. In further instances, an accelerated condition is about 40° C. or 60° C. at ambient humidity. In yet further instances, an accelerated condition is about 40° C. at 75±5% RH humidity.

In some embodiments, the amlodipine oral liquid formulation is stable between about 5±5° C. and about 25±5° C. for at least 12 months. In one embodiment, the amlodipine oral liquid formulation is stable at about 5±5° C. for at least 12 months. In one embodiment, the amlodipine oral liquid formulation is stable at about 25±5° C. for at least 12 months. In one embodiment, the amlodipine oral liquid formulation is stable at about 5±5° C. for at least 24 months. In one embodiment, the amlodipine oral liquid formulation is stable at about 25±5° C. for at least 24 months.

Kits and Articles of Manufacture

For the amlodipine liquid formulations described herein, kits and articles of manufacture are also described. Such kits can comprise a carrier, package, or container that is compartmentalized to receive one or more containers such as vials, tubes, and the like, each of the container(s) comprising one of the separate elements to be used in a method described herein including an amlodipine liquid formulation. Suitable containers include, for example, bottles, vials, syringes, and test tubes. The containers can be formed from a variety of materials such as glass or plastic.

A kit will typically comprise one or more additional containers, each with one or more of various materials (such as reagents, optionally in concentrated form, and/or devices) desirable from a commercial and user standpoint for an amlodipine liquid formulation described herein. Non-limiting examples of such materials include, but not limited to, buffers, diluents, filters, needles, syringes; carrier, package, container, vial and/or tube labels listing contents and/or instructions for use, and package inserts with instructions for use associated with an amlodipine liquid formulation. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

Method of Manufacturing

Disclosed herein is a process for preparing a stable amlodipine oral liquid formulation. In some embodiments, the stable amlodipine oral liquid formulation is in the form of a suspension. In some embodiments, the stable amlodipine oral liquid formulation comprises a pharmaceutically acceptable salt of amlodipine which is very slightly soluble in an aqueous media. In some embodiments, the stable amlodipine oral liquid formulation comprises a pharmaceutically acceptable salt of amlodipine which is practically insoluble in an aqueous media.

Disclosed herein is a process for preparing a stable amlodipine oral liquid formulation, the process comprising mixing a first mixture with a second mixture; the first mixture comprising: a pharmaceutically acceptable salt of amlodipine; optionally a salt comprising the counter ions from a water soluble salt of amlodipine and a salt forming agent; one or more agent selected from the group consisting of preservatives and surfactants; and water; and the second mixture comprising: a buffer; optionally one or more agents selected from the group consisting of flavoring agents, sweetening agents, suspensions aids, and antifoaming agents; and water. In some embodiments, the first mixture comprises a pharmaceutically acceptable salt of amlodipine; a preservative; a surfactant; and water. In some embodiments, the first mixture comprises a pharmaceutically acceptable amlodipine salt; a preservative; and water. In some embodiments, the first mixture is obtained by a process comprising adding water to a first container; adding a water soluble salt of amlodipine to the first container; adding a salt forming agent to the first container; adding a preservative; optionally adding a surfactant to the first container; and stirring until a new pharmaceutically acceptable salt of amlodipine substantially precipitates. In some embodiments, the second mixture comprises a buffer; optionally a flavoring agent; a sweetening agent; suspensions aids; an antifoaming agent; and water. In some embodiments, the second mixture is obtained by a process comprising adding water to a second container; adding a buffer to a second container; adding a sweetening agent to a second container; optionally adding a flavoring agent to a second container; adding an antifoaming agent to a second container; adding suspension aids to a second container; and stirring. In some embodiments, the preservative is sodium benzoate and the buffer is a citrate buffer. In some embodiments, the preservative is a paraben or a mixture of parabens and the buffer is a phosphate buffer.

Disclosed herein is a process for preparing a stable amlodipine oral liquid formulation, the process comprising mixing a first mixture with a second mixture; the first mixture comprising: amlodipine benzoate; sodium benzoate; optionally sodium besylate; optionally polysorbate 80; and water; and the second mixture comprising: citric acid; sodium citrate; sucralose; optionally a flavoring agent; hydroxypropyl methylcellulose; simethicone; silicon dioxide; and water. In some embodiments, the first mixture is obtained by a process comprising adding water to a first container which is not stainless steel; adding amlodipine besylate to the first container; adding sodium benzoate to the first container; optionally adding polysorbate 80 to the first container; and stirring until amlodipine benzoate substantially precipitates. In some embodiments, the second mixture is obtained by a process comprising adding water to a second container; adding citric acid to the second container; adding sodium citrate to the second container; adding sucralose to the second container; optionally adding a flavoring agent to the second container; adding hydroxypropyl methylcellulose to the second container; adding simethicone to the second container; adding silicon dioxide to the second container; and stirring.

Disclosed herein is a process for preparing a stable amlodipine oral liquid formulation, the process comprising mixing a first mixture with a second mixture; the first mixture comprising: amlodipine benzoate; sodium benzoate; polysorbate 80; optionally sodium besylate; and water; and the second mixture comprising: citric acid; sodium citrate; sucralose; optionally a flavoring agent; hydroxypropyl methylcellulose; simethicone; silicon dioxide; and water. In some embodiments, the first mixture is obtained by a process comprising adding water to a first container which is not stainless steel; adding amlodipine besylate to the first container; adding sodium benzoate to the first container; adding polysorbate 80 to the first container; and stirring until amlodipine benzoate substantially precipitates. In some embodiments, the second mixture is obtained by a process comprising adding water to a second container; adding citric acid to the second container; adding sodium citrate to the second container; adding sucralose to the second container; optionally adding the flavoring agent to the second container; adding hydroxypropyl methylcellulose to the second container; adding simethicone to the second container; adding silicon dioxide to the second container; and stirring.

Disclosed herein is a process for preparing a stable amlodipine oral liquid formulation, the process comprising mixing a first mixture with a second mixture; the first mixture comprising: amlodipine naphthalene sulfonate; sodium benzoate; optionally sodium besylate; optionally polysorbate 80; and water; and the second mixture comprising: citric acid; sodium citrate; sucralose; optionally a flavoring agent; hydroxypropyl methylcellulose; simethicone; silicon dioxide; and water. In some embodiments, the first mixture is obtained by a process comprising adding water to a first container which is not stainless steel; adding amlodipine besylate to the first container; adding sodium naphthalene-2-sulfonate to the first container; adding sodium benzoate to the first container; optionally adding polysorbate 80 to the first container; and stirring until amlodipine naphthalene sulfonate substantially precipitates. In some embodiments, the second mixture is obtained by a process comprising adding water to a second container; adding citric acid to the second container; adding sodium citrate to the second container; adding sucralose to the second container; optionally adding the flavoring agent to the second container; adding hydroxypropyl methylcellulose to the second container; adding simethicone to the second container; adding silicon dioxide to the second container; and stirring. In some embodiments, the first mixture is obtained by a process comprising adding water to a first container which is not stainless steel; adding amlodipine besylate to the first container; adding sodium naphthalene-2-sulfonate to the first container; adding sodium benzoate to the first container; and stirring until amlodipine naphthalene sulfonate substantially precipitates. In some embodiments, the second mixture is obtained by a process comprising adding water to a second container; adding citric acid to the second container; adding sodium citrate to the second container; adding sucralose to the second container; optionally adding the flavoring agent to the second container; adding hydroxypropyl methylcellulose to the second container; adding simethicone to the second container; adding silicon dioxide to the second container; and stirring. In some embodiments, the sodium benzoate is added to the second container. In some embodiments sodium benzoate is not added to the first container.

Disclosed herein is a process for preparing a stable amlodipine oral liquid formulation in a single container.

In some embodiments, the process for preparing a stable amlodipine oral liquid formulation in a single container comprises the formation of a pharmaceutically acceptable salt of amlodipine; followed by addition of one or more agents selected from the group consisting of preservatives, surfactants, flavoring agents, sweetening agents, suspensions aids, and antifoaming agents. In some embodiments, the pharmaceutically acceptable salt of amlodipine is obtained by a process comprising adding water to a container, adding a buffer to the container; adding a water soluble salt of amlodipine to the container; adding a salt forming agent to the container; and stirring until a new pharmaceutically acceptable salt of amlodipine substantially precipitates. The process further comprises cooling the suspension of the new pharmaceutically acceptable salt of amlodipine. The process further comprises adding optional components selected from preservatives, surfactants, flavoring agents, sweetening agents, suspensions aids, and antifoaming agents. In some embodiments, the container is not stainless steel. In some embodiments, high shear mixing is used. In some embodiments, sonication is used.

In some embodiments, the process for preparing a stable amlodipine oral liquid formulation in a single container comprises the formation of a pharmaceutically acceptable salt of amlodipine following the addition of one or more agent selected from the group consisting of buffers, preservatives, surfactants, flavoring agents, sweetening agents, suspensions aids, and antifoaming agents. In some embodiments, process comprises adding water to a container; adding a salt forming agent to the container; optionally adding one or more agent selected from the group consisting of buffers, preservatives, surfactants, flavoring agents, sweetening agents, suspensions aids, and antifoaming agents to the container; adding a water soluble salt of amlodipine to the container; and stirring until a new pharmaceutically acceptable salt of amlodipine substantially precipitates. In some embodiments, the container is not stainless steel.

Methods of Treatment

Provided herein, in one aspect, are methods of treatment comprising administration of the amlodipine oral liquid formulations described herein to a subject. In some embodiments, the amlodipine oral liquid formulations described herein treat hypertension in a subject. Hypertension as used herein includes both primary (essential) hypertension and secondary hypertension. In certain instances, hypertension is classified in cases when blood pressure values are greater than or equal to 140/90 (systolic/diastolic) mm Hg in a subject. In certain instances, the amlodipine oral liquid formulations described herein treat a subject having a blood pressure values are greater than or equal to 140/90 mm Hg.

In certain instances, the amlodipine oral liquid formulations described herein treat primary (essential) hypertension in a subject. In other instances, the amlodipine oral liquid formulations described herein treat secondary hypertension in a subject.

In other embodiments, the amlodipine oral liquid formulations described herein treat prehypertension in a subject. Prehypertension as used herein refers to cases where a subject's blood pressure is elevated above normal but not to the level considered to be hypertension. In some instances, prehypertension is classified in cases when blood pressure values are 120-139/80-89 mm Hg. In certain instances, the amlodipine oral liquid formulations described herein treat a subject having blood pressure values of 120-139/80-89 mm Hg.

In yet other embodiments, the amlodipine oral liquid formulations described herein are prophylactically administered to subjects suspected of having, predisposed to, or at risk of developing hypertension. In some embodiments, the administration of amlodipine oral liquid formulations described herein allow for early intervention prior to onset of hypertension. In certain embodiments, upon detection of a biomarker, environmental, genetic factor, or other marker, the amlodipine oral liquid formulations described herein are prophylactically administered to subjects.

In further embodiments, the amlodipine oral liquid formulations described herein treat Coronary Artery Disease (CAD). In some embodiments, the amlodipine oral liquid formulations described herein treat chronic stable angina. In some embodiments, the amlodipine oral liquid formulations described herein treat vasospastic angina (Prinzmetal's or Variant angina). In some embodiments, the amlodipine oral liquid formulations described herein treat angiographically documented coronary artery disease in patients without heart failure or an ejection fraction<40%.

Dosing

In one aspect, the amlodipine oral liquid formulations are used for the treatment of diseases and conditions described herein. In addition, a method for treating any of the diseases or conditions described herein in a subject in need of such treatment, involves administration of amlodipine oral liquid formulations in therapeutically effective amounts to said subject.

Dosages of amlodipine oral liquid formulations described can be determined by any suitable method. Maximum tolerated doses (MTD) and maximum response doses (MRD) for amlodipine can be determined via established animal and human experimental protocols as well as in the examples described herein. For example, toxicity and therapeutic efficacy of amlodipine can be determined by standard pharmaceutical procedures in cell cultures or experimental animals, including, but not limited to, for determining the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Amlodipine dosages exhibiting high therapeutic indices are of interest. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized. Additional relative dosages, represented as a percent of maximal response or of maximum tolerated dose, are readily obtained via the protocols.

In some embodiments, the amount of a given amlodipine oral liquid formulation that corresponds to such an amount varies depending upon factors such as the particular amlodipine salt or form, disease condition and its severity, the identity (e.g., weight, sex) of the subject or host in need of treatment, but can nevertheless be determined according to the particular circumstances surrounding the case, including, e.g., the specific agent being administered, the liquid composition type, the condition being treated, and the subject or host being treated.

In some embodiments, the amlodipine oral liquid formulations described herein are provided in a dose per day from about 0.01 mg to 100 mg, from about 0.1 mg to about 80 mg, from about 1 to about 60, from about 2 mg to about 40 mg of amlodipine. In certain embodiments, the amlodipine oral liquid formulations described herein are provided in a daily dose of about 0.01 mg, about 0.05 mg, about 0.1 mg, about 0.2 mg, about 0.4 mg, about 0.6 mg, about 0.8 mg, about 1 mg, about 1.5 mg, about 2 mg, about 2.5 mg, about 3 mg, about 4 mg, about 5 mg, about 6 mg, about 7 mg, about 8 mg, about 9 mg, about 10 mg, about 11 mg, about 12 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 76, mg, about 80 mg, about 85 mg, about 90 mg or about 100 mg, or any range derivable therein. In certain instances, the amlodipine oral liquid formulations described herein are provided in a dose per day of about 1 mg. In certain instances, the amlodipine oral liquid formulations described herein are provided in a dose per day of about 2 mg. In certain instances, the amlodipine oral liquid formulations described herein are provided in a dose per day of about 3 mg. In certain instances, the amlodipine oral liquid formulations described herein are provided in a dose per day of about 4 mg. In certain instances, the amlodipine oral liquid formulations described herein are provided in a dose per day of about 5 mg. In certain instances, the amlodipine oral liquid formulations described herein are provided in a dose per day of about 6 mg. In certain instances, the amlodipine oral liquid formulations described herein are provided in a dose per day of about 7 mg. In certain instances, the amlodipine oral liquid formulations described herein are provided in a dose per day of about 8 mg. In certain instances, the amlodipine oral liquid formulations described herein are provided in a dose per day of about 9 mg. In certain instances, the amlodipine oral liquid formulations described herein are provided in a dose per day of about 10 mg. In certain instances, the amlodipine oral liquid formulations described herein are provided in a dose per day of about 11 mg. In certain instances, the amlodipine oral liquid formulations described herein are provided in a dose per day of about 12 mg. The dose per day described herein can be given once per day or multiple times per day in the form of sub-doses given b.i.d., t.i.d., q.i.d., or the like where the number of sub-doses equal the dose per day.

In further embodiments, the daily dosages appropriate for the amlodipine oral liquid formulations described herein are from about 0.01 to about 1.0 mg/kg per body weight. In one embodiment, the daily dosages appropriate for the amlodipine oral liquid formulations are from about 0.02 to about 0.8 mg/kg amlodipine per body weight. In another embodiment, the daily dosage appropriate for the amlodipine oral liquid formulations are from about 0.05 to about 0.6 mg/kg per body weight. In another embodiment, the daily dosage appropriate for the amlodipine oral liquid formulations is about 0.05 mg/kg, about 0.06 mg/kg, about 0.07 mg/kg, about 0.08 mg/kg, about 0.10 mg/kg, about 0.15 mg/kg, about 0.20 mg/kg, about 0.25 mg/kg, about 0.30 mg/kg, about 0.40 mg/kg, about 0.50 mg/kg, or about 0.60 mg/kg.

In other embodiments, the amlodipine oral liquid formulations are provided at the maximum tolerated dose (MTD) for amlodipine. In other embodiments, the amount of the amlodipine oral liquid formulations administered is from about 10% to about 90% of the maximum tolerated dose (MTD), from about 25% to about 75% of the MTD, or about 50% of the MTD. In particular embodiments, the amount of the amlodipine oral liquid formulations administered is from about 5%, 10%, 15%, 20%, 25%, 30%, 35%, 40%, 45%, 50%, 55%, 60%, 65%, 70%, 75%, 80%, 85%, 90%, 95%, 99%, or higher, or any range derivable therein, of the MTD for amlodipine.

In further embodiments, the amlodipine oral liquid formulations are provided in a dosage that is similar, comparable or equivalent to a dosage of a known amlodipine tablet formulation. In other embodiments, the amlodipine oral liquid formulations are provided in a dosage that provides similar, comparable or equivalent pharmacokinetic parameters (e.g., AUC, $C_{max}$, $T_{max}$, $C_{min}$, $T_{1/2}$) as a dosage of a known amlodipine tablet formulation. Similar, comparable or equivalent pharmacokinetic parameters, in some instances, refer to within 80% to 125%, 80% to 120%, 85% to 125%, 90% to 110%, or increments therein, of the given values. It should be recognized that the ranges can, but need not be symmetrical, e.g., 85% to 105%.

Administration

Administration of an amlodipine oral liquid formulation is at a dosage described herein or at other dose levels and formulations determined and contemplated by a medical practitioner. In certain embodiments, the amlodipine oral liquid formulations described herein are administered for prophylactic and/or therapeutic treatments. In certain therapeutic applications, the amlodipine oral liquid formulations are administered to a patient already suffering from a disease, e.g., hypertension, in an amount sufficient to cure the disease or at least partially arrest or ameliorate the symptoms, e.g., lower blood pressure. Amounts effective for this use depend on the severity of the disease, previous therapy, the patient's health status, weight, and response to the amlodipine formulations, and the judgment of the treating physician. Therapeutically effective amounts are optionally determined by methods including, but not limited to, a dose escalation clinical trial.

In prophylactic applications, the amlodipine oral liquid formulations described herein are administered to a patient susceptible to or otherwise at risk of a particular disease, e.g., hypertension. Such an amount is defined to be a "prophylactically effective amount or dose." In this use, the precise amounts also depend on the patient's state of health, weight, and the like. When used in a patient, effective amounts for this use will depend on the risk or susceptibility of developing the particular disease, previous therapy, the patient's health status and response to the amlodipine formulations, and the judgment of the treating physician.

In certain embodiments wherein the patient's condition does not improve, upon the doctor's discretion the administration of an amlodipine oral liquid formulations described herein are administered chronically, that is, for an extended period of time, including throughout the duration of the patient's life in order to ameliorate or otherwise control or limit the symptoms of the patient's disease. In other embodiments, administration of an amlodipine oral liquid formulation continues until complete or partial response of a disease.

In certain embodiments wherein a patient's status does improve, the dose of an amlodipine oral liquid formulation being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In some embodiments, amlodipine oral liquid formulations described herein are administered chronically. For example, in some embodiments, an amlodipine oral liquid formulation is administered as a continuous dose, i.e., administered daily to a subject. In some other embodiments, amlodipine oral liquid formulations described herein are administered intermittently (e.g. drug holiday that includes a period of time in which the formulation is not administered or is administered in a reduced amount).

In some embodiments, the amlodipine oral liquid formulation is administered to a subject who is in a fasted state. A fasted state refers to a subject who has gone without food or fasted for a certain period of time. General fasting periods include at least 4 hours, at least 6 hours, at least 8 hours, at least 10 hours, at least 12 hours, at least 14 hours and at least 16 hours without food. In some embodiments, an amlodipine oral liquid formulation is administered orally to a subject who is in a fasted state for at least 8 hours. In other embodiments, an amlodipine oral liquid formulation is administered to a subject who is in a fasted state for at least 10 hours. In yet other embodiments, an amlodipine oral liquid formulation is administered to a subject who is in a fasted state for at least 12 hours. In other embodiments, an amlodipine oral liquid formulation is administered to a subject who has fasted overnight.

In other embodiments, the amlodipine oral liquid formulation is administered to a subject who is in a fed state. A fed state refers to a subject who has taken food or has had a meal. In certain embodiments, an amlodipine oral liquid formulation is administered to a subject in a fed state 5 minutes post-meal, 10 minutes post-meal, 15 minutes post-meal, 20 minutes post-meal, 30 minutes post-meal, 40 minutes post-meal, 50 minutes post-meal, 1 hour post-meal, or 2 hours post-meal. In certain instances, an amlodipine oral liquid formulation is administered to a subject in a fed state 30 minutes post-meal. In other instances, an amlodipine oral liquid formulation is administered to a subject in a fed state 1 hour post-meal. In yet further embodiments, an amlodipine oral liquid formulation is administered to a subject with food.

In further embodiments described herein, an amlodipine oral liquid formulation is administered at a certain time of day for the entire administration period. For example, an amlodipine oral liquid formulation can be administered at a certain time in the morning, in the evening, or prior to bed. In certain instances, an amlodipine oral liquid formulation is administered in the morning. In other embodiments, an amlodipine oral liquid formulation can be administered at different times of the day for the entire administration period. For example, an amlodipine oral liquid formulation can be administered on 8:00 am in the morning for the first day, 12 pm noon for the next day or administration, 4 pm in the afternoon for the third day or administration, and so on.

Combinations

The treatment of certain diseases or conditions (e.g., hypertension, heart failure, myocardial infarction and the like) in a subject with an amlodipine oral liquid formulation described herein encompass additional therapies and treatment regimens with other agents in some embodiments. Such additional therapies and treatment regimens can include another therapy, e.g., additional anti-hypertensives, for treatment of the particular disease or condition in some embodiments. Alternatively, in other embodiments, additional therapies and treatment regimens include other agents used to treat adjunct conditions associated with the disease or condition or a side effect from the amlodipine oral liquid formulation in the therapy.

Additional agents for use in combination with an amlodipine oral liquid formulation described herein include, but are not limited to, diuretics (loop, thiazide, potassium-sparing, and the like), beta blockers (metoprolol, propanolol, pronethalol, and the like), alpha blockers (phentolamine, phenoxybenzamine, tamsulosin, prazosin, and the like), mixed alpha and beta blockers (bucindolol, carvedilol, labetalol), calcium channel blockers (dihydropyridines such as nifedipine, etc., diltiazem, verapamil and the like), angiotensin II receptor antagonists (saralasin, losartan, eprosartin, irbesartan, valsartan, and the like), other ACE inhibitors (enalapril, captopril, quinapril, ramipril, lisinopril, zofenopril, and the like), aldosterone antagonists (eplerenone, spironolactone and the like), vasodilators (hydralazine and the like) and alpha-2 agonists (clonidine, moxonidine, guanabenz and the like).

Certain Definitions

Unless defined otherwise, all technical and scientific terms used herein have the same meanings as commonly understood by one of ordinary skill in the art. Although any methods and materials similar or equivalent to those described herein can be used in the practice or testing of embodiments described herein, certain preferred methods, devices, and materials are now described.

As used herein and in the appended claims, the singular forms "a", "an", and "the" include plural reference unless the context clearly dictates otherwise. Thus, for example, reference to "an excipient" is a reference to one or more excipients and equivalents thereof known to those skilled in the art, and so forth.

The term "about" is used to indicate that a value includes the standard level of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

"Optional" or "optionally" may be taken to mean that the subsequently described structure, event or circumstance may or may not occur, and that the description includes instances where the events occurs and instances where it does not.

As used herein, the term "therapeutic" means an agent utilized to treat, combat, ameliorate, prevent or improve an unwanted condition or disease of a patient. In some embodiments, a therapeutic agent such as amlodipine is directed to the treatment and/or the amelioration of, reversal of, or stabilization of the symptoms of hypertension described herein.

"Administering" when used in conjunction with a therapeutic means to administer a therapeutic systemically or locally, as directly into or onto a target tissue, or to administer a therapeutic to a patient whereby the therapeutic positively impacts the tissue to which it is targeted. Thus, as used herein, the term "administering", when used in conjunction with an amlodipine formulation, can include, but is not limited to, providing an amlodipine formulation into or onto the target tissue; providing an amlodipine formulation systemically to a patient by, e.g., oral administration whereby the therapeutic reaches the target tissue or cells. "Administering" a formulation may be accomplished by injection, topical administration, and oral administration or by other methods alone or in combination with other known techniques.

The term "animal" as used herein includes, but is not limited to, humans and non-human vertebrates such as wild, domestic and farm animals. As used herein, the terms "patient," "subject" and "individual" are intended to include living organisms in which certain conditions as described herein can occur. Examples include humans, monkeys, cows, sheep, goats, dogs, cats, mice, rats, and transgenic species thereof. In a preferred embodiment, the patient is a primate. In certain embodiments, the primate or subject is a human. In certain instances, the human is an adult. In certain instances, the human is child. In further instances, the human is 12 years of age or younger. In certain instances, the human is elderly. In other instances, the human is 60 years of age or older. Other examples of subjects include experimental animals such as mice, rats, dogs, cats, goats, sheep, pigs, and cows. The experimental animal can be an animal model for a disorder, e.g., a transgenic mouse with hypertensive pathology. A patient can be a human suffering from hypertension, or its variants or etiological forms.

By "pharmaceutically acceptable", it is meant the carrier, diluent or excipient must be compatible with the other ingredients of the formulation and not deleterious to the recipient thereof.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

A "therapeutically effective amount" or "effective amount" as used herein refers to the amount of active compound or pharmaceutical agent that elicits a biological or medicinal response in a tissue, system, animal, individual or human that is being sought by a researcher, veterinarian, medical doctor or other clinician, which includes one or more of the following: (1) preventing the disease; for example, preventing a disease, condition or disorder in an individual that may be predisposed to the disease, condition or disorder but does not yet experience or display the pathology or symptomatology of the disease, (2) inhibiting the disease; for example, inhibiting a disease, condition or disorder in an individual that is experiencing or displaying the pathology or symptomatology of the disease, condition or disorder (i.e., arresting further development of the pathology and/or symptomatology), and (3) ameliorating the disease; for example, ameliorating a disease, condition or disorder in an individual that is experiencing or displaying the pathology or symptomatology of the disease, condition or disorder (i.e., reversing the pathology and/or symptomatology). As such, a non-limiting example of a "therapeutically effective amount" or "effective amount" of a formulation of the present disclosure may be used to inhibit, block, or reverse the activation, migration, or proliferation of cells or to effectively treat hypertension or ameliorate the symptoms of hypertension.

The terms "treat," "treated," "treatment," or "treating" as used herein refers to both therapeutic treatment in some embodiments and prophylactic or preventative measures in other embodiments, wherein the object is to prevent or slow (lessen) an undesired physiological condition, disorder or disease, or to obtain beneficial or desired clinical results. For the purposes described herein, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. A prophylactic benefit of treatment includes prevention of a condition, retarding the progress of a condition, stabilization of a condition, or decreasing the likelihood of occurrence of a condition. As used herein, "treat," "treated," "treatment," or "treating" includes prophylaxis in some embodiments.

The terms "precipitate," "precipitates," or "precipitation" as used herein, refers to the creation of a new solid phase comprising one or more chemical entities from solution. Those of ordinary skill in the art will understand and appreciate that the solid phase may exist in crystalline and/or amorphous forms and that crystalline forms may include, but are not limited to, polymorphs, cocrystals, ionic cocrystals, ionic cocrystal solvates, salts, solvated salts and solvates.

The terms "substantially precipitate," "substantially precipitates" or "substantial precipitation" as used herein, refers to an amount of precipitation that is detectable, directly or indirectly, by techniques known to a person of ordinary skill in the art. Examples of techniques may include, but are not limited to, visual inspection of solutions to determine changes in solution opaqueness/transparency, Focused Beam Reflectance Measurement (FBRM) technology, Infrared Spectroscopy, Raman Spectroscopy, UV spectroscopy and turbidity analysis.

The terms "very slightly soluble" or "practically insoluble" as used herein, refers to a concentration of less than about 0.6 mg/mL, preferably of less than about 0.2 mg/mL, and most preferably of less than about 0.05 mg/mL.

EXAMPLES

Example 1

Formation of Amlodipine Salt Crystals in the Absence or Presence of a Magnetic Stir Bar (1A) Purified water (200 ml) was added to a 400 ml glass container fitted with overhead rotational stirring using a PTFE (polytetrafluoroethylene) coated 2" diameter impeller and shaft. Stirring was initiated at 250 rpm and anhydrous citric acid (110 mg) was added and dissolved. Amlodipine besylate (278 mg) was then added followed by 1000 mg sodium benzoate. After 25 minutes, the stirring speed was increased to 450 rpm for 45 additional minutes.

Results: No precipitate of amlodipine benzoate salt appeared until after 1 hour of stirring. The particles were large, >100 microns in length.

(1B) The procedure in example (1A) was repeated with the exception that a magnetic stir bar was placed in the glass container in addition to the overhead stirrer. No external magnetic stirring apparatus was present, only the stir bar. The stirring speed was maintained at 250 rpm.

Results: Amlodipine benzoate salt precipitated after 3 minutes of stirring. The particles were small, at <50 microns in length.

(1C) Purified water (100 ml) was added to a 250 ml glass container fitted with overhead rotational stirring using a PTFE (polytetrafluoroethylene) coated 2" diameter impeller and shaft. Stirring was initiated at 275 rpm and polysorbate 80 (1.0 grams) was added and dissolved. Amlodipine besylate (1.39 grams) was added and allowed to disperse, then sodium benzoate (5.0 grams) was added. The suspension was stirred for 30 minutes after the sodium benzoate addition then the stirring was stopped and a sample taken for microscopic evaluation.

Results: A precipitate appeared in the suspension that was primarily large rod-shaped crystals, >100 microns in length.

(1D) The procedure in example (1C) was repeated with the exception that a magnetic stir bar was placed in the glass container in addition to the overhead stirrer. No external magnetic stirring apparatus was present, only the stir bar. The overhead stirring speed was maintained at 275 rpm.

Results: Amlodipine benzoate salt precipitated after ~3 minutes of stirring. The particles were small and needle-shaped, at <50 microns in length.

Example 2

Concentration Effect on Amlodipine Salt Crystal Formation with Non-Magnetic Stirring (2A) Purified water (50 ml) was added to a glass container fitted with overhead rotational stirring using a PTFE coated 2" diameter impeller and shaft. Stirring was initiated at 250 rpm and 2500 mg sodium benzoate were added and dissolved. Amlodipine besylate (695 mg) was then added followed by 275 mg anhydrous citric acid. This solution is equivalent to preparing the crystals using a water amount of 10% of a final formulation weight.

Results: Amlodipine benzoate salt began precipitating immediately as particles<~50 micron.

(2B) Purified water (150 ml) was added to a glass container fitted with overhead rotational stirring using a PTFE coated impeller and shaft. Stirring was initiated at 250 rpm and 2500 mg sodium benzoate were added and dissolved. Amlodipine besylate (695 mg) was then added followed by 275 mg anhydrous citric acid. This solution is equivalent to preparing the crystals using a water amount of 30% of a final formulation weight.

Results: Amlodipine benzoate salt began precipitating immediately as particles<~50 micron.

(2C) Purified water (250 ml) was added to a glass container fitted with overhead rotational stirring using a PTFE coated impeller and shaft. Stirring was initiated at 250 rpm and 2500 mg sodium benzoate were added and dissolved. Amlodipine besylate (695 mg) was then added followed by 275 mg anhydrous citric acid. This solution is equivalent to preparing the crystals using a water amount of 50% of a final formulation weight.

Results: Amlodipine benzoate salt began precipitating, then dissolved, and finally re-precipitated as large particles (>50 microns) after ~1 hour.

(2D) Purified water (45 ml) was added to a 250 ml glass container fitted with overhead rotational stirring using a PTFE coated 2" diameter impeller and shaft. Stirring was initiated at 250 rpm and 500 mg of a 30% w/w simethicone powder were added and dissolved. Sodium benzoate (5000 mg) was added and dissolved and then amlodipine besylate (1390 mg in 5 ml water) was added. This solution is equivalent to preparing the crystals using a water amount of 5% of a final formulation weight.

Results: Amlodipine benzoate salt precipitated immediately as very fine particles that caked on the stirrer and did not disperse easily.

(2E) Purified water (90 ml) was added to a 250 mL HDPE container fitted with overhead rotational stirring using a PTFE coated 2" diameter impeller and shaft. Stirring was initiated at 250 rpm and 500 mg of a 30% w/w simethicone powder were added and dissolved. Sodium benzoate (5000 mg) was added and dissolved and then amlodipine besylate (1390 mg in 10 ml water) was added. This solution is equivalent to preparing the crystals using a water amount of 10% of a final formulation weight.

Results: Amlodipine benzoate salt precipitated rapidly as small particles that dispersed easily.

(2F) Purified water (95 ml) was added to a 250 ml glass container fitted with overhead rotational stirring using a PTFE coated 2" diameter impeller and shaft. Stirring was initiated at 250 rpm and 250 mg of a 30% w/w simethicone powder were added and dissolved. Sodium benzoate (2500 mg) was added and dissolved and then amlodipine besylate (695 mg in 5 mL water) was added. This solution is equivalent to preparing the crystals using a water amount of 20% of a final formulation weight.

Results: Amlodipine benzoate salt precipitated rapidly as small particles with some agglomeration.

Example 3

Amlodipine compositions were prepared using a process in which the preferred amlodipine salt is formed in one container, another part of the formulation was prepared in a second container, and the contents of the first container and the second container were combined.

(3A) Purified water (approximately 10% of the final formulation weight) was added to a polyethylene first vessel (e.g., LLPD) fitted with magnetic stirring. Stirring was initiated and polysorbate 80 was added and dispersed in the solution. Amlodipine was then added with stirring until it was well dispersed, followed by the addition of the salt forming agent (e.g., sodium benzoate or sodium naphthalene-2-sulfonate). Stirring was continued for approximately 30 minutes after the addition of the salt forming agent.

Purified water (approximately 80% of the final formulation weight) was added to a stainless steel second vessel fitted with overhead rotational stirring using a shaft and impeller. Stirring was initiated and the following components were added individually with sufficient stirring after each addition, to ensure each component was dissolved (citric acid, sodium citrate, sucralose, flavoring agent, hypromellose) or well dispersed (simethicone, silicon dioxide). High shear mixing was used during and after the addition of the hypromellose to facilitate dispersion and solubilization of this component.

The contents of the first vessel were then transferred to the second vessel with stirring. Additional water was added to the second vessel to bring its weight to approximately 98% of the final formulation weight. The pH of the solution was measured and if required, adjusted to the desired pH, then the solution was brought to the final weight with purified water.

(3B) Purified water (approximately 10% of the final formulation weight) was added to a glass vessel fitted with magnetic stirring. Stirring was initiated and simethicone was added and dispersed in the solution. The salt forming agent was then added and dissolved. Amlodipine was dispersed in purified water (approximately 1% of the final formulation weight) and the resulting liquid slowly added to the first vessel with stirring. Stirring was continued for approximately 30 minutes after the addition of the amlodipine.

Purified water (approximately 22% of the final formulation weight) was added to a second glass vessel fitted with magnetic stirring. The water was heated to approximately 70° C. and silicone dioxide and hypromellose were added with stirring. The heating was discontinued and an equal portion of cold water was added to the second vessel. Stirring was continued and sucralose and flavor were added and dissolved. Purified water (approximately 6% of the final formulation weight) was then added.

The solutions from the two vessels were combined with stirring. The vessels were rinsed with purified water (approximately 20% of the final formulation weight) and the rinses added to the formulation. The pH was checked, and as needed adjusted to pH 4.9 with a solution of citric acid (1.1 g anhydrous citric acid in 50 ml purified water). The solution was brought to final weight with purified water and mixed with high shear mixing.

(3C) Purified water (approximately 10% of the final formulation weight) was added to a first glass vessel fitted with magnetic stirring. Stirring was initiated and one-half of the simethicone and nine-tenths of the salt forming agent were added. Amlodipine was then added over about 5 minutes. Stirring was continued for approximately 30 minutes after the addition of the amlodipine was completed.

Purified water (approximately 70% of the final formulation weight) was added to a second glass vessel fitted with magnetic stirring. The remaining one-half of the simethicone, the remaining one-tenth of the salt forming agent, sucralose, silicon dioxide, flavor, and hypromellose were added to the vessel with stirring. High shear mixing was used after the addition of the hypromellose to facilitate dispersion and solubilization of this component.

The contents of the first vessel were then transferred to the second vessel with stirring. Additional water was added to the second vessel to bring its weight to approximately 90% of the final formulation weight. The formulation was again subjected to high shear mixing, and then allowed to deaerate. The preparation was brought to final weight with purified water and mixed. The pH of the solution was measured and as required, adjusted to the desired pH with anhydrous citric acid.

Example 4

Amlodipine compositions were prepared using a process in which the preferred amlodipine salt is formed in one container, and then transferred to a second container for the remaining process.

Purified water (approximately 10% of the final formulation weight) was added to a HDPE vessel fitted with a magnetic stirrer. Stirring was initiated and simethicone was added and dispersed in the solution. The salt forming agent was then added with stirring followed by the addition of amlodipine dispersed in purified water (approximately 1% of the final formulation weight). Stirring was continued for approximately 30 minutes after the addition of the amlodipine.

The preparation was transferred to a stainless steel vessel and additional purified water (approximately 45% of the final formulation weight) was added to the vessel. Stirring was initiated and the following components were added individually with stirring; citric acid, sucralose, silicon dioxide, flavor, and hypromellose. High shear mixing was used after the addition of the hypromellose to facilitate dispersion and solubilization. Purified water (30% of the final formulation weight) was added with stirring and the preparation was allowed to deaerate. The preparation was brought to final weight with purified water and mixed. The pH was measured.

Example 5

Amlodipine compositions were prepared using processes in which the preferred amlodipine salt is formed in a small portion of the final volume in one container, and then additional components are added to the same container to complete the process.

(5A) Purified water (approximately 10% of the final formulation weight) was added to a glass vessel fitted with magnetic stirring. Stirring was initiated and simethicone was added and dispersed in the solution. The salt forming agent was then added with stirring followed by the addition of amlodipine. Stirring was continued for approximately 30 minutes after the addition of the amlodipine.

Additional purified water (approximately 85% of the final formulation weight) was added to the vessel. Stirring was initiated and the following components were added individually with stirring; citric acid, sodium citrate, sucralose, silicon dioxide, flavor, and hypromellose. High shear mixing was used after the addition of the hypromellose to facilitate dispersion and solubilization, then the preparation was allowed to deaerate. The pH was checked and adjusted if necessary, and the preparation was brought to final weight with purified water.

(5B) Polysorbate 80 was added to a glass vessel fitted with magnetic stirring. Purified water (approximately 10% of the final formulation weight) was added and stirring was initiated to ensure dispersion of the polysorbate in the solution. Amlodipine was then added with stirring until it was well dispersed, followed by the addition of the salt forming agent. Stirring was continued for approximately 30 minutes after the addition of the salt forming agent.

Additional purified water (approximately 85% of the final formulation weight) was added to the vessel. Stirring was initiated and the following components were added individually with stirring; citric acid, sodium citrate, sucralose, silicon dioxide, flavor, simethicone and hypromellose. High shear mixing was used after the addition of the hypromellose to facilitate dispersion and solubilization, then the preparation was allowed to deaerate. The pH was checked and adjusted if necessary, and the preparation was brought to final weight with purified water.

Example 6

Amlodipine compositions were prepared using processes in which the preferred amlodipine salt is formed in one container in a volume greater than one-half of the final volume, and then additional components were added to the same container to complete the process.

(6A) Purified water (approximately 90% of the final formulation weight) was added to a glass vessel fitted with magnetic stirring. Stirring was initiated and citric acid was added and dissolved in the solution, followed by amlodipine, followed by the salt forming agent. The solution was stirred for approximately 30 minutes to allow formation of the amlodipine salt. The solution was then cooled to 2-8° C. for 1 hour with continued stirring. Sucralose, silicon dioxide, simethicone, povidone for some formulations, and hypromellose were added with stirring. High shear mixing was applied to the formulation after the hypromellose addition. The formulation was then stirred for 30 minutes, brought to final weight with purified water, and stirred for another 30 minutes.

(6B) Purified water (approximately 90% of the final formulation weight) was added to a glass vessel fitted with magnetic stirring. Stirring was initiated and citric acid was added and dissolved in the solution, followed by sodium citrate, amlodipine, then the salt forming agent. The solution was stirred for approximately 30 minutes to allow formation of the amlodipine salt. Sodium benzoate, sucralose, silicon dioxide, simethicone, (flavor and color in some formulations) and hypromellose were added with stirring. High shear mixing was applied to the formulation after the hypromellose addition. The formulation was then stirred for 30 minutes, brought to final weight with purified water, and stirred for another 30 minutes.

(6C) Purified water (approximately 90% of the final formulation weight) was added to a glass vessel fitted with magnetic stirring. Stirring was initiated and citric acid was added and dissolved in the solution, followed by amlodipine, then the salt forming agent. The solution was stirred for approximately 30 minutes to allow formation of the amlodipine salt. The solution was then cooled to 2-8° C. for 1 hour with continued stirring. Sucralose, silicon dioxide, simethicone and povidone were added with stirring. The formulation was then stirred for 30 minutes, brought to final weight with purified water, and stirred for another 30 minutes.

(6D) Purified water (approximately 90% of the final formulation weight) was added to a glass vessel fitted with magnetic stirring. Stirring was initiated and hypromellose was added and dissolved in the water with high shear mixing. Citric acid, salt forming agent, sucralose, simethicone, flavoring agent and color in some preparations, were then added with stirring. The solution was brought to its final weight with purified water, and the amlodipine was added with stirring. The solution was stirred for approximately 30 minutes to allow formation of the amlodipine salt.

(6E) Purified water (approximately 90% of the final formulation weight) was added to a glass vessel fitted with magnetic stirring. Stirring was initiated and mannitol was added and dissolved in the solution, followed by hypromellose, citric acid, salt forming agent, sucralose, simethicone, silicon dioxide, and in some formulations, a flavor. The solution was brought to its final weight with purified water, and the amlodipine was added with stirring. In some preparations, the formulation was subjected to ultrasonic energy (sonication) and in some preparations the formulation was mixed with high shear mixing. The solution was then stirred for approximately 30 minutes to allow formation of the amlodipine salt.

Example a

Effect of pH on the Formation of Degradants in Amlodipine Formulations

Formulations were prepared containing Amlodipine according to Table A-1. Each formulation was dispensed into screw-capped high density polyethylene (HDPE) bottles and stored at both 5° C. and ambient temperature. Samples were removed periodically and analyzed by a stability indicating high performance liquid chromatography (HPLC) method for content of amlodipine and any degradants.

The HPLC method provided separation of amlodipine, amlodipine degradants and formulation components on a C18 column with a gradient program using mobile phases containing 0.1% trifluoroacetic acid (TFA) in water, and 0.1% TFA in acetonitrile flowing at 1 mL/min. Detection was by UV absorbance at 237 nm for amlodipine and its degradants. Any unknown impurities were reported by their relative retention time (RRT) to amlodipine.

TABLE A-1

Composition (in mg/ml) of Amlodipine Formulations at Varying pH Levels

| Component | \multicolumn{8}{c}{Formulation} | | | | | | | |
|---|---|---|---|---|---|---|---|---|
| | A1 | A2 | A3 | A4 | A5 | A6 | A7 | A8 |
| Amlodipine besylate [a] | 1.39 | 1.39 | 1.39 | 1.39 | 1.39 | 1.39 | 1.39 | 1.39 |
| Mannitol | 90.00 | — | — | — | — | — | — | — |
| Hypromellose K750 | 5.00 | — | — | — | — | — | — | — |
| Citric acid, anhydrous | 3.42 | 1.35 | 0.84 | 0.53 | 0.36 | 0.31 | 0.23 | 0.17 |
| Sodium citrate, dihydrate | — | — | — | — | — | 0.36 | 0.47 | 0.55 |
| Sodium benzoate | 5.00 | 5.00 | 5.00 | 5.00 | 5.00 | 5.00 | 5.00 | 5.00 |
| Sucralose/maltodextrin | 4.00 | — | — | — | — | — | — | — |
| Sucralose | — | 0.70 | 0.70 | 0.70 | 0.70 | 0.70 | 0.70 | 0.70 |
| Simethicone | 0.15 | 0.15 | 0.15 | 0.15 | 0.15 | 0.15 | 0.15 | 0.15 |
| Silicon dioxide | 0.50 | 0.50 | 0.50 | 0.50 | 0.50 | 0.50 | 0.50 | 0.50 |
| Artificial cherry flavor | — | 0.50 | 0.50 | 0.50 | 0.50 | 0.50 | 0.50 | 0.50 |
| Hypromellose K1500 | — | 5.00 | 5.00 | 5.00 | 5.00 | 5.00 | 5.00 | 5.00 |
| Water | q.s. | q.s. | q.s. | q.s. | q.s. | q.s. | q.s. | q.s. |
| pH | 3.98 | 4.51 | 4.71 | 4.90 | 5.09 | 5.31 | 5.54 | 5.75 |

[a] = equivalent to 1 mg/ml Amlodipine

The results of the HPLC analysis for amlodipine and the main degradants in the samples stored at 5° C. are provided in Table A-2. The results show a decrease in total impurities as pH is increased from 4.0 to 5.7.

TABLE A-2

Assay and Primary Degradants Present in the Formulations

| Weeks | A1 | A2 | A3 | A4 | A5 | A6 | A7 | A8 |
|---|---|---|---|---|---|---|---|---|
| \multicolumn{9}{c}{Amlodipine (% initial)} | | | | | | | | |
| Initial | 100.00 | 100.00 | 100.00 | 100.00 | 100.00 | 100.00 | 100.00 | 100.00 |
| 4 | 97.77 | 96.61 | 99.30 | 99.99 | 100.96 | 99.20 | 101.11 | 96.49 |
| 8 | 97.47 | 97.32 | 104.37 | 100.07 | 101.33 | 100.58 | 98.10 | 97.04 |
| 12 | 97.88 | 97.41 | 102.28 | 102.09 | 101.88 | 100.59 | 100.74 | 96.38 |
| 26 | 95.14 | 97.02 | 100.80 | 99.69 | 105.89 | 102.46 | 102.01 | 98.37 |
| 52 | 96.02 | 97.16 | 100.08 | 101.26 | 101.94 | 100.40 | 99.96 | 97.34 |
| 78 | 98.24 | 98.37 | 101.86 | 100.40 | 101.93 | 107.40 | 99.59 | 99.08 |
| 104 | 97.32 | 98.02 | 99.66 | 109.83 | 102.00 | 101.79 | 100.25 | 97.37 |
| \multicolumn{9}{c}{USP Impurity A/EP Impurity D (wt % of Amlodipine)} | | | | | | | | |
| Initial | 0.06 | 0.02 | 0.03 | 0.00 | 0.03 | 0.00 | 0.00 | 0.00 |
| 4 | 0.08 | 0.05 | 0.03 | 0.04 | 0.04 | 0.00 | 0.02 | 0.04 |
| 8 | 0.12 | 0.01 | 0.01 | 0.01 | 0.01 | 0.04 | 0.01 | 0.03 |
| 12 | 0.13 | 0.17 | 0.02 | 0.02 | 0.03 | 0.05 | 0.02 | 0.04 |
| 26 | 0.15 | 0.04 | 0.04 | 0.04 | 0.05 | 0.05 | 0.04 | 0.04 |
| 52 | 0.15 | 0.07 | 0.06 | 0.06 | 0.06 | 0.07 | 0.06 | 0.06 |
| 78 | 0.27 | 0.08 | 0.07 | 0.07 | 0.06 | 0.10 | 0.06 | 0.07 |
| 104 | 0.33 | 0.06 | 0.05 | 0.04 | 0.04 | 0.05 | 0.04 | 0.04 |
| \multicolumn{9}{c}{Impurity RRT 0.97 (wt % of Amlodipine)} | | | | | | | | |
| Initial | 0.02 | 0.00 | 0.00 | 0.00 | 0.00 | 0.00 | 0.00 | 0.00 |
| 4 | 0.02 | 0.00 | 0.01 | 0.00 | 0.00 | 0.01 | 0.00 | 0.00 |
| 8 | 0.06 | 0.02 | 0.02 | 0.01 | 0.01 | 0.00 | 0.00 | 0.00 |
| 12 | 0.04 | 0.04 | 0.03 | 0.02 | 0.02 | 0.01 | 0.01 | 0.01 |
| 26 | 0.07 | 0.08 | 0.07 | 0.05 | 0.04 | 0.04 | 0.03 | 0.02 |
| 52 | 0.11 | 0.13 | 0.13 | 0.12 | 0.10 | 0.09 | 0.06 | 0.04 |
| 78 | 0.16 | 0.21 | 0.20 | 0.18 | 0.15 | 0.14 | 0.10 | 0.06 |
| 104 | 0.22 | 0.26 | 0.25 | 0.24 | 0.20 | 0.18 | 0.13 | 0.08 |
| \multicolumn{9}{c}{Total Impurities (wt % of Amlodipine)} | | | | | | | | |
| Initial | 0.23 | 0.07 | 0.06 | 0.03 | 0.08 | 0.06 | 0.06 | 0.08 |
| 4 | 0.28 | 0.11 | 0.09 | 0.09 | 0.08 | 0.04 | 0.06 | 0.14 |
| 8 | 0.66 | 0.09 | 0.09 | 0.07 | 0.09 | 0.07 | 0.06 | 0.10 |
| 12 | 0.35 | 0.34 | 0.12 | 0.08 | 0.09 | 0.10 | 0.07 | 0.09 |
| 26 | 0.42 | 0.25 | 0.21 | 0.18 | 0.17 | 0.15 | 0.12 | 0.10 |
| 52 | 0.64 | 0.41 | 0.35 | 0.31 | 0.33 | 0.33 | 0.26 | 0.24 |
| 78 | 0.84 | 0.53 | 0.46 | 0.38 | 0.33 | 0.40 | 0.27 | 0.25 |
| 104 | 1.07 | 0.65 | 0.61 | 0.51 | 0.44 | 0.36 | 0.31 | 0.28 |

The results of the HPLC analysis for amlodipine and the main degradants in the samples stored at ambient temperature are provided in Table A-3. The results show a decrease in total impurities as pH is increased from 4.0 to 5.7.

TABLE A-3

Assay and Primary Degradants Present in the Formulations

| Weeks | Formulation | | | | | | | |
|---|---|---|---|---|---|---|---|---|
| | A1 | A2 | A3 | A4 | A5 | A6 | A7 | A8 |
| Amlodipine (% initial) | | | | | | | | |
| Initial | 100.00 | 100.00 | 100.00 | 100.00 | 100.00 | 100.00 | 100.00 | 100.00 |
| 2 | 89.38 | 98.81 | 102.36 | 99.31 | 102.33 | 102.05 | 101.23 | 101.34 |
| 4 | 90.71 | 97.05 | 99.80 | 100.54 | 105.81 | 101.27 | 99.14 | 98.06 |
| 6 | 85.22 | 95.86 | 102.42 | 101.22 | 100.86 | 102.45 | 100.42 | 97.03 |
| 8 | 83.75 | 97.13 | 99.80 | 101.38 | 103.48 | 101.81 | 100.14 | 101.44 |
| 12 | 79.33 | 96.28 | 100.33 | 100.61 | 103.18 | 101.61 | 100.90 | 97.50 |
| 26 | — | 91.68 | 96.97 | 98.87 | 101.72 | 101.53 | 100.27 | 99.20 |
| USP Impurity A/EP Impurity D (wt % of Amlodipine) | | | | | | | | |
| Initial | 0.06 | 0.02 | 0.03 | 0.00 | 0.03 | 0.00 | 0.00 | 0.00 |
| 2 | 0.30 | 0.05 | 0.05 | 0.05 | 0.04 | 0.03 | 0.01 | 0.04 |
| 4 | 0.43 | 0.08 | 0.08 | 0.07 | 0.07 | 0.06 | 0.06 | 0.06 |
| 6 | 0.65 | 0.05 | 0.05 | 0.03 | 0.04 | 0.10 | 0.05 | 0.05 |
| 8 | 0.79 | 0.05 | 0.04 | 0.03 | 0.04 | 0.10 | 0.17 | 0.09 |
| 12 | 1.03 | 0.06 | 0.05 | 0.05 | 0.04 | 0.14 | 0.12 | 0.13 |
| 26 | — | 0.27 | 0.21 | 0.20 | 0.18 | 0.26 | 0.23 | 0.24 |
| Impurity RRT 0.97 (wt % of Amlodipine) | | | | | | | | |
| Initial | 0.02 | 0.00 | 0.00 | 0.00 | 0.00 | 0.00 | 0.00 | 0.00 |
| 2 | 0.29 | 0.12 | 0.10 | 0.07 | 0.05 | 0.03 | 0.03 | 0.01 |
| 4 | 0.43 | 0.25 | 0.20 | 0.15 | 0.11 | 0.07 | 0.05 | 0.04 |
| 6 | 0.58 | 0.33 | 0.28 | 0.22 | 0.16 | 0.13 | 0.10 | 0.06 |
| 8 | 0.67 | 0.40 | 0.35 | 0.29 | 0.22 | 0.18 | 0.11 | 0.07 |
| 12 | 0.73 | 0.47 | 0.43 | 0.38 | 0.32 | 0.25 | 0.17 | 0.10 |
| 26 | — | 0.51 | 0.48 | 0.45 | 0.41 | 0.37 | 0.30 | 0.21 |
| Total Impurities (wt % of Amlodipine) | | | | | | | | |
| Initial | 0.23 | 0.07 | 0.06 | 0.03 | 0.08 | 0.06 | 0.06 | 0.08 |
| 2 | 1.19 | 0.32 | 0.29 | 0.23 | 0.17 | 0.15 | 0.09 | 0.13 |
| 4 | 1.78 | 0.60 | 0.49 | 0.39 | 0.37 | 0.24 | 0.24 | 0.30 |
| 6 | 2.41 | 0.75 | 0.62 | 0.50 | 0.39 | 0.47 | 0.37 | 0.30 |
| 8 | 2.43 | 0.94 | 0.75 | 0.60 | 0.53 | 0.50 | 0.49 | 0.36 |
| 12 | 3.77 | 1.29 | 0.94 | 0.76 | 0.73 | 0.72 | 0.58 | 0.49 |
| 26 | — | 1.85 | 1.47 | 1.23 | 1.18 | 1.21 | 1.05 | 0.95 |

Example B

Effect of Benzoate Concentration on the Stability of Amlodipine Formulations

Formulations were prepared containing Amlodipine according to Table B-1. Each formulation was dispensed into screw-capped HDPE bottles and stored at ambient temperature. Formulations B6, B7, and B8 were also stored at 5° C. Samples were removed periodically and analyzed using the HPLC method in Example A.

TABLE B-1

Composition (in mg/ml) of Amlodipine Formulations at Varying Benzoate Levels

| Component | Formulation | | | | | | | |
|---|---|---|---|---|---|---|---|---|
| | B1 | B2 | B3 | B4 | B5 | B6 | B7 | B8 |
| Amlodipine besylate [a] | 1.39 | 1.39 | 1.39 | 1.39 | 1.39 | 1.39 | 1.39 | 1.39 |
| Hypromellose K750 | — | — | — | — | — | 5.00 | 5.00 | 5.00 |
| Citric acid, anhydrous | [b] | [b] | [b] | [b] | [b] | 0.55 | 0.90 | 1.15 |
| Sodium benzoate | 1.00 | 2.00 | 3.00 | 4.00 | 5.00 | 5.00 | 7.50 | 10.00 |
| Sucralose | 0.70 | 0.70 | 0.70 | 0.70 | 0.70 | 0.70 | 0.70 | 0.70 |
| Simethicone | 0.15 | 0.15 | 0.15 | 0.15 | 0.15 | 0.15 | 0.15 | 0.15 |
| Silicon dioxide | 0.50 | 0.50 | 0.50 | 0.50 | 0.50 | — | — | — |

TABLE B-1-continued

Composition (in mg/ml) of Amlodipine Formulations at Varying Benzoate Levels

| Component | Formulation | | | | | | | |
|---|---|---|---|---|---|---|---|---|
| | B1 | B2 | B3 | B4 | B5 | B6 | B7 | B8 |
| Artificial cherry flavor | 0.50 | 0.50 | 0.50 | 0.50 | 0.50 | — | — | 0.50 |
| Hypromellose K1500 | 5.00 | 5.00 | 5.00 | 5.00 | 5.00 | — | — | — |
| Red 40 Al lake color | — | — | — | — | — | — | — | 0.015 |
| Water | q.s. | q.s. | q.s. | q.s. | q.s. | q.s. | q.s. | q.s. |
| pH | 4.85 | 4.89 | 4.89 | 4.89 | 4.89 | 4.88 | 4.84 | 4.87 |

$^a$ = equivalent to 1 mg/ml Amlodipine
$^b$ = adjusted pH to 4.9 with a solution containing 1.1 g citric acid in 50 ml purified water before final dilution.

The results of the HPLC analysis for amlodipine and the main degradants in the samples stored at 5° C. are provided in Table B-2.

TABLE B-2

Assay and Primary Degradants Present in the Formulations

| Weeks | Formulation | | |
|---|---|---|---|
| | B6 | B7 | B8 |
| Amlodipine (% initial) | | | |
| Initial | 100.00 | 100.00 | 100.00 |
| 2 | 97.56 | 99.22 | 98.15 |
| 4 | 97.18 | 98.00 | 98.18 |
| 6 | 99.13 | 99.04 | 97.28 |
| 8 | 98.81 | 98.44 | 98.17 |
| 12 | 99.17 | 98.80 | 98.80 |
| 26 | 99.89 | 97.03 | 97.42 |
| 52 | 96.34 | 98.04 | 97.19 |
| 78 | 98.10 | 99.20 | 99.07 |
| 104 | 97.33 | 98.59 | 97.56 |
| USP Impurity A/EP Impurity D (wt % of Amlodipine) | | | |
| Initial | 0.03 | 0.00 | 0.04 |
| 2 | 0.03 | 0.02 | 0.02 |
| 4 | 0.02 | 0.03 | 0.03 |
| 6 | 0.03 | 0.02 | 0.02 |
| 8 | 0.03 | 0.04 | 0.03 |
| 12 | 0.04 | 0.03 | 0.02 |
| 26 | 0.05 | 0.03 | 0.04 |
| 52 | 0.04 | 0.03 | 0.03 |
| 78 | 0.11 | 0.09 | 0.09 |
| 104 | 0.13 | 0.10 | 0.10 |

TABLE B-2-continued

Assay and Primary Degradants Present in the Formulations

| Weeks | Formulation | | |
|---|---|---|---|
| | B6 | B7 | B8 |
| Impurity RRT 0.97 (wt % of Amlodipine) | | | |
| Initial | 0.00 | 0.00 | 0.00 |
| 2 | 0.00 | 0.00 | 0.00 |
| 4 | 0.01 | 0.01 | 0.01 |
| 6 | 0.02 | 0.01 | 0.01 |
| 8 | 0.02 | 0.02 | 0.01 |
| 12 | 0.05 | 0.04 | 0.03 |
| 26 | 0.10 | 0.08 | 0.07 |
| 52 | 0.19 | 0.15 | 0.12 |
| 78 | 0.28 | 0.25 | 0.21 |
| 104 | 0.35 | 0.32 | 0.27 |
| Total Impurities (wt % of Amlodipine) | | | |
| Initial | 0.10 | 0.09 | 0.15 |
| 2 | 0.08 | 0.08 | 0.07 |
| 4 | 0.07 | 0.07 | 0.07 |
| 6 | 0.10 | 0.07 | 0.09 |
| 8 | 0.10 | 0.09 | 0.08 |
| 12 | 0.13 | 0.11 | 0.10 |
| 26 | 0.22 | 0.17 | 0.17 |
| 52 | 0.37 | 0.30 | 0.24 |
| 78 | 0.54 | 0.44 | 0.39 |
| 104 | 0.73 | 0.58 | 0.52 |

The results of the HPLC analysis for amlodipine and the main degradants in the samples stored at ambient temperature are provided in Table B-3.

TABLE B-3

Assay and Primary Degradants Present in the Formulations

| Weeks | Formulation | | | | | | | |
|---|---|---|---|---|---|---|---|---|
| | B1 | B2 | B3 | B4 | B5 | B6 | B7 | B8 |
| Amlodipine (% initial) | | | | | | | | |
| Initial | 100.00 | 100.00 | 100.00 | 100.00 | 100.00 | 100.00 | 100.00 | 100.00 |
| 2 | 98.98 | 105.36 | 100.82 | 97.67 | 100.22 | 98.62 | 98.70 | 99.05 |
| 4 | 97.06 | 104.08 | 99.24 | 95.90 | 97.91 | 96.01 | 98.44 | 97.90 |
| 6 | 96.31 | 103.13 | 99.36 | 97.32 | 97.01 | 97.89 | 97.89 | 97.37 |
| 8 | 96.51 | 103.91 | 99.54 | 96.90 | 96.84 | 97.04 | 97.26 | 97.39 |
| 12 | | | | | | 96.38 | 95.78 | 95.40 |
| 26 | | | | | | 92.69 | 95.34 | 94.49 |
| USP Impurity A/EP Impurity D (wt % of Amlodipine) | | | | | | | | |
| Initial | 0.05 | 0.04 | 0.03 | 0.03 | 0.03 | 0.03 | 0.00 | 0.04 |
| 2 | 0.17 | 0.10 | 0.08 | 0.07 | 0.07 | 0.05 | 0.04 | 0.05 |
| 4 | 0.22 | 0.12 | 0.10 | 0.08 | 0.07 | 0.09 | 0.07 | 0.08 |
| 6 | 0.28 | 0.15 | 0.11 | 0.10 | 0.08 | 0.12 | 0.09 | 0.09 |

TABLE B-3-continued

Assay and Primary Degradants Present in the Formulations

| | Formulation | | | | | | | |
|---|---|---|---|---|---|---|---|---|
| Weeks | B1 | B2 | B3 | B4 | B5 | B6 | B7 | B8 |
| 8 | 0.32 | 0.16 | 0.13 | 0.11 | 0.12 | 0.12 | 0.11 | 0.11 |
| 12 | | | | | | 0.16 | 0.14 | 0.13 |
| 26 | | | | | | 0.24 | 0.23 | 0.22 |
| Impurity RRT 0.97 (wt % of Amlodipine) | | | | | | | | |
| Initial | 0.00 | 0.00 | 0.00 | 0.00 | 0.00 | 0.00 | 0.00 | 0.00 |
| 2 | 0.07 | 0.08 | 0.09 | 0.09 | 0.08 | 0.09 | 0.13 | 0.12 |
| 4 | 0.19 | 0.19 | 0.19 | 0.18 | 0.19 | 0.22 | 0.28 | 0.25 |
| 6 | 0.28 | 0.28 | 0.28 | 0.26 | 0.26 | 0.33 | 0.38 | 0.36 |
| 8 | 0.34 | 0.33 | 0.34 | 0.34 | 0.33 | 0.40 | 0.47 | 0.44 |
| 12 | | | | | | 0.51 | 0.55 | 0.55 |
| 26 | | | | | | 0.60 | 0.63 | 0.63 |
| Total Impurities (wt % of Amlodipine) | | | | | | | | |
| Initial | 0.22 | 0.08 | 0.06 | 0.07 | 0.09 | 0.10 | 0.09 | 0.15 |
| 2 | 0.59 | 0.40 | 0.43 | 0.39 | 0.35 | 0.26 | 0.27 | 0.29 |
| 4 | 0.80 | 0.59 | 0.56 | 0.55 | 0.45 | 0.48 | 0.52 | 0.48 |
| 6 | 0.99 | 0.70 | 0.63 | 0.60 | 0.57 | 0.69 | 0.70 | 0.65 |
| 8 | 1.11 | 0.83 | 0.72 | 0.70 | 0.72 | 0.81 | 0.89 | 0.80 |
| 12 | | | | | | 1.06 | 1.05 | 1.07 |
| 26 | | | | | | 1.45 | 1.54 | 1.50 |

Example C

Effect of Hypromellose on the Formation of Degradants in Amlodipine Formulations Formulations were prepared containing Amlodipine according to Table C-1. Each formulation was dispensed into screw-capped HDPE bottles and stored at both 5° C. and ambient temperature. Samples were removed periodically and analyzed using the HPLC method in Example A.

TABLE C-1

Composition (in mg/ml) of Amlodipine Formulations with Varying Hypromellose Content

| | Formulation | | | | | | | |
|---|---|---|---|---|---|---|---|---|
| Component | C1 | C2 | C3 | C4 | C5 | C6 | C7 | C8 |
| Amlodipine besylate [a] | 1.39 | 1.39 | 1.39 | 1.39 | 1.39 | 1.39 | 1.39 | 1.39 |
| Hypromellose K750 | 3.00 | 5.00 | 7.50 | 7.50 | — | — | — | — |
| Citric acid, anhydrous | 0.55 | 0.55 | 0.55 | 0.55 | 0.55 | 0.55 | 0.55 | 0.55 |
| Sodium benzoate | 5.00 | 5.00 | 5.00 | 5.00 | 5.00 | 5.00 | 5.00 | 5.00 |
| Sucralose | 0.70 | 0.70 | 0.70 | 0.70 | 0.70 | 0.70 | 0.70 | 0.70 |
| Simethicone | 0.15 | 0.15 | 0.15 | 0.15 | 0.15 | 0.15 | 0.15 | 0.15 |
| Silicon dioxide | 0.50 | | 0.50 | 0.50 | 0.50 | 0.50 | 0.50 | 0.50 |
| Artificial cherry flavor | — | — | — | 0.50 | — | 0.50 | — | 0.50 |
| Hypromellose K1500 | — | — | — | — | 3.00 | 5.00 | 7.50 | 7.50 |
| Water | q.s. | q.s. | q.s. | q.s. | q.s. | q.s. | q.s. | q.s. |
| pH | 4.88 | 4.88 | 4.86 | 4.89 | 4.88 | 4.88 | 4.87 | 4.91 |

[a] = equivalent to 1 mg/ml Amlodipine

The results of the HPLC analysis for amlodipine and the main degradants in the samples stored at 5° C. are provided in Table C-2.

TABLE C-2

Assay and Primary Degradants Present in the Formulations

| Weeks | Formulation | | | | | | | |
|---|---|---|---|---|---|---|---|---|
| | C1 | C2 | C3 | C4 | C5 | C6 | C7 | C8 |
| Amlodipine (% initial) | | | | | | | | |
| Initial | 100.00 | 100.00 | 100.00 | 100.00 | 100.00 | 100.00 | 100.00 | 100.00 |
| 4 | 100.00 | 97.18 | 99.17 | 98.39 | 97.30 | 98.96 | 97.08 | 98.08 |
| 8 | 100.49 | 98.81 | 99.23 | 98.67 | 96.88 | 98.32 | 96.76 | 98.17 |
| 12 | 99.72 | 99.17 | 100.27 | 99.57 | 95.76 | 98.49 | 97.42 | 98.95 |
| 26 | 99.46 | 99.89 | 98.00 | 98.64 | 92.35 | 97.30 | 96.94 | 97.96 |
| 52 | 95.73 | 96.34 | 98.91 | 99.67 | 96.59 | 100.29 | 97.44 | 96.27 |
| 78 | 98.78 | 98.10 | 98.74 | 99.14 | 99.39 | 97.91 | 97.48 | 95.92 |
| 104 | 97.56 | 97.33 | 98.54 | 97.56 | 95.74 | 96.98 | 97.94 | 99.09 |
| USP Impurity A/EP Impurity D (wt % of Amlodipine) | | | | | | | | |
| Initial | 0.01 | 0.03 | 0.01 | 0.16 | 0.02 | 0.10 | 0.02 | 0.11 |
| 4 | 0.01 | 0.02 | 0.03 | 0.17 | 0.02 | 0.11 | 0.03 | 0.10 |
| 8 | 0.03 | 0.03 | 0.03 | 0.21 | 0.02 | 0.11 | 0.04 | 0.12 |
| 12 | 0.03 | 0.04 | 0.04 | 0.21 | 0.03 | 0.10 | 0.04 | 0.11 |
| 26 | 0.02 | 0.05 | 0.05 | 0.26 | 0.03 | 0.11 | 0.06 | 0.15 |
| 52 | 0.06 | 0.04 | 0.07 | 0.35 | 0.06 | 0.14 | 0.07 | 0.20 |
| 78 | 0.06 | 0.11 | 0.11 | 0.41 | 0.07 | 0.18 | 0.10 | 0.24 |
| 104 | 0.09 | 0.13 | 0.11 | 0.32 | 0.09 | 0.13 | 0.13 | 0.19 |
| Impurity RRT 0.97 (wt % of Amlodipine) | | | | | | | | |
| Initial | 0.00 | 0.00 | 0.00 | 0.00 | 0.00 | 0.00 | 0.00 | 0.00 |
| 4 | 0.00 | 0.01 | 0.01 | 0.00 | 0.00 | 0.00 | 0.01 | 0.00 |
| 8 | 0.01 | 0.02 | 0.02 | 0.02 | 0.01 | 0.02 | 0.02 | 0.01 |
| 12 | 0.03 | 0.05 | 0.03 | 0.02 | 0.03 | 0.02 | 0.04 | 0.02 |
| 26 | 0.06 | 0.10 | 0.06 | 0.07 | 0.06 | 0.06 | 0.08 | 0.06 |
| 52 | 0.11 | 0.19 | 0.13 | 0.15 | 0.09 | 0.12 | 0.14 | 0.15 |
| 78 | 0.18 | 0.28 | 0.25 | 0.26 | 0.14 | 0.19 | 0.23 | 0.24 |
| 104 | 0.21 | 0.35 | 0.35 | 0.34 | 0.18 | 0.23 | 0.32 | 0.31 |
| Total Impurities (wt % of Amlodipine) | | | | | | | | |
| Initial | 0.05 | 0.10 | 0.14 | 0.27 | 0.06 | 0.18 | 0.22 | 0.21 |
| 4 | 0.07 | 0.07 | 0.08 | 0.28 | 0.08 | 0.16 | 0.10 | 0.16 |
| 8 | 0.08 | 0.10 | 0.10 | 0.34 | 0.06 | 0.20 | 0.10 | 0.22 |
| 12 | 0.10 | 0.13 | 0.12 | 0.35 | 0.10 | 0.21 | 0.14 | 0.23 |
| 26 | 0.16 | 0.22 | 0.18 | 0.51 | 0.16 | 0.29 | 0.25 | 0.34 |
| 52 | 0.25 | 0.37 | 0.31 | 0.74 | 0.24 | 0.42 | 0.33 | 0.55 |
| 78 | 0.44 | 0.54 | 0.49 | 1.00 | 0.37 | 0.58 | 0.51 | 0.76 |
| 104 | 0.46 | 0.73 | 0.61 | 1.02 | 0.44 | 0.65 | 0.63 | 0.80 |

The results of the HPLC analysis for amlodipine and the main degradants in the samples stored at ambient temperature are provided in Table C-3.

TABLE C-3

Assay and Primary Degradants Present in the Formulations

| Weeks | Formulation | | | | | | | |
|---|---|---|---|---|---|---|---|---|
| | C1 | C2 | C3 | C4 | C5 | C6 | C7 | C8 |
| Amlodipine (% initial) | | | | | | | | |
| Initial | 100.00 | 100.00 | 100.00 | 100.00 | 100.00 | 100.00 | 100.00 | 100.00 |
| 2 | 100.27 | 98.62 | 100.25 | 103.21 | 97.02 | 100.83 | 97.57 | 102.18 |
| 4 | 96.72 | 96.01 | 99.88 | 99.64 | 96.57 | 97.86 | 97.00 | 98.33 |
| 6 | 100.45 | 97.10 | — | 100.18 | 96.32 | 98.48 | — | 98.24 |
| 8 | 99.82 | 97.04 | 99.93 | 99.68 | 96.12 | 97.16 | 95.71 | 97.90 |
| 12 | 98.33 | 96.38 | 98.93 | 96.31 | 95.40 | 97.05 | 96.84 | 96.80 |
| 26 | 96.35 | 92.69 | 96.55 | 94.46 | 92.50 | 94.29 | 94.39 | 93.84 |
| USP Impurity A/EP Impurity D (wt % of Amlodipine) | | | | | | | | |
| Initial | 0.01 | 0.03 | 0.01 | 0.16 | 0.02 | 0.10 | 0.02 | 0.11 |
| 2 | 0.03 | 0.05 | 0.08 | 0.27 | 0.03 | 0.12 | 0.07 | 0.16 |
| 4 | 0.05 | 0.09 | 0.10 | 0.35 | 0.04 | 0.14 | 0.09 | 0.20 |

TABLE C-3-continued

Assay and Primary Degradants Present in the Formulations

| Weeks | C1 | C2 | C3 | C4 | C5 | C6 | C7 | C8 |
|---|---|---|---|---|---|---|---|---|
| 6 | 0.06 | 0.12 | — | 0.47 | 0.05 | 0.19 | — | 0.24 |
| 8 | 0.09 | 0.12 | 0.13 | 0.56 | 0.06 | 0.21 | 0.12 | 0.32 |
| 12 | 0.08 | 0.16 | 0.17 | 0.73 | 0.08 | 0.29 | 0.16 | 0.40 |
| 26 | 0.16 | 0.24 | 0.26 | 1.30 | 0.16 | 0.50 | 0.25 | 0.70 |
| Impurity RRT 0.97 (wt % of Amlodipine) | | | | | | | | |
| Initial | 0.00 | 0.00 | 0.00 | 0.00 | 0.00 | 0.00 | 0.00 | 0.00 |
| 2 | 0.05 | 0.09 | 0.10 | 0.08 | 0.05 | 0.07 | 0.09 | 0.08 |
| 4 | 0.13 | 0.22 | 0.20 | 0.19 | 0.12 | 0.17 | 0.17 | 0.19 |
| 6 | 0.20 | 0.33 | — | 0.30 | 0.17 | 0.24 | — | 0.29 |
| 8 | 0.24 | 0.40 | 0.40 | 0.41 | 0.21 | 0.30 | 0.33 | 0.37 |
| 12 | 0.32 | 0.51 | 0.58 | 0.58 | 0.26 | 0.38 | 0.49 | 0.50 |
| 26 | 0.38 | 0.60 | 0.89 | 0.91 | 0.30 | 0.47 | 0.69 | 0.69 |
| Total Impurities (wt % of Amlodipine) | | | | | | | | |
| Initial | 0.05 | 0.10 | 0.14 | 0.27 | 0.06 | 0.18 | 0.22 | 0.21 |
| 2 | 0.16 | 0.26 | 0.26 | 0.50 | 0.16 | 0.36 | 0.23 | 0.44 |
| 4 | 0.34 | 0.48 | 0.43 | 0.80 | 0.31 | 0.52 | 0.37 | 0.60 |
| 6 | 0.41 | 0.69 | — | 1.10 | 0.42 | 0.69 | — | 0.79 |
| 8 | 0.54 | 0.81 | 0.72 | 1.44 | 0.53 | 0.87 | 0.64 | 1.06 |
| 12 | 0.70 | 1.06 | 1.02 | 1.90 | 0.66 | 1.15 | 0.94 | 1.40 |
| 26 | 1.02 | 1.45 | 1.64 | 3.40 | 1.00 | 1.97 | 1.44 | 2.45 |

Example D

Effect of Povidone on the Formation of Degradants in Amlodipine Formulations

Formulations were prepared containing Amlodipine according to Table D-1. Each formulation was dispensed into screw-capped HDPE bottles and stored at both 5° C. and ambient temperature. Samples were removed periodically and analyzed using the HPLC method in Example A.

TABLE D-1

Composition (in mg/ml) of Amlodipine Formulations with Varying Povidone Content

| Component | D1 | D2 | D3 | D4 | D5 | D6 |
|---|---|---|---|---|---|---|
| Amlodipine besylate [a] | 1.39 | 1.39 | 1.39 | 1.39 | 1.39 | 1.39 |
| Hypromellose K750 | — | — | — | — | — | 3.00 |
| Citric acid, anhydrous | 0.90 | 0.90 | 0.90 | 0.55 | 0.43 | 0.55 |
| Sodium benzoate | 7.50 | 7.50 | 7.50 | 5.00 | 3.00 | 5.00 |
| Sucralose | 0.70 | 0.70 | 0.70 | 0.70 | 0.70 | 0.70 |
| Simethicone | — | — | — | — | — | 0.15 |
| Silicon dioxide | 0.50 | 0.50 | 0.50 | 0.50 | 0.50 | 0.50 |
| K-90 Povidone | 10.00 | 20.00 | 30.00 | 30.00 | 30.00 | 10.00 |
| Water | q.s. | q.s. | q.s. | q.s. | q.s. | q.s. |
| pH | 4.87 | 4.89 | 4.92 | 4.96 | 4.83 | 4.91 |

[a] = equivalent to 1 mg/ml Amlodipine

The results of the HPLC analysis for amlodipine and the main degradants in the samples stored at 5° C. are provided in Table D-2.

TABLE D-2

Assay and Primary Degradants Present in the Formulations

| | Formulation | | | | | |
|---|---|---|---|---|---|---|
| Weeks | D1 | D2 | D3 | D4 | D5 | D6 |
| Amlodipine (% initial) | | | | | | |
| Initial | 100.00 | 100.00 | 100.00 | 100.00 | 100.00 | 100.00 |
| 4 | 95.19 | 99.46 | 99.87 | 99.23 | 101.99 | 97.83 |
| 8 | 96.51 | 98.13 | 99.21 | 96.18 | 102.95 | 99.57 |
| 12 | 96.40 | 96.19 | 97.81 | 91.38 | 101.78 | 97.16 |
| 26 | 97.22 | 98.13 | 100.19 | 100.70 | 97.51 | 100.40 |
| 52 | 94.66 | 96.70 | 99.27 | 89.30 | 93.84 | 99.65 |
| 78 | 96.81 | 98.79 | 99.53 | 98.55 | 89.66 | 100.84 |
| 104 | 94.89 | 99.34 | 99.50 | 98.92 | 94.48 | 97.93 |
| USP Impurity A/EP Impurity D (wt % of Amlodipine) | | | | | | |
| Initial | 0.03 | 0.06 | 0.05 | 0.06 | 0.03 | 0.02 |
| 4 | 0.07 | 0.04 | 0.06 | 0.06 | 0.05 | 0.04 |
| 8 | 0.04 | 0.07 | 0.06 | 0.07 | 0.07 | 0.05 |
| 12 | 0.05 | 0.06 | 0.05 | 0.06 | 0.06 | 0.08 |
| 26 | 0.04 | 0.03 | 0.07 | 0.08 | 0.09 | 0.05 |
| 52 | 0.04 | 0.04 | 0.06 | 0.08 | 0.07 | 0.07 |
| 78 | 0.05 | 0.06 | 0.07 | 0.09 | 0.11 | 0.08 |
| 104 | 0.07 | 0.07 | 0.08 | 0.11 | 0.12 | 0.09 |
| Impurity RRT 0.97 (wt % of Amlodipine) | | | | | | |
| Initial | 0.00 | 0.00 | 0.00 | 0.00 | 0.00 | 0.00 |
| 4 | 0.00 | 0.00 | 0.00 | 0.00 | 0.00 | 0.00 |
| 8 | 0.00 | 0.00 | 0.00 | 0.00 | 0.00 | 0.01 |
| 12 | 0.00 | 0.00 | 0.00 | 0.00 | 0.00 | 0.01 |
| 26 | 0.00 | 0.00 | 0.01 | 0.01 | 0.02 | 0.05 |
| 52 | 0.01 | 0.01 | 0.02 | 0.02 | 0.03 | 0.10 |
| 78 | 0.01 | 0.02 | 0.03 | 0.04 | 0.05 | 0.14 |
| 104 | 0.02 | 0.03 | 0.04 | 0.05 | 0.07 | 0.21 |
| Total Impurities (wt % of Amlodipine) | | | | | | |
| Initial | 0.09 | 0.11 | 0.10 | 0.09 | 0.07 | 0.07 |
| 4 | 0.11 | 0.08 | 0.10 | 0.12 | 0.10 | 0.08 |
| 8 | 0.10 | 0.14 | 0.10 | 0.12 | 0.12 | 0.10 |
| 12 | 0.18 | 0.17 | 0.21 | 0.12 | 0.13 | 0.14 |
| 26 | 0.11 | 0.16 | 0.18 | 0.16 | 0.19 | 0.16 |
| 52 | 0.17 | 0.15 | 0.24 | 0.16 | 0.20 | 0.21 |
| 78 | 0.14 | 0.16 | 0.20 | 0.20 | 0.28 | 0.31 |
| 104 | 0.18 | 0.20 | 0.23 | 0.31 | 0.33 | 0.43 |

The results of the HPLC analysis for amlodipine and the main degradants in the samples stored at ambient temperature are provided in Table D-3.

TABLE D-3

Assay and Primary Degradants Present in the Formulations

| | Formulation | | | | | |
|---|---|---|---|---|---|---|
| Weeks | D1 | D2 | D3 | D4 | D5 | D6 |
| Amlodipine (% initial) | | | | | | |
| Initial | 100.00 | 100.00 | 100.00 | 100.00 | 100.00 | 100.00 |
| 2 | 94.21 | 97.15 | 98.15 | 91.04 | 99.93 | 99.36 |
| 4 | 95.69 | 97.67 | 99.15 | 99.49 | 99.87 | 97.93 |
| 6 | 95.18 | 97.15 | 97.20 | 97.49 | 101.11 | 98.11 |
| 8 | 94.74 | 96.16 | 96.17 | 98.99 | 98.59 | 99.38 |
| 12 | 91.38 | 95.07 | 95.50 | 97.35 | 96.85 | 96.51 |
| 26 | 93.65 | 92.14 | 93.58 | 96.84 | 92.72 | 96.77 |
| USP Impurity A/EP Impurity D (wt % of Amlodipine) | | | | | | |
| Initial | 0.03 | 0.06 | 0.05 | 0.06 | 0.03 | 0.02 |
| 2 | 0.06 | 0.07 | 0.08 | 0.12 | 0.10 | 0.10 |
| 4 | 0.07 | 0.08 | 0.08 | 0.12 | 0.13 | 0.10 |
| 6 | 0.08 | 0.11 | 0.10 | 0.16 | — | 0.12 |
| 8 | 0.08 | 0.10 | 0.12 | 0.17 | 0.17 | 0.15 |
| 12 | 0.10 | 0.15 | 0.13 | 0.21 | 0.25 | 0.18 |
| 26 | 0.16 | 0.21 | 0.26 | 0.34 | 0.44 | 0.31 |
| Impurity RRT 0.97 (wt % of Amlodipine) | | | | | | |
| Initial | 0.00 | 0.00 | 0.00 | 0.00 | 0.00 | 0.00 |
| 2 | 0.00 | 0.01 | 0.02 | 0.01 | 0.01 | 0.05 |
| 4 | 0.02 | 0.03 | 0.05 | 0.04 | 0.05 | 0.13 |
| 6 | 0.03 | 0.04 | 0.06 | 0.06 | — | 0.20 |
| 8 | 0.04 | 0.06 | 0.08 | 0.08 | 0.08 | 0.25 |
| 12 | 0.04 | 0.07 | 0.09 | 0.09 | 0.10 | 0.32 |
| 26 | 0.05 | 0.10 | 0.13 | 0.13 | 0.14 | 0.41 |
| Total Impurities (wt % of Amlodipine) | | | | | | |
| Initial | 0.09 | 0.11 | 0.10 | 0.09 | 0.07 | 0.07 |
| 2 | 0.17 | 0.19 | 0.20 | 0.25 | 0.26 | 0.24 |
| 4 | 0.27 | 0.26 | 0.31 | 0.37 | 0.44 | 0.38 |
| 6 | 0.30 | 0.36 | 0.38 | 0.48 | — | 0.50 |
| 8 | 0.25 | 0.47 | 0.49 | 0.51 | 0.64 | 0.61 |
| 12 | 0.48 | 0.60 | 0.60 | 0.60 | 0.74 | 0.70 |
| 26 | 0.59 | 0.82 | 1.07 | 1.29 | 1.83 | 1.47 |

Example E

Formulations Containing 2-Naphthalene Sulfonate Salt Form of Amlodipine

Formulations were prepared containing Amlodipine according to Table E-1. Each formulation was dispensed into screw-capped HDPE bottles and stored at both ambient temperature and 40° C. Samples were removed periodically and analyzed using the HPLC method in Example A.

TABLE E-1

Composition (in mg/ml) of Amlodipine Formulations

| | Formulation | | |
|---|---|---|---|
| Component | E1 | E2 | E3 |
| Amlodipine besylate [a] | 1.39 | 1.39 | 1.39 |
| Sodium 2-naphthalene sulfonate | 1.13 | 1.13 | 2.26 |
| Citric acid, anhydrous | 0.31 | 0.31 | 0.31 |
| Sodium citrate | 0.42 | 0.42 | 0.42 |
| Sodium benzoate | 1.00 | 1.00 | 1.00 |
| Sucralose | 0.70 | 0.70 | 0.70 |
| Simethicone | 0.15 | 0.15 | 0.15 |
| Silicon dioxide | 0.50 | 0.50 | 0.50 |
| Artificial cherry flavor | — | 0.50 | — |
| Red 40 Al lake color | — | 0.015 | — |
| Hypromellose K750 | 5.00 | 5.00 | 5.00 |
| Water | q.s. | q.s. | q.s. |
| pH | 5.09 | 5.10 | 5.08 |

[a] = equivalent to 1 mg/ml Amlodipine

The results of the HPLC analysis for amlodipine and the main degradants in the samples stored at ambient temperature are provided in Table E-2.

TABLE E-2

Assay and Primary Degradants Present in the Formulations

| Weeks | Formulation | | |
|---|---|---|---|
| | E1 | E2 | E3 |
| Amlodipine (% initial) | | | |
| Initial | 100.00 | 100.00 | 100.00 |
| 4 | 98.82 | 99.90 | 100.13 |
| 8 | 98.02 | 99.22 | 99.78 |
| 12 | 98.62 | 99.66 | 99.76 |
| 26 | 97.56 | 98.86 | 99.99 |
| 52 | 98.80 | 100.17 | 99.51 |
| 78 | 98.46 | 100.15 | 100.21 |
| 104 | 98.36 | 100.38 | 102.36 |
| USP Impurity A/EP Impurity D (wt % of Amlodipine) | | | |
| Initial | 0.06 | 0.03 | 0.02 |
| 4 | 0.04 | 0.04 | 0.04 |
| 8 | 0.04 | 0.04 | 0.04 |
| 12 | 0.05 | 0.05 | 0.06 |
| 26 | 0.09 | 0.07 | 0.08 |
| 52 | 0.14 | 0.12 | 0.14 |
| 78 | 0.21 | 0.17 | 0.16 |
| 104 | 0.26 | 0.22 | 0.22 |
| Impurity RRT 0.97 (wt % of Amlodipine) | | | |
| Initial | 0.00 | 0.00 | 0.00 |
| 4 | 0.01 | 0.01 | 0.00 |
| 8 | 0.02 | 0.02 | 0.00 |
| 12 | 0.03 | 0.03 | 0.01 |
| 26 | 0.06 | 0.07 | 0.03 |
| 52 | 0.13 | 0.13 | 0.05 |
| 78 | 0.18 | 0.19 | 0.07 |
| 104 | 0.23 | 0.24 | 0.09 |
| Total Impurities (wt % of Amlodipine) | | | |
| Initial | 0.31 | 0.51 | 0.45 |
| 4 | 0.10 | 0.10 | 0.08 |
| 8 | 0.10 | 0.09 | 0.13 |
| 12 | 0.12 | 0.12 | 0.12 |
| 26 | 0.23 | 0.26 | 0.17 |
| 52 | 0.42 | 0.36 | 0.36 |
| 78 | 0.50 | 0.48 | 0.31 |
| 104 | 0.69 | 0.60 | 0.54 |

The results of the HPLC analysis for amlodipine and the main degradants in the samples stored at 40° C. are provided in Table E-3.

TABLE E-3

Assay and Primary Degradants Present in the Formulations

| Weeks | Formulation | | |
|---|---|---|---|
| | E1 | E2 | E3 |
| Amlodipine (% initial) | | | |
| Initial | 100.00 | 100.00 | 100.00 |
| 2 | 98.23 | 98.65 | 98.59 |
| 4 | 98.20 | 98.67 | 99.41 |
| 8 | 95.28 | 97.08 | 97.82 |
| 12 | 94.44 | 95.59 | 97.12 |
| 26 | 87.62 | 90.88 | 91.30 |

TABLE E-3-continued

Assay and Primary Degradants Present in the Formulations

| Weeks | Formulation | | |
|---|---|---|---|
| | E1 | E2 | E3 |
| USP Impurity A/EP Impurity D (wt % of Amlodipine) | | | |
| Initial | 0.06 | 0.03 | 0.02 |
| 2 | 0.13 | 0.12 | 0.12 |
| 4 | 0.20 | 0.19 | 0.19 |
| 8 | 0.42 | 0.33 | 0.44 |
| 12 | 0.67 | 0.47 | 0.87 |
| 26 | 1.95 | 1.06 | 5.18 |
| Impurity RRT 0.97 (wt % of Amlodipine) | | | |
| Initial | 0.00 | 0.00 | 0.00 |
| 2 | 0.11 | 0.12 | 0.05 |
| 4 | 0.19 | 0.20 | 0.09 |
| 8 | 0.32 | 0.33 | 0.15 |
| 12 | 0.38 | 0.39 | 0.20 |
| 26 | 0.41 | 0.41 | 0.20 |
| Total Impurities (wt % of Amlodipine) | | | |
| Initial | 0.31 | 0.51 | 0.45 |
| 2 | 0.40 | 0.41 | 0.32 |
| 4 | 0.63 | 0.66 | 0.53 |
| 8 | 1.20 | 1.10 | 1.06 |
| 12 | 1.80 | 1.78 | 1.83 |
| 26 | 4.07 | 3.21 | 8.22 |

Example F

Stability of Amlodipine Formulations Prepared by Two-Container, One-Container, and Pharmacy Compounding Processes Formulation F6 was prepared by crushing 50 commercially available 5 mg amlodipine besylate tablets (Norvasc®, Pfizer Labs) with a mortar and pestle. A small amount of Ora-Blend (Paddock Laboratories, Inc.) was triturated with the resulting powder, and then more Ora-Blend was added geometrically with mixing. The suspension was transferred to a graduated cylinder and the mortar was rinsed with Ora-Blend. The rinse was added to the cylinder then additional Ora-Blend was added to reach a final volume of 250 ml and the suspension was mixed. Formulations F1, F2, and F3 were prepared according to example 5B (one-container) and formulations F4 and F5 were prepared according to example 3A (two-container).

Each formulation was dispensed into screw-capped HDPE bottles and stored at both 5° C. and ambient temperature. Samples were removed periodically and analyzed using the HPLC method in Example A.

TABLE F-1

Composition (in mg/mL) of Amlodipine Formulations

| Component | F1 | F2 | F3 | F4 | F5 | F6 |
|---|---|---|---|---|---|---|
| Amlodipine besylate [a] | 1.39 | 1.39 | 1.39 | 1.39 | 1.39 | 50 tablets |
| Citric acid, anhydrous | 0.31 | 0.31 | 0.31 | 0.31 | 0.31 | — |
| Sodium citrate, anhydrous | 0.36 | 0.36 | 0.36 | 0.36 | 0.36 | — |
| Sodium benzoate | 5.00 | 5.00 | 5.00 | 5.00 | 5.00 | — |
| Sucralose | 0.70 | 0.70 | 0.70 | 0.70 | 0.70 | — |
| Simethicone | 0.15 | 0.15 | 0.15 | 0.15 | 0.15 | — |
| Silicon dioxide | 0.50 | 0.50 | 0.50 | 0.50 | 0.50 | — |
| Artificial cherry flavor | 0.50 | 0.50 | 0.50 | 0.50 | — | — |
| Polysorbate 80 | 0.50 | 1.00 | 2.00 | 1.00 | 1.00 | — |
| 0Hypromellose K1500 | 5.00 | 5.00 | 5.00 | 7.50 | 7.50 | — |
| Water | q.s. | q.s. | q.s. | q.s. | q.s. | — |
| Ora-Blend ™ | — | — | — | — | — | q.s. to 250 ml |
| pH | 5.31 | 5.33 | 5.35 | 5.35 | 5.36 | 4.64 |

[a] = equivalent to 1 mg/ml Amlodipine

The results of the HPLC analysis for amlodipine and the main degradants in the samples stored at 5° C. are provided in Table F-2.

TABLE F-2

Assay and Primary Degradants Present in the Formulations

| Weeks | F1 | F2 | F3 | F4 | F5 | F6 |
|---|---|---|---|---|---|---|
| | Amlodipine (% initial) | | | | | |
| Initial | 100.00 | 100.00 | 100.00 | 100.00 | 100.00 | 100.0 |
| 2 | 99.23 | 100.74 | 99.17 | — | 101.85 | — |
| 4 | — | — | — | 100.37 | 101.69 | 100.3 |
| 6 | 98.98 | 101.53 | 99.72 | — | 101.09 | — |
| 8 | 99.70 | 100.86 | 99.06 | 101.12 | 101.40 | 97.2 |
| 12 | 98.98 | 100.49 | 98.91 | 100.35 | 101.12 | |
| 26 | 101.14 | 100.91 | 100.20 | 100.26 | | |
| 52 | 99.69 | 100.87 | 99.85 | 101.52 | | |
| 78 | 97.82 | 99.94 | 98.94 | 101.72 | | |
| 104 | 99.74 | 99.90 | 98.19 | | | |
| | USP Impurity A/EP Impurity D (wt % of Amlodipine) | | | | | |
| Initial | 0.04 | 0.06 | 0.04 | 0.01 | 0.00 | 1.34 |
| 2 | 0.00 | 0.00 | 0.01 | — | 0.02 | — |
| 4 | — | — | — | 0.01 | 0.03 | 0.71 |
| 6 | 0.04 | 0.02 | 0.02 | — | 0.03 | — |
| 8 | 0.01 | 0.02 | 0.02 | 0.03 | 0.05 | 1.24 |
| 12 | 0.03 | 0.02 | 0.02 | 0.10 | 0.04 | |
| 26 | 0.05 | 0.06 | 0.06 | 0.05 | | |
| 52 | 0.04 | 0.04 | 0.05 | 0.07 | | |
| 78 | 0.06 | 0.05 | 0.06 | 0.04 | | |
| 104 | 0.04 | 0.04 | 0.06 | | | |

TABLE F-2-continued

Assay and Primary Degradants Present in the Formulations

| Weeks | F1 | F2 | F3 | F4 | F5 | F6 |
|---|---|---|---|---|---|---|
| | Impurity RRT 0.97 (wt % of Amlodipine) | | | | | |
| Initial | 0.00 | 0.00 | 0.00 | 0.00 | 0.00 | 0.00 |
| 2 | 0.00 | 0.00 | 0.00 | — | 0.00 | — |
| 4 | — | — | — | 0.00 | 0.00 | 0.00 |
| 6 | 0.00 | 0.00 | 0.00 | — | 0.01 | — |
| 8 | 0.00 | 0.00 | 0.00 | 0.01 | 0.01 | 0.00 |
| 12 | 0.01 | 0.00 | 0.01 | 0.02 | 0.03 | |
| 26 | 0.04 | 0.04 | 0.04 | 0.05 | | |
| 52 | 0.09 | 0.09 | 0.11 | 0.11 | | |
| 78 | 0.14 | 0.15 | 0.16 | 0.20 | | |
| 104 | 0.19 | 0.20 | 0.22 | | | |
| | Total Impurities (wt % of Amlodipine) | | | | | |
| Initial | 0.09 | 0.14 | 0.11 | 0.04 | 0.00 | 1.76 |
| 2 | 0.04 | 0.03 | 0.06 | — | 0.06 | — |
| 4 | — | — | — | 0.04 | 0.08 | 1.00 |
| 6 | 0.07 | 0.05 | 0.06 | — | 0.09 | — |
| 8 | 0.05 | 0.06 | 0.07 | 0.06 | 0.08 | 1.52 |
| 12 | 0.08 | 0.05 | 0.06 | 0.19 | 0.09 | |
| 26 | 0.12 | 0.13 | 0.14 | 0.13 | | |
| 52 | 0.23 | 0.22 | 0.29 | 0.31 | | |
| 78 | 0.42 | 0.40 | 0.45 | 0.43 | | |
| 104 | 0.41 | 0.44 | 0.53 | | | |

The results of the HPLC analysis for amlodipine and the main degradants in the samples stored at ambient temperature are provided in Table F-3.

TABLE F-3

Assay and Primary Degradants Present in the Formulations

| Weeks | F1 | F2 | F3 | F4 | F5 | F6 |
|---|---|---|---|---|---|---|
| | Amlodipine (% initial) | | | | | |
| Initial | 100.00 | 100.00 | 100.00 | 100.00 | 100.00 | 100.0 |
| 2 | 100.65 | 100.52 | 99.57 | 101.16 | 100.89 | 97.7 |
| 4 | — | — | — | 99.99 | 100.41 | 102.1 |
| 6 | 100.23 | 100.42 | 98.78 | 100.38 | 100.47 | 94.3 |
| 8 | 99.16 | 100.28 | 98.99 | 102.38 | 100.68 | 90.6 |
| 12 | 99.71 | 99.46 | 98.52 | 100.53 | 99.44 | |
| 26 | 98.13 | 98.53 | 97.24 | 97.27 | | |

TABLE F-3-continued

Assay and Primary Degradants Present in the Formulations

| Weeks | F1 | F2 | F3 | F4 | F5 | F6 |
|---|---|---|---|---|---|---|
| USP Impurity A/EP Impurity D (wt % of Amlodipine) | | | | | | |
| Initial | 0.04 | 0.06 | 0.04 | 0.01 | 0.00 | 1.34 |
| 2 | 0.05 | 0.04 | 0.05 | 0.04 | 0.05 | 1.62 |
| 4 | — | — | — | 0.05 | 0.06 | 2.24 |
| 6 | 0.06 | 0.06 | 0.07 | 0.09 | 0.08 | 2.78 |
| 8 | 0.07 | 0.06 | 0.08 | 0.10 | 0.11 | 3.24 |
| 12 | 0.10 | 0.09 | 0.10 | 0.15 | 0.13 | |
| 26 | 0.18 | 0.17 | 0.18 | 0.24 | | |
| Impurity RRT 0.97 (wt % of Amlodipine) | | | | | | |
| Initial | 0.00 | 0.00 | 0.00 | 0.00 | 0.00 | 0.00 |
| 2 | 0.03 | 0.03 | 0.04 | 0.03 | 0.04 | 0.03 |
| 4 | — | — | — | 0.06 | 0.10 | 0.05 |
| 6 | 0.12 | 0.13 | 0.13 | 0.11 | 0.13 | 0.09 |
| 8 | 0.17 | 0.17 | 0.17 | 0.17 | 0.18 | 0.11 |
| 12 | 0.23 | 0.23 | 0.24 | 0.28 | 0.30 | |
| 26 | 0.36 | 0.35 | 0.36 | 0.49 | | |
| Total Impurities (wt % of Amlodipine) | | | | | | |
| Initial | 0.09 | 0.14 | 0.11 | 0.04 | 0.00 | 1.76 |
| 2 | 0.16 | 0.16 | 0.17 | 0.10 | 0.18 | 2.09 |
| 4 | — | — | — | 0.24 | 0.37 | 3.09 |
| 6 | 0.39 | 0.38 | 0.43 | 0.38 | 0.50 | 4.20 |
| 8 | 0.46 | 0.48 | 0.52 | 0.51 | 0.64 | 5.05 |
| 12 | 0.69 | 0.68 | 0.76 | 0.85 | 1.02 | |
| 26 | 1.26 | 1.38 | 1.47 | 1.65 | | |

Example G

Effect of pH, Preservatives, and Hypromellose on Stability of Amlodipine Benzoate Formulations at Accelerated Temperatures Formulations were prepared containing Amlodipine according to Table G-1. Each formulation was dispensed into screw-capped HDPE bottles and stored at 60° C. Samples were removed periodically and analyzed using the HPLC method in Example A.

TABLE G-1

Composition (in mg/mL) of Amlodipine Formulations

| Component | G1 | G2 | G3 | G4 | G5 | G6 | G7 | G8 |
|---|---|---|---|---|---|---|---|---|
| Amlodipine besylate [a] | 1.39 | 1.39 | 1.39 | 1.39 | 1.39 | 1.39 | 1.39 | 1.39 |
| Citric acid, anhydrous | 11.66 | 0.33 | 0.71 | — | — | — | 0.31 | 0.31 |
| Sodium citrate, anhydrous | — | 0.35 | — | — | — | — | 0.36 | 0.36 |
| Phosphoric acid | — | — | — | 0.96 | 0.67 | 0.39 | — | — |
| Sodium benzoate | 5.0 | 5.0 | 5.0 | 5.0 | 5.0 | 5.0 | 5.0 | 5.0 |
| Sucralose | 0.7 | 0.7 | 0.7 | 0.7 | 0.7 | 0.7 | 0.7 | 0.7 |
| Methylparaben sodium | — | — | 1.72 | 1.72 | 1.72 | 1.72 | — | — |
| Propylparaben sodium | — | — | 0.17 | 0.17 | 0.17 | 0.17 | — | — |
| Simethicone | 0.15 | 0.15 | 0.15 | 0.15 | 0.15 | 0.15 | 0.15 | 0.15 |
| Silicon dioxide | 0.5 | 0.5 | 0.5 | 0.5 | 0.5 | 0.5 | 0.5 | 0.5 |
| Artificial cherry flavor | 0.5 | 0.5 | 0.5 | 0.5 | 0.5 | 0.5 | — | — |
| Polysorbate 80 | 1.0 | 1.0 | 1.0 | 1.0 | 1.0 | 1.0 | 1.0 | 1.0 |
| Hypromellose K1500 | 5.0 | 5.0 | 5.0 | 5.0 | 5.0 | 5.0 | 7.5 | 10.0 |
| Water | q.s. | q.s. | q.s. | q.s. | q.s. | q.s. | q.s. | q.s |
| pH | 3.0 | 5.3 | 6.4 | 6.4 | 7.2 | 8.0 | 5.4 | 5.4 |

[a] = equivalent to 1 mg/ml Amlodipine

The results of the HPLC analysis for amlodipine and the main degradants in the samples are provided in Table G-2.

TABLE G-2

Assay and Primary Degradants Present in the Formulations

| Hours | G1 | G2 | G3 | G4 | G5 | G6 | G7 | G8 |
|---|---|---|---|---|---|---|---|---|
| Amlodipine (% initial) ||||||||
| 0 | 100.00 | 100.00 | 100.00 | 100.00 | 100.00 | 100.00 | 100.00 | 100.00 |
| 16 | 79.51 | 94.37 | 93.87 | 92.75 | 91.50 | 85.26 | — | — |
| 17 | — | — | — | — | — | — | 93.42 | 96.47 |
| 36 | — | — | — | — | — | — | 90.28 | — |
| 40 | 66.39 | 91.31 | 91.68 | 92.04 | 85.87 | 75.43 | — | — |
| 52 | — | — | — | — | — | — | 87.31 | 89.50 |
| USP Impurity A/EP Impurity D (wt % of Amlodipine) ||||||||
| 0 | 0.20 | 0.03 | 0.03 | 0.03 | 0.06 | 0.03 | 0.03 | 0.01 |
| 16 | 2.39 | 0.16 | 0.14 | 0.24 | 0.24 | 0.21 | — | — |
| 17 | — | — | — | — | — | — | 0.18 | 0.18 |
| 36 | — | — | — | — | — | — | 0.29 | — |
| 40 | 4.24 | 0.29 | 0.21 | 0.35 | 0.34 | 0.35 | — | — |
| 52 | — | — | — | — | — | — | 0.58 | 0.50 |
| Impurity RRT 0.97 (wt % of Amlodipine) ||||||||
| 0 | 0.00 | 0.00 | 0.00 | 0.00 | 0.00 | 0.00 | 0.04 | 0.00 |
| 16 | 0.37 | 0.16 | 0.07 | 0.03 | 0.04 | 0.05 | — | — |
| 17 | — | — | — | — | — | — | 0.21 | 0.20 |
| 36 | — | — | — | — | — | — | 0.44 | — |
| 40 | 0.52 | 0.30 | 0.15 | 0.08 | 0.08 | 0.13 | — | — |
| 52 | | | | | | | 0.54 | 0.62 |
| Total Impurities (wt % of Amlodipine) ||||||||
| 0 | 0.48 | 0.08 | 0.19 | 0.23 | 0.43 | 0.72 | 0.10 | 0.08 |
| 16 | 7.86 | 1.36 | 1.38 | 1.18 | 2.06 | 3.22 | — | — |
| 17 | — | — | — | — | — | — | 1.43 | 1.41 |
| 36 | — | — | — | — | — | — | 3.12 | — |
| 40 | 14.22 | 2.79 | 2.53 | 2.41 | 3.88 | 5.94 | — | — |
| 52 | — | — | — | — | — | — | 4.82 | 4.65 |

Example H

Effect of pH and Preservatives on Stability of Amlodipine Naphthalene Sulfonate Formulations at Accelerated Temperatures Formulations were prepared containing Amlodipine according to Table H-1. Each formulation was dispensed into screw-capped HDPE bottles and stored at 60° C. Samples were removed periodically and analyzed using the HPLC method in Example A.

TABLE H-1

Composition (in mg/mL) of Amlodipine Formulations

| Component | H1 | H2 | H3 | H4 | H5 | H6 |
|---|---|---|---|---|---|---|
| Amlodipine besylate [a] | 1.39 | 1.39 | 1.39 | 1.39 | 1.39 | 1.39 |
| Citric acid, anhydrous | 2.92 | 0.73 | 0.28 | — | — | — |
| Sodium citrate, anhydrous | — | — | 0.41 | — | — | — |
| Phosphoric acid | — | — | — | 1.28 | 0.85 | 0.30 |
| Dibasic sodium phosphate, heptahydrate | — | — | — | 0.31 | — | 0.18 |
| Sodium benzoate | 1.0 | 1.0 | 1.0 | — | — | — |
| Sodium 2-naphthalene sulfonate | 1.13 | 1.13 | 1.13 | 1.13 | 1.13 | 1.13 |
| Sucralose | 0.7 | 0.7 | 0.7 | 0.7 | 0.7 | 0.7 |
| Methylparaben sodium | — | — | — | 1.72 | 1.72 | 1.72 |
| Propylparaben sodium | — | — | — | 0.17 | 0.17 | 0.17 |
| Simethicone | 0.15 | 0.15 | 0.15 | 0.15 | 0.15 | 0.15 |
| Silicon dioxide | 0.5 | 0.5 | 0.5 | 0.5 | 0.5 | 0.5 |
| Artificial cherry flavor | 0.5 | 0.5 | 0.5 | 0.5 | 0.5 | 0.5 |

TABLE H-1-continued

Composition (in mg/mL) of Amlodipine Formulations

| Component | Formulation | | | | | |
|---|---|---|---|---|---|---|
| | H1 | H2 | H3 | H4 | H5 | H6 |
| Polysorbate 80 | 1.0 | 1.0 | 1.0 | 1.0 | 1.0 | 1.0 |
| Hypromellose K1500 | 5.0 | 5.0 | 5.0 | 5.0 | 5.0 | 5.0 |
| Water | q.s. | q.s. | q.s. | q.s. | q.s. | q.s. |
| pH | 3.0 | 4.0 | 5.0 | 5.9 | 6.9 | 7.9 |

The results of the HPLC analysis for amlodipine and the main degradants in the samples are provided in Table H-2.

TABLE H-2

Assay and Primary Degradants Present in the Formulations

| Hours | Formulation | | | | | |
|---|---|---|---|---|---|---|
| | H1 | H2 | H3 | H4 | H5 | H6 |
| | Amlodipine (% initial) | | | | | |
| 0 | 100.00 | 100.00 | 100.00 | 100.00 | 100.00 | 100.00 |
| 16 | 90.01 | 96.31 | 97.94 | 99.10 | 99.76 | 92.65 |
| 40 | 69.77 | 85.46 | 90.42 | 95.03 | 91.15 | 65.16 |
| | USP Impurity A/EP Impurity D (wt % of Amlodipine) | | | | | |
| 0 | 0.07 | 0.03 | 0.04 | 0.08 | 0.06 | 0.23 |
| 16 | 1.44 | 0.33 | 0.14 | 0.37 | 0.42 | 0.40 |
| 40 | 4.98 | 2.65 | 1.01 | 0.88 | 0.75 | 1.14 |
| | Impurity RRT 0.97 (wt % of Amlodipine) | | | | | |
| 0 | 0.00 | 0.00 | 0.00 | 0.00 | 0.00 | 0.00 |
| 16 | 0.15 | 0.20 | 0.11 | 0.00 | 0.02 | 0.05 |
| 40 | 0.38 | 0.52 | 0.31 | 0.02 | 0.07 | 0.05 |
| | Total Impurities (wt % of Amlodipine) | | | | | |
| 0 | 0.13 | 0.09 | 0.25 | 1.09 | 2.92 | 5.57 |
| 16 | 3.44 | 1.17 | 0.81 | 1.76 | 3.04 | 13.64 |
| 40 | 10.82 | 5.76 | 3.39 | 3.21 | 6.92 | 35.53 |

Example I

Effect of Crystallization Time on the Formation of Amlodipine Salts

A formulation was prepared in a polyethylene vessel with magnetic stirring. Purified water (33.5 kg) was added to the vessel and stirring was initiated. Polysorbate 80 (350 g) was added to the vessel along with a 500 g aliquot of purified water used to rinse the polysorbate container. The solution was stirred for 10 minutes. Amlodipine Besylate (485.5 g) was then added to the vessel along with a 500 g aliquot of purified water used to rinse the amlodipine container. The solution was stirred for 5 minutes then 1750 g of sodium benzoate were added to the container.

Samples were taken from the formulation every five minutes for an hour, filtered through 0.2 micron filters to isolate only the soluble amlodipine, and analyzed by HPLC for amlodipine content. The results of the HPLC analysis for the free amlodipine fraction are provided in FIG. 1.

Example J

Stability of Formulations Using Avicel® RC-591 as the Suspending Agent

Formulations were prepared containing Amlodipine according to Table J-1. Each formulation was dispensed into screw-capped HDPE bottles and stored at both 5° C. and 25° C. Samples were removed periodically and analyzed using the HPLC method in Example A.

TABLE J-1

Composition (in mg/ml) of Amlodipine Formulations

| Component | Formulation | | |
|---|---|---|---|
| | J1 | J2 | J3 |
| Amlodipine besylate [a] | 1.39 | 1.39 | 1.39 |
| Citric acid, anhydrous | 0.31 | 0.31 | 0.31 |
| Sodium citrate | 0.36 | 0.36 | 0.36 |
| Sodium benzoate | 5.00 | 5.00 | 5.00 |
| Sucralose | 0.70 | 0.70 | 0.70 |
| Simethicone | 0.15 | 0.15 | 0.15 |
| Artificial cherry flavor | 0.50 | 0.50 | 0.50 |
| Polysorbate 80 | 0.50 | 0.50 | 0.50 |
| Avicel ® RC-591 | 7.5 | 10.00 | 15.00 |
| Water | q.s. | q.s. | q.s. |
| pH | 5.36 | 5.33 | 5.34 |

[a] = equivalent to 1 mg/ml Amlodipine

The results of the HPLC analysis for amlodipine and the main degradants in the samples stored at 5° C. are provided in Table J-2.

TABLE J-2

Assay and Primary Degradants Present in the Formulations

| Weeks | Formulation | | |
|---|---|---|---|
| | J1 | J2 | J3 |
| | Amlodipine (% initial) | | |
| Initial | 100.00 | 100.00 | 100.00 |
| 2 | 98.80 | 96.18 | 96.45 |
| 4 | 99.03 | 96.35 | 96.89 |
| 6 | 100.53 | 99.32 | 98.52 |
| 8 | 98.71 | 96.96 | 96.77 |
| 12 | 97.58 | 96.75 | 96.00 |
| 26 | 99.24 | 98.27 | 97.90 |
| | USP Impurity A/EP Impurity D (wt % of Amlodipine) | | |
| Initial | 0.02 | 0.02 | 0.04 |
| 2 | 0.03 | 0.03 | 0.02 |
| 4 | 0.04 | 0.04 | 0.06 |
| 6 | 0.02 | 0.02 | 0.04 |
| 8 | 0.03 | 0.03 | 0.05 |
| 12 | 0.02 | 0.03 | 0.03 |
| 26 | 0.04 | 0.06 | 0.07 |
| | Impurity RRT 0.97 (wt % of Amlodipine) | | |
| Initial | 0.00 | 0.00 | 0.00 |
| 2 | 0.00 | 0.00 | 0.00 |
| 4 | 0.00 | 0.00 | 0.00 |
| 6 | 0.00 | 0.00 | 0.00 |

TABLE J-2-continued

Assay and Primary Degradants Present in the Formulations

| | Formulation | | |
|---|---|---|---|
| Weeks | J1 | J2 | J3 |
| 8 | 0.00 | 0.00 | 0.00 |
| 12 | 0.00 | 0.00 | 0.00 |
| 26 | 0.01 | 0.01 | 0.01 |
| Total Impurities (wt % of Amlodipine) | | | |
| Initial | 0.09 | 0.09 | 0.14 |
| 2 | 0.14 | 0.16 | 0.10 |
| 4 | 0.12 | 0.14 | 0.14 |
| 6 | 0.09 | 0.10 | 0.09 |
| 8 | 0.16 | 0.13 | 0.18 |
| 12 | 0.16 | 0.18 | 0.18 |
| 26 | 0.18 | 0.22 | 0.18 |

The results of the HPLC analysis for amlodipine and the main degradants in the samples stored at 25° C. are provided in Table J-3.

TABLE J-3

Assay and Primary Degradants Present in the Formulations

| | Formulation | | |
|---|---|---|---|
| Weeks | J1 | J2 | J3 |
| Amlodipine (% initial) | | | |
| Initial | 100.00 | 100.00 | 100.00 |
| 2 | 99.27 | 97.16 | 96.52 |
| 4 | 98.94 | 97.73 | 96.89 |
| 6 | 99.61 | 98.81 | 98.20 |
| 8 | 97.34 | 96.91 | 95.85 |
| 12 | 95.57 | 95.48 | 93.25 |
| 26 | 95.39 | 93.67 | 92.65 |
| USP Impurity A/EP Impurity D (wt % of Amlodipine) | | | |
| Initial | 0.02 | 0.02 | 0.04 |
| 2 | 0.05 | 0.04 | 0.06 |
| 4 | 0.06 | 0.04 | 0.06 |
| 6 | 0.08 | 0.05 | 0.06 |
| 8 | 0.05 | 0.06 | 0.08 |
| 12 | 0.06 | 0.07 | 0.09 |
| 26 | 0.09 | 0.09 | 0.13 |
| Impurity RRT 0.97 (wt % of Amlodipine) | | | |
| Initial | 0.00 | 0.00 | 0.00 |
| 2 | 0.01 | 0.01 | 0.01 |
| 4 | 0.02 | 0.02 | 0.03 |
| 6 | 0.03 | 0.03 | 0.03 |
| 8 | 0.03 | 0.03 | 0.04 |
| 12 | 0.03 | 0.03 | 0.04 |
| 26 | 0.03 | 0.03 | 0.04 |
| Total Impurities (wt % of Amlodipine) | | | |
| Initial | 0.09 | 0.09 | 0.14 |
| 2 | 0.20 | 0.27 | 0.28 |
| 4 | 0.38 | 0.39 | 0.42 |
| 6 | 0.52 | 0.55 | 0.59 |
| 8 | 0.69 | 0.73 | 0.83 |
| 12 | 0.96 | 1.11 | 1.15 |
| 26 | 1.64 | 1.37 | 1.98 |

Example K

Clinical Trial: Bioavailability Study of 5 Mg Amlodipine Oral Suspension Vs. Norvasc® 5 Mg Tablets Under Fasted Conditions The objective of this single dose open-label, randomized, two-period, two-treatment crossover study was to compare the relative oral bioavailability of a test formulation of 5 mL of amlodipine oral suspension, 1 mg/mL (formulation F4), to an equivalent oral dose of the commercially available comparator product, Norvasc® (amlodipine besylate) 5 mg tablet, when administered under fasted conditions in healthy adults.

Study design: Ten healthy adult subjects received a single 5 mL dose of amlodipine oral suspension, 1 mg/mL, formulation F4 (Treatment A), in one period and a separate single dose of Norvasc® (amlodipine besylate) 5 mg tablet (Treatment B) in another period. Each treatment was administered after an overnight fast of at least 10 hours, followed by a 4-hour fast postdose.

During each period, blood samples were obtained prior to and following each dose at selected times through 168 hours postdose. Pharmacokinetic parameters were calculated for each formulation using non-compartmental methods.

Statistical Methods: The concentration-time data were analyzed using noncompartmental methods in Phoenix™ WinNonlin® (Version 6.3, Pharsight Corporation). Concentration-time data that were below the limit of quantitation (BLQ) were treated as zero in the data summarization and descriptive statistics. In the pharmacokinetic analysis, BLQ concentrations were treated as zero from time-zero up to the time at which the first quantifiable concentration was observed; embedded and/or terminal BLQ concentrations were treated as "missing". Actual sample times were used for all pharmacokinetic and statistical analyses. Analysis of variance (ANOVA) and the Schuirmann's two one-sided t-test procedures at the 5% significance level were applied to the log-transformed pharmacokinetic exposure parameters, $C_{max}$, $AUC_{last}$, and $AUC_{inf}$. The 90% confidence interval for the ratio of the geometric means (Test/Reference) was calculated. Bioequivalence was declared if the lower and upper confidence intervals (CIs) of the log-transformed parameters were within 80% to 125%.

Results: A total of 10 subjects participated in the study and 8 of these subjects completed both study periods. Based on the geometric mean ratios of amlodipine AUCs ($AUC_{last}$ and $AUC_{inf}$), the bioavailability of the amlodipine oral suspension (formulation F4) relative to the Norvasc® tablet was approximately 103% to 104%. The geometric mean ratio of amlodipine $C_{max}$ was approximately 100%. The 90% CI for comparing the maximum exposure to amlodipine, based on ln ($C_{max}$), was within the accepted 80% to 125% limits. The 90% CIs for comparing total systemic exposure to amlodipine, based on ln ($AUC_{last}$) and ln ($AUC_{inf}$), was within the accepted 80% to 125% limits. Therefore, the 5 mL test formulation of amlodipine oral suspension, 1 mg/mL, is bioequivalent to the reference product, Norvasc® (amlodipine besylate) tablet, 5 mg, under fasted conditions.

Example L

Characterization of Amlodipine Benzoate

A suspension was prepared by adding 0.50 g of NuSil Med-342 simethicone (30% simethicone) to 90 mL water in a glass beaker with stirring. Sodium benzoate (5.00 g) was added to the suspension and dissolved. Amlodipine besylate (1.40 g) was added to 10 mL water, then the amlodipine suspension was added to the benzoate suspension over 2-4 minutes. The resulting suspension was mixed for 30 minutes at ambient temperature.

The solids were collected on filter paper and washed with ~150 mL cold water in 15 mL portions. The solid was dried under vacuum for 1 hour, then dried in a desiccator for 18 hours. A portion of the solids were weighed and dissolved in water/HPLC diluent and the resulting solution was analyzed by a validated HPLC procedure for the presence of amlodipine and benzoic acid. The resulting molar ratio of benzoic acid:amlodipine in the solid was calculated as 1.00:1.05 demonstrating the formation of amlodipine benzoate.

Example M

Solubility of Amlodipine Besylate and Amlodipine Benzoate in the Presence of Added Sodium Benzoate Amlodipine benzoate was prepared by adding 1.39 g amlodipine besylate to 100 ml purified water in a glass container. Five grams of sodium benzoate were then added and the solution was stirred for 30 minutes at ambient temperature. The resulting suspension was vacuum filtered through #1 Whatman filter paper to collect the insoluble fraction. The collected solids were rinsed with ten separate 15 mL increments (150 mL total) of 1-5° C. degree water. The solids were dried on the vacuum filtration apparatus for 1 hour then dried overnight in a desiccator.

Figure 2:
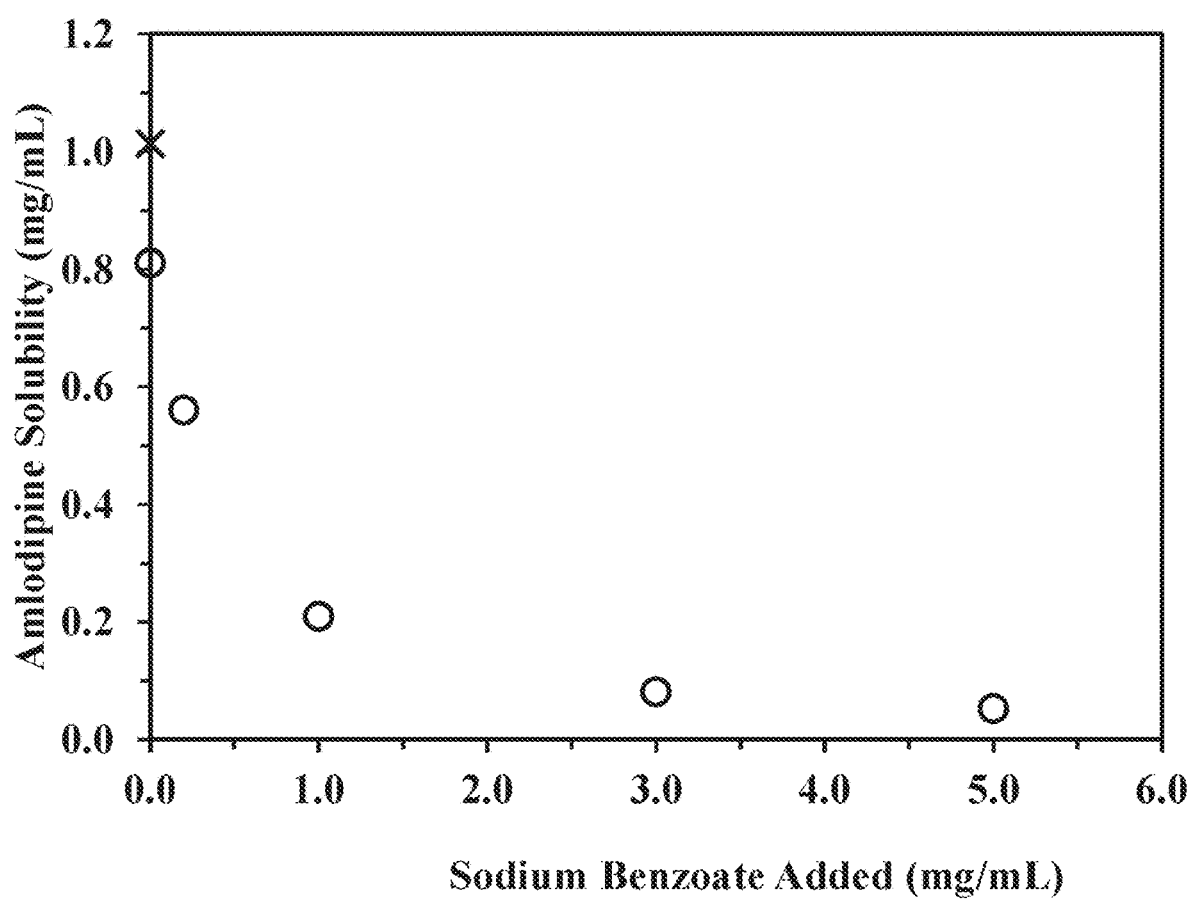
FIG. 2 shows the amount of amlodipine in solution for (×) amlodipine besylate and (○) amlodipine benzoate in the presence of added sodium benzoate.

Fifteen milliliter polypropylene centrifuge tubes were set up in duplicate as shown in Table M-1. Amlodipine besylate or amlodipine benzoate was added to each tube in amounts in excess of the anticipated solubility. Ten milliliter aliquots of water, or water with varying amounts of sodium benzoate were added to each tube. The pH of each tube was adjusted to 5.3 with the addition of citric acid. The tubes were capped and mixed by inversion for 5 days to allow the suspensions to equilibrate. After the equilibration time, the tubes were opened and immediately filtered through 0.45 micron nylon filters. The clear filtrates were analyzed according to the method in Example A. The results of the HPLC analysis for the amounts of amlodipine in solution are presented in FIG. 2.

TABLE M-1

Composition of Solubility Study Tubes

| Component | Duplicate Tube Set | | | | | |
|---|---|---|---|---|---|---|
| | J1 | J2 | J3 | J4 | J5 | J6 |
| Amlodipine besylate (mg) | 50 | — | — | — | — | — |
| Amlodipine benzoate (mg) | — | 50 | 50 | 50 | 50 | 50 |
| Citric acid, anhydrous (mg) | Amount as needed to achieve pH 5.3 | | | | | |
| Sodium benzoate (mg) | 0 | 0 | 2 | 10 | 30 | 50 |
| Water (mL) | 10 | 10 | 10 | 10 | 10 | 10 |
| Measured pH | 5.3 | 5.3 | 5.3 | 5.3 | 5.3 | 5.3 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating Coronary Artery Disease (CAD) in a subject comprising administering to the subject an oral liquid formulation, wherein the oral liquid formulation comprises:
    (i) amlodipine benzoate in an amount corresponding to 1.0 mg/ml amlodipine freebase;
    (ii) 0.2 mg/ml to 10 mg/ml of sodium benzoate;
    (iii) a suspension aid comprising silicon dioxide, hydroxypropyl methylcellulose, methylcellulose, microcrystalline cellulose, carboxymethyl cellulose sodium, polyvinylpyrrolidone, xanthan gum, or a combination thereof;
    (iv) 0.05 mg/ml to 1.0 mg/ml of an antifoaming agent;
    (v) a non-ionic surfactant that is present at about 0.1 mg/ml to about 3.0 mg/ml in the oral liquid formulation;
    (vi) optionally one or more selected from a buffer, a flavoring agent, a sweetener, and a preservative; and
    (vii) water;
    wherein the oral liquid formulation is stable at 5±5° C. for a storage period of at least 12 months; and
    wherein the stable oral liquid formulation has 95% w/w or greater of the initial amlodipine amount and 5% w/w or less total impurities or related substances at the end of the given storage period.

2. The method of claim 1, wherein the CAD is angiographically documented coronary artery disease.

3. The method of claim 2, wherein the angiographically documented coronary artery disease is in patients without heart failure or an ejection fraction <40%.

4. The method of claim 1, wherein the formulation is further administered in combination with an additional antianginal agent.

5. The method of claim 1, wherein the CAD is chronic stable angina.

6. The method of claim 1, wherein the CAD is vasospastic angina.

7. The method of claim 1, wherein the amlodipine benzoate is formed in situ.

8. The method of claim 1, wherein the amlodipine benzoate is formed by the reaction of amlodipine besylate with a molar excess of sodium benzoate.

9. The method of claim 1, wherein the oral liquid formulation comprises a flavoring agent and a sweetener.

10. The method of claim 1, wherein the oral liquid formulation is in the form of a suspension.

11. The method of claim 1, wherein the pH is between 4 and 6.

12. The method of claim 1, wherein the suspension aid is present in the oral liquid formulation at 5.0 mg/ml to 15.0 mg/ml.

13. The method of claim 1, wherein the suspension aid is present in the oral liquid formulation at 3.0 mg/ml to 10.0 mg/ml.

14. The method of claim 1, wherein the suspension aid comprises silicon dioxide, hydroxypropyl methylcellulose, microcrystalline cellulose, carboxymethyl cellulose sodium, or any combination thereof.

15. The method of claim 1, wherein the antifoaming agent is simethicone and is present in the oral liquid formulation at about 0.05 mg/ml to about 0.3 mg/ml.

16. The method of claim 1, wherein the non-ionic surfactant is a block copolymers of polyethylene glycol and polypropylene glycol, a polyethylene glycol octylphenyl ether, polyethylene glycol alkyl ether, or any combination thereof.

17. A method of treating hypertension in a subject comprising administering to the subject an oral liquid formulation, wherein the oral liquid formulation comprises:
(i) amlodipine benzoate in an amount corresponding to 1.0 mg/ml amlodipine freebase;
(ii) 0.2 mg/ml to 10 mg/ml of sodium benzoate;
(iii) a suspension aid comprising silicon dioxide, hydroxypropyl methylcellulose, methylcellulose, microcrystalline cellulose, carboxymethyl cellulose sodium, polyvinylpyrrolidone, xanthan gum, or a combination thereof;
(iv) 0.05 mg/ml to 1.0 mg/ml of an antifoaming agent;
(v) a non-ionic surfactant that is present at about 0.1 mg/ml to about 3.0 mg/ml in the oral liquid formulation;
(vi) optionally one or more selected from a buffer, a flavoring agent, a sweetener, and a preservative; and
(vii) water;
wherein the oral liquid formulation is stable at 5±5° C. for a storage period of at least 12 months; and
wherein the stable oral liquid formulation has 95% w/w or greater of the initial amlodipine amount and 5% w/w or less total impurities or related substances at the end of the given storage period.

18. The method of claim 17, wherein the hypertension is primary or secondary hypertension.

19. The method of claim 17, wherein the subject has blood pressure values greater than or equal to 140/90 mm Hg.

20. The method of claim 17, wherein the oral liquid formulation is further administered in combination with an agent selected from the group consisting of diuretics, beta blockers, alpha blockers, mixed alpha and beta blockers, calcium channel blockers, angiotensin II receptor antagonists, Angiotensin-converting enzyme (ACE) inhibitors, aldosterone antagonists, and alpha-2 agonists.

21. The method of claim 17, wherein the amlodipine benzoate is formed in situ.

22. The method of claim 17, wherein the amlodipine benzoate is formed by the reaction of amlodipine besylate with a molar excess of sodium benzoate.

23. The method of claim 17, wherein the oral liquid formulation comprises a flavoring agent and a sweetener.

24. The method of claim 17, wherein the oral liquid formulation is in the form of a suspension.

25. The method of claim 17, wherein the pH is between 4 and 6.

26. The method of claim 17, wherein the suspension aid is present in the oral liquid formulation at 5.0 mg/ml to 15.0 mg/ml.

27. The method of claim 17, wherein the suspension aid is present in the oral liquid formulation at 3.0 mg/ml to 10.0 mg/ml.

28. The method of claim 17, wherein the suspension aid comprises silicon dioxide, hydroxypropyl methylcellulose, microcrystalline cellulose, carboxymethyl cellulose sodium, or any combination thereof.

29. The method of claim 17, wherein the antifoaming agent is simethicone and is present in the oral liquid formulation at about 0.05 mg/ml to about 0.3 mg/ml.

30. The method of claim 17, wherein the non-ionic surfactant is a block copolymers of polyethylene glycol and polypropylene glycol, a polyethylene glycol octylphenyl ether, polyethylene glycol alkyl ether, or any combination thereof.

* * * * *